(12) United States Patent
Brister et al.

(10) Patent No.: US 9,895,248 B2
(45) Date of Patent: Feb. 20, 2018

(54) ULTRASONIC SYSTEMS AND METHODS FOR LOCATING AND/OR CHARACTERIZING INTRAGASTRIC DEVICES

(71) Applicant: Obalon Therapeutics, Inc., Carlsbad, CA (US)

(72) Inventors: Mark C. Brister, Encinitas, CA (US); Neil R. Drake, San Diego, CA (US); Sheldon Nelson, Vista, CA (US)

(73) Assignee: Obalon Therapeutics, Inc., Carlsbad, CA (US)

( * ) Notice: Subject to any disclaimer, the term of this patent is extended or adjusted under 35 U.S.C. 154(b) by 201 days.

(21) Appl. No.: 14/877,846

(22) Filed: Oct. 7, 2015

(65) Prior Publication Data

US 2016/0100970 A1  Apr. 14, 2016

Related U.S. Application Data

(60) Provisional application No. 62/062,081, filed on Oct. 9, 2014.

(51) Int. Cl.
*A61F 5/00* (2006.01)
*A61M 29/02* (2006.01)

(52) U.S. Cl.
CPC ............ *A61F 5/0046* (2013.01); *A61F 5/003* (2013.01); *A61F 5/0036* (2013.01); *A61F 5/0043* (2013.01); *A61F 2005/002* (2013.01)

(58) Field of Classification Search
CPC .... A61F 5/0046; A61F 5/0043; A61F 5/0036; A61F 5/003; A61F 2005/002
See application file for complete search history.

(56) References Cited

U.S. PATENT DOCUMENTS

| | | | |
|---|---|---|---|
| 2,183,900 | A | 12/1939 | Voit et al. |
| 3,788,322 | A | 1/1974 | Michaels |
| 3,797,492 | A | 3/1974 | Place |
| 4,133,315 | A | 1/1979 | Berman et al. |
| 4,234,454 | A | 11/1980 | Strope |
| 4,236,521 | A | 12/1980 | Lauterjung |
| 4,246,893 | A | 1/1981 | Berson |
| 4,340,626 | A | 7/1982 | Rudy |
| 4,416,267 | A | 11/1983 | Garren et al. |
| 4,485,805 | A | 12/1984 | Foster, Jr. |

(Continued)

FOREIGN PATENT DOCUMENTS

| | | |
|---|---|---|
| DE | 3540936 | 10/1986 |
| EP | 0 103 481 | 3/1984 |

(Continued)

OTHER PUBLICATIONS

Al Kahtani et al., Aug. 28, 2008, Bio-Enteric Intragastric Balloon in Obese Patients: A Retrospective Analysis of King Faisal Specialist Hospital Experience; Obes Surg, 8 pp.

(Continued)

*Primary Examiner* — Julian W Woo
(74) *Attorney, Agent, or Firm* — Knobbe Martens Olson & Bear, LLP

(57) ABSTRACT

Devices and methods for treating obesity are provided. More particularly, intragastric devices and methods of fabricating, deploying, inflating, locating, tracking, monitoring, deflating, and retrieving the same are provided.

10 Claims, 10 Drawing Sheets

(56) References Cited

U.S. PATENT DOCUMENTS

| | | | |
|---|---|---|---|
| 4,489,440 A | 12/1984 | Chaoui | |
| 4,517,979 A | 5/1985 | Pecenka | |
| 4,545,367 A | 10/1985 | Tucci | |
| 4,560,392 A | 12/1985 | Basevi | |
| 4,607,618 A | 8/1986 | Angelchik | |
| 4,694,827 A | 9/1987 | Weiner et al. | |
| 4,718,639 A | 1/1988 | Sherwood et al. | |
| 4,723,547 A | 2/1988 | Kullas et al. | |
| 4,739,758 A | 4/1988 | Lai et al. | |
| 4,748,562 A | 5/1988 | Miller et al. | |
| 4,812,315 A | 3/1989 | Tarabishi | |
| 4,813,934 A | 3/1989 | Engelson et al. | |
| 4,857,029 A | 8/1989 | Dierick et al. | |
| 4,899,747 A | 2/1990 | Garren et al. | |
| 4,917,885 A | 4/1990 | Chiba et al. | |
| 4,925,446 A | 5/1990 | Garay et al. | |
| 4,929,214 A | 5/1990 | Liebermann | |
| 5,049,106 A | 9/1991 | Kim et al. | |
| 5,084,061 A | 1/1992 | Gau et al. | |
| 5,129,915 A | 7/1992 | Cantenys et al. | |
| 5,234,454 A | 8/1993 | Bangs | |
| 5,259,399 A | 11/1993 | Brown | |
| 5,308,326 A | 5/1994 | Zimmon | |
| 5,425,382 A | 6/1995 | Golden et al. | |
| 5,431,917 A | 7/1995 | Yamamoto et al. | |
| 5,622,169 A | 4/1997 | Golden et al. | |
| 5,713,141 A | 2/1998 | Mitchell et al. | |
| 5,728,119 A | 3/1998 | Smith et al. | |
| 5,852,889 A | 12/1998 | Rinaldi | |
| 5,868,141 A | 2/1999 | Ellias | |
| 5,879,297 A | 3/1999 | Haynor et al. | |
| 5,897,205 A | 4/1999 | Sinsteden | |
| 5,910,128 A | 6/1999 | Quinn | |
| 5,948,227 A | 9/1999 | Dubrow | |
| 6,042,710 A | 3/2000 | Dubrow | |
| 6,129,668 A | 10/2000 | Haynor et al. | |
| 6,216,028 B1 | 4/2001 | Haynor et al. | |
| 6,263,230 B1 | 7/2001 | Haynor et al. | |
| 6,427,089 B1 | 7/2002 | Knowlton | |
| 6,454,785 B2 | 9/2002 | De Hoyos Garza | |
| 6,579,301 B1 | 6/2003 | Bales et al. | |
| 6,682,473 B1 | 1/2004 | Matsuura et al. | |
| 6,733,512 B2 | 5/2004 | McGhan et al. | |
| 6,981,980 B2 | 1/2006 | Sampson et al. | |
| 6,988,983 B2 | 1/2006 | Connors et al. | |
| 7,031,946 B1 | 4/2006 | Tamai et al. | |
| 7,032,822 B2 | 4/2006 | Waters | |
| 7,035,818 B1 | 4/2006 | Bandy et al. | |
| 7,035,877 B2 | 4/2006 | Markham et al. | |
| 7,192,397 B2 | 3/2007 | Lewkowicz et al. | |
| 7,682,306 B2 | 3/2010 | Shah | |
| 7,699,863 B2 | 4/2010 | Marco et al. | |
| 7,854,745 B2 | 12/2010 | Brister et al. | |
| 8,105,247 B2 | 1/2012 | Buchwald | |
| 8,162,969 B2 | 4/2012 | Brister et al. | |
| 8,202,291 B1 | 6/2012 | Brister et al. | |
| 8,226,602 B2 * | 7/2012 | Quijana | A61F 5/0003 604/103.02 |
| 8,282,666 B2 | 10/2012 | Birk | |
| 8,292,911 B2 | 10/2012 | Brister et al. | |
| 8,428,691 B2 | 4/2013 | Byrd et al. | |
| 8,491,464 B2 | 7/2013 | Yokoi et al. | |
| 8,535,230 B2 | 9/2013 | Maschke | |
| 8,562,589 B2 | 10/2013 | Imran | |
| 8,721,620 B2 | 5/2014 | Imran | |
| 8,734,429 B2 | 5/2014 | Imran et al. | |
| 8,764,733 B2 | 7/2014 | Imran | |
| 8,809,269 B2 | 8/2014 | Imran | |
| 8,809,271 B2 | 8/2014 | Imran | |
| 8,836,513 B2 | 9/2014 | Hafezi et al. | |
| 8,847,766 B2 | 9/2014 | Zdeblick et al. | |
| 8,858,432 B2 | 10/2014 | Robertson et al. | |
| 2003/0021822 A1 | 1/2003 | Lloyd | |
| 2003/0171768 A1 | 9/2003 | McGhan | |
| 2004/0044351 A1 | 3/2004 | Searle | |
| 2004/0102677 A1 | 5/2004 | Frering | |
| 2004/0186502 A1 | 9/2004 | Sampson | |
| 2005/0131281 A1 | 6/2005 | Ayer et al. | |
| 2005/0192614 A1 | 9/2005 | Binmoeller | |
| 2005/0222329 A1 | 10/2005 | Shah et al. | |
| 2005/0266109 A1 | 12/2005 | Chin et al. | |
| 2005/0267405 A1 | 12/2005 | Shah | |
| 2005/0267595 A1 | 12/2005 | Chen et al. | |
| 2006/0058829 A1 | 3/2006 | Sampson et al. | |
| 2006/0178691 A1 | 8/2006 | Binmoeller | |
| 2006/0224145 A1 | 10/2006 | Gillis et al. | |
| 2007/0078476 A1 | 4/2007 | Hull et al. | |
| 2007/0100208 A1 | 5/2007 | Lewkowicz et al. | |
| 2007/0100367 A1 * | 5/2007 | Quijano | A61F 5/003 606/192 |
| 2007/0100369 A1 | 5/2007 | Cragg et al. | |
| 2007/0104754 A1 | 5/2007 | Sterling et al. | |
| 2007/0104755 A1 | 5/2007 | Sterling et al. | |
| 2007/0110934 A1 | 5/2007 | Goldman | |
| 2007/0129735 A1 | 6/2007 | Filipi et al. | |
| 2007/0149994 A1 | 6/2007 | Sosnowski et al. | |
| 2007/0156248 A1 | 7/2007 | Marco et al. | |
| 2007/0173881 A1 | 7/2007 | Birk et al. | |
| 2007/0207199 A1 | 9/2007 | Sogin et al. | |
| 2007/0212559 A1 | 9/2007 | Shah | |
| 2007/0250101 A1 | 10/2007 | Horn et al. | |
| 2007/0288033 A1 | 12/2007 | Murature et al. | |
| 2007/0293885 A1 | 12/2007 | Binmoeller | |
| 2008/0051866 A1 | 2/2008 | Chen et al. | |
| 2008/0172079 A1 | 7/2008 | Birk | |
| 2008/0255601 A1 | 10/2008 | Birk | |
| 2008/0306506 A1 | 12/2008 | Leatherman et al. | |
| 2009/0082644 A1 | 3/2009 | Li | |
| 2009/0118756 A1 | 5/2009 | Valencon et al. | |
| 2009/0182368 A1 | 7/2009 | Lunsford et al. | |
| 2009/0182424 A1 | 7/2009 | Marco et al. | |
| 2009/0187206 A1 | 7/2009 | Binmoeller et al. | |
| 2009/0192535 A1 | 7/2009 | Kasic, II et al. | |
| 2009/0222065 A1 | 9/2009 | Dlugos et al. | |
| 2009/0259246 A1 | 10/2009 | Eskaros et al. | |
| 2010/0063530 A1 | 3/2010 | Valencon | |
| 2010/0100115 A1 | 4/2010 | Soetermans et al. | |
| 2010/0100116 A1 | 4/2010 | Brister et al. | |
| 2010/0100117 A1 | 4/2010 | Brister et al. | |
| 2010/0137897 A1 | 6/2010 | Brister et al. | |
| 2010/0168782 A1 | 7/2010 | Hancock | |
| 2010/0198249 A1 | 8/2010 | Sabliere | |
| 2010/0222802 A1 | 9/2010 | Gillespie et al. | |
| 2011/0021881 A1 | 1/2011 | Wenchell et al. | |
| 2011/0202127 A1 | 8/2011 | Mauch et al. | |
| 2011/0295300 A1 | 12/2011 | Verd et al. | |
| 2012/0010590 A1 | 1/2012 | Imran | |
| 2012/0191123 A1 | 7/2012 | Brister et al. | |
| 2012/0191124 A1 | 7/2012 | Brister et al. | |
| 2012/0232576 A1 | 9/2012 | Brister et al. | |
| 2012/0296365 A1 | 11/2012 | Nguyen | |
| 2013/0012980 A1 | 1/2013 | Brister et al. | |
| 2013/0165859 A1 | 6/2013 | Imran | |
| 2013/0226219 A1 | 8/2013 | Brister et al. | |
| 2013/0289604 A1 | 10/2013 | Brister et al. | |
| 2014/0221912 A1 | 8/2014 | Imran | |
| 2014/0221927 A1 | 8/2014 | Imran et al. | |

FOREIGN PATENT DOCUMENTS

| | | |
|---|---|---|
| EP | 0 246 999 | 11/1987 |
| JP | 62-286470 | 12/1987 |
| WO | WO 87/00034 | 1/1987 |
| WO | WO 99/25418 | 5/1999 |
| WO | WO 01/068007 | 9/2001 |
| WO | WO 02/016001 | 2/2002 |
| WO | WO 02/040081 | 5/2002 |
| WO | WO 02/091961 | 11/2002 |
| WO | WO 03/055420 | 7/2003 |
| WO | WO 04/084763 | 10/2004 |
| WO | WO 06/020929 | 2/2006 |
| WO | WO 06/116718 | 11/2006 |
| WO | WO 07/053556 | 5/2007 |
| WO | WO 07/074445 | 7/2007 |

(56) References Cited

FOREIGN PATENT DOCUMENTS

| | | |
|---|---|---|
| WO | WO 07/136735 | 11/2007 |
| WO | WO 08/052136 | 5/2008 |
| WO | WO 09/055386 | 4/2009 |
| WO | WO 09/059803 | 5/2009 |
| WO | WO 09/086119 | 7/2009 |
| WO | WO 10/045477 | 4/2010 |
| WO | WO 10/045482 | 4/2010 |
| WO | WO 10/097774 | 8/2010 |
| WO | WO 11/136745 | 11/2011 |
| WO | WO 12/099610 | 7/2012 |
| WO | WO 2014/081725 A2 | 5/2014 |

OTHER PUBLICATIONS

Almeida et al., 2008, Capsule endoscopy assisted by traditional upper endoscopy Revista Española De Enfermedades Digestivas, 100(12):758-763.
Al-Momen et al., 2005, Intragastric Balloon for Obesity: A Retrospective Evaluation of Tolerance and Efficacy, Obes Surg, 15(1):101-105.
Ambe et al., 2012, Swallowed Foreign Bodies in Adults Dtsch Arztebl Int, 109(50):869-875.
Bar-Shalom et al., 1988, Tracking and Data Association, Academic Press, Inc., Boston.
Benjamin et al., Sep. 1988, Double-Blind Controlled Trial of the Garren-Edwards Gastric Bubble: An Adjunctive Treatment for Exogenous Obesity, Gastroenterology, 95(3):581-588.
Carvalho et al., 2008, An Improved Intragastric Balloon Procedure Using a New Balloon: Preliminary Analysis of Safety and Efficacy, Obes Surg, 6 pp.
Coskun et al., Sep. 2008, Bioenterics Intragastric Balloon: Clinical Outcomes of the First 100 Patients-A Turkish Experience, Obes Surg, 18(9):1154-1156.
Dastis et al., Jul. 2008, Intragastric Balloon for Weight Loss: Results in 100 Individuals Followed for at Least 2.5 Years; Endoscopy, 41(7):575-580.
De Waele et al., Apr. 2001, Endoscopic Volume Adjustment of Intragastric Balloons for Intolerance, Obes Surg, 11(2):223-224.
Doldi et al., 2002, Treatment of Morbid Obesity With Intragastric Balloon in Association With Diet; Obes Surg, 12(4):583-587.
Dumonceau, Dec. 2008, Evidence-Based Review of the Bioenterics Intragastric Balloon for Weight Loss, Obes Surg, 18(12):1611-1617.
Durrans et al., 1989, Comparison of Weight Loss With Short Term Dietary and Intragastric Balloon Treatment; Gut, 30:565-568.
Eckhauser et al., 1984, Hydrostatic Balloon Dilation for Stomal Stenosis after Gastric Partitioning, Surgical Gastroenterology, 3(1):43-50.
Evans et al., 2001, Intragastric Balloon in the Treatment of Patients with Morbid Obesity, British Journal of Surgery, 88:1245-1248.
Fernandes et al., Jan. 24, 2007, Intragastric Balloon for Obesity (Review), The Cochrane Collaboration, John Wiley & Sons, Ltd., Issue 1, 57 pp.
Forestieri et al., May 2006, Heliosphere Bag in the Treatment of Severe Obesity: Preliminary Experience, Obes Surg, 16(5):635-637.
Gaggiotti et al., 2007, Adjustable Totally Implanted Intragastric Prosthesis (ATIIP). Endogast for Treatment of Morbid Obesity: One Year Follow-Up of a Multicenter Prospective Clinical Survey; Obesity Surgery, 17:949-956.
Geliebter et al., 1990, Gastric balloon to treat obesity: a double-blind study in nondieting subjects, The American Journal of Clinical Nutrition, 51:584-588.
Genco et al., Jan. 2006, Bioenterics Intragastric Balloon (BIB): A Short-Term, Double-Blind, Randomized, Controlled, Crossover Study on Weight Reduction in Morbidly Obese Patients, International Journal of Obesity, 30(1):129-133.
Genco et al., 2005, Bioenterics Intragastric Balloon: The Italian Experience With 2,515 Patients; Obesity Surgery, 15(8):1161-1164.
Genco et al., 2008, Intragastric Balloon or Diet Alone? A Retrospective Evaluation, Obesity Surgery, 18(8):989-992.
Genco et al., 2009, Laparoscopic Sleeve Gastrectomy Versus Intragastric Balloon: A Case-Control Study, Surg Endosc. Springer Science & Business Media, 4 pp.
Gottig et al., Jun. 2009, Analysis of Safety and Efficacy of Intragastric Balloon in Extremely Obese Patients, Obesity Surgery, 19(6):677-683.
Imaz et al., Jul. 2008, Safety and Effectiveness of the Intragastric Balloon for Obesity. A Meta-Analysis; Obesity Surgery; 18(7):841-846.
Langer, Apr. 30, 1998, Drug delivery and targeting, Nature, 392 Supp (6679):5-10.
Mackay, 2.9. Power Sources, in Bio-Medical Telemetry: Sensing and Transmitting Biological Information from Animals and Man, 2d ed., IEEE Press, New York, 1993, pp. 62-70.
Malik, 2006, Endoluminal and Transluminal Surgery: Current Status and Future Possibilities; Surgical Endoscopy, 20(8):1179-1192.
Martin et al., Jul. 2007, Safety of the Ullorex Oral Intragastric Balloon for the Treatment of Obesity, Journal of Diabetic Science and Technology, 1(4):574-581.
Mathus-Vliegen et al., Aug. 1990, Intragastric Ballon in the Treatment of Super-morbid Obesity—Double-Blind, Sham-Controlled, Crossover Evaluation of 500-Milliliter Balloon, Gastroenterology, 99(2):362-369.
Melissas et al., 2006, The Intragastric Balloon—Smoothing the Path to Bariatric Surgery, Obesity Surgery, 16:897-902.
Mion et al., Jul. 2007, Tolerance and Efficacy of an Air-Filled Balloon in Non-Morbidly Obese Patients: Results of a Prospective Multicenter Study; Obesity Surgery, 17(7):764-769.
Nieben et al., Jan. 1982, Intragastric Balloon as an Artificial Bezoar for Treatment of Obesity, The Lancet, 1(8265):198-199.
Ramhamadany et al, 1989, Effect of the Gastric Balloon Versus Sham Procedure on Weight Loss in Obese Subjects; Gut, 30:1054-1057.
Remington's Pharmaceutical Sciences, Mace Publishing Company, Philadelphia, Pa., 17th ed. (1985).
Rodriguez-Hermosa et al., 2009, Gastric Necrosis: A Possible Complication of the Use of the Intragastric Balloon in a Patient Previously Submitted to Nissen Fundoplication; Obesity Surgery, 19:1456-1459.
Roman et al., Apr. 2004, Intragastric Balloon for "Non-Morbid" Obesity: A Retrospective Evaluation of Tolerance and Efficacy; Obesity Surgery, 14(4):539-544.
Sallet et al., Aug. 2004, Brazilian Multicenter Study of the Intragastric Balloon, Obesity Surgery, 14(7):991-998.
Sherlock II Tip Location System, Bard Access Systems, Imaging Technologies http://www.bardaccess.com/loc-sherlock.php, 1 p.
Torres et al., 2009, Management of contact dermatitis due to nickel allergy: An update, Clinical, Cosmetic and Investigational Dermatology, 2:39-48.
Totte et al., Aug. 2001, Weight Reduction by Means of Intragastric Device: Experience With the Bioenterics Intragastric Balloon, Obesity Surgery, 11(4):519-523.
Trande et al., Dec. 2008, Efficacy, Tolerance and Safety of New Intragastric Air-Filled Balloon (Heliosphere BAG) for Obesity: The Experience of 17 Cases; Obesity Surgery, 4 pp.
U.S. Food and Drug Administration. Jul. 29, 2009. 510(k) substantial equivalence clearance, Given PillCam Platform with PillCam SB Capsules with PillCam SensorBelt http://www.accessdata.fda.gov/scripts/cdrh/cfdocs/cfpmn/pmn.cfm?id=k091405, 2 pp.
U.S. Food and Drug Administration. Jun. 2, 2006. 510(k) substantial equivalence clearance, Sherlock tip location system (TLS) detector and accessories. http://www.accessdata.fda.gov/scripts/cdrh/cfdocs/cfpmn/pmn.cfm?id=k061240, 2 pp.
U.S. Food and Drug Administration. Sep. 7, 2000. 510(k) substantial equivalence clearance, Zotran Detector. http://www.accessdata.fda.gov/scripts/cdrh/cfdocs/cfpmn/pmn.cfm?id=k000997, 2 pp.
Vălean et al., Jun. 2005, Pill Esophagitis: Two Cases Reports Romanian Journal of Gastroenterology, 14(2):159-163.
vanSonnenberg et al., Aug. 1984, Percutaneous Gastrostomy: Use of Intragastric Balloon Support, Radiology, 152(2):531-532.
Vijaysadan et al., Sep.-Oct. 2006, Revisiting Swallowed Troubles: Intestinal Complications Caused by Two Magnets—A Case Report,

(56) References Cited

OTHER PUBLICATIONS

Review and Proposed Revision to the Algorithm for the Management of Foreign Body Ingestion, JABFM, 19(5):511-516.
Wahlen et al., 2001, The Bioenterics Intragastric Balloon (BIB): How to Use It; Obesity Surgery, 11(4):524-527.
Yoshihisa et al., 2012, Metal Allergy and Systemic Contact Dermatitis: An Overview Dermatology Research and Practice, 2012:1-5, Article ID 749561.
U.S. Appl. No. 60/807,060, filed Jul. 11, 2006, titled: Acoustic Pharma-Informatic System.
U.S. Appl. No. 60/866,581, filed Nov. 20, 2006, titled: "In-Vivo Transmission Decoder".
U.S. Appl. No. 60/889,868, filed Feb. 14, 2007, titled: "Pharma Informatics System Power Source".
U.S. Appl. No. 60/889,871, filed Feb. 14, 2007, titled: "Pharma Informatics System Having Short Resistant Series Battery".

\* cited by examiner

ULTRASONIC SYSTEMS AND METHODS FOR LOCATING AND/OR CHARACTERIZING INTRAGASTRIC DEVICES

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 62/062,081 filed Oct. 9, 2015. The aforementioned application is incorporated by reference herein in its entirety, and is hereby expressly made a part of this specification.

FIELD OF THE INVENTION

Devices and methods for treating obesity are provided. More particularly, intragastric devices and methods of fabricating, deploying, inflating, monitoring, tracking, locating, and retrieving the same are provided.

BACKGROUND OF THE INVENTION

Obesity is a major health problem in developed countries. Obesity puts you at greater risk of developing high blood pressure, diabetes and many other serious health problems. In the United States, the complications of being overweight or obese are estimated to affect nearly one in three American adults, with an annual medical cost of over $80 billion and, including indirect costs such as lost wages, a total annual economic cost of over $120 billion. Except for rare pathological conditions, weight gain is directly correlated to overeating.

Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the person is satisfied with a feeling of fullness. Currently available volume-occupying devices have many shortcomings. For example, complex gastric procedures are required to insert some devices.

U.S. Pat. No. 4,133,315, the contents of which are incorporated herein by reference in their entirety, discloses an apparatus for reducing obesity comprising an inflatable, elastomeric bag and tube combination. The bag can be inserted into the patient's stomach by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastric procedure. The bag is inflated through the tube to a desired degree before the patient eats so that the desire for food is reduced. After the patient has eaten, the bag is deflated. The tube extends out of the patient's nose or abdominal cavity throughout the course of treatment.

U.S. Pat. Nos. 5,259,399, 5,234,454 and 6,454,785, the contents of which are incorporated herein by reference in their entirety, disclose intragastric volume-occupying devices for weight control that must be implanted surgically.

U.S. Pat. Nos. 4,416,267, 4,485,805, 4,607,618, 4,694,827, 4,723,547, 4,739,758, and 4,899,747 and European Patent No. 246,999, the contents of which are incorporated herein by reference in their entirety, relate to intragastric, volume-occupying devices for weight control that can be inserted endoscopically. Of these, U.S. Pat. Nos. 4,416,267, 4,694,827, 4,739,758 and 4,899,747, the contents of which are incorporated herein by reference in their entirety relate to balloons whose surface is contoured in a certain way to achieve a desired end. In U.S. Pat. Nos. 4,416,267 and 4,694,827, the contents of which are incorporated herein by reference in their entirety, the balloon is torus-shaped with a flared central opening to facilitate passage of solids and liquids through the stomach cavity. The balloon of U.S. Pat. No. 4,694,827, the contents of which are incorporated herein by reference in their entirety, has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of U.S. Pat. No. 4,739,758, the contents of which are incorporated herein by reference in their entirety, has blisters on its periphery that prevent it from seating tightly against the cardia or pylorus.

The balloons of U.S. Pat. Nos. 4,899,747 and 4,694,827, the contents of which are incorporated herein by reference in their entirety, are inserted by pushing the deflated balloon and releasably attached tubing down a gastric tube. U.S. Pat. No. 4,723,547, the contents of which are incorporated herein by reference in their entirety discloses a specially adapted insertion catheter for positioning its balloon. In U.S. Pat. No. 4,739,758, the contents of which are incorporated herein by reference in their entirety, the filler tube effects insertion of the balloon. In U.S. Pat. No. 4,485,805, the contents of which are incorporated herein by reference in their entirety, the balloon is inserted into a finger cot that is attached by string to the end of a conventional gastric tube that is inserted down the patient's throat. The balloon of European Patent No. 246,999 is inserted using a gastroscope with integral forceps.

In U.S. Pat. Nos. 4,416,267, 4,485,805, 4,694,827, 4,739,758, and 4,899,747 and European Patent No. 246,999, the contents of which are incorporated herein by reference in their entirety, the balloon is inflated with a fluid from a tube extending down from the patient's mouth. In these patents, the balloon also is provided with a self-sealing hole (U.S. Pat. No. 4,694,827, the contents of which are incorporated herein by reference in their entirety), injection site (U.S. Pat. Nos. 4,416,267 and 4,899,747, the contents of which are incorporated herein by reference in their entirety), self-sealing fill valve (U.S. Pat. No. 4,485,805, the contents of which are incorporated herein by reference in their entirety), self-closing valve (European Patent No. 246,999, the contents of which are incorporated herein by reference in their entirety) or duck-billed valve (U.S. Pat. No. 4,739,758, the contents of which are incorporated herein by reference in their entirety). U.S. Pat. No. 4,723,547, the contents of which are incorporated herein by reference in their entirety, uses an elongated thick plug and the balloon is filled by inserting a needle attached to an air source through the plug.

U.S. Pat. No. 4,607,618, the contents of which are incorporated herein by reference in their entirety, describes a collapsible appliance formed of semi-rigid skeleton members joined to form a collapsible hollow structure. The appliance is not inflatable. It is endoscopically inserted into the stomach using an especially adapted bougie having an ejector rod to release the collapsed appliance. Once released, the appliance returns to its greater relaxed size and shape.

U.S. Pat. No. 5,129,915, the contents of which are incorporated herein by reference in their entirety, relates to an intragastric balloon that is intended to be swallowed and that inflates automatically under the effect of temperature. Three ways that an intragastric balloon might be inflated by a change in temperature are discussed. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, can produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation is that it does not afford the degree of control and reproducibility of the timing of inflation that is desirable and necessary in a safe self-inflating intragastric balloon.

After swallowing, food and oral medicaments reach a patient's stomach in under a minute. Food is retained in the stomach on average from one to three hours. However, the residence time is highly variable and dependent upon such factors as the fasting or fed state of the patient. The timing of inflation of an intragastric balloon is crucial. It must be timed to avoid premature inflation in the esophagus that could lead to an esophageal obstruction or belated inflation that could lead to intestinal obstruction.

Verification the balloon is in the stomach takes some of the guesswork out of relying on mere timing after administration. Typically verification of location is done with radiography. After a patient swallows a balloon capsule, radiography is done to ensure the balloon is in the stomach after swallowing, which is visualized by a radio-opaque marker. Radiographic techniques include x-ray or fluoroscopy techniques that provide real-time images of the balloon using radiation. However, radiation may be harmful to the body if prolonged or administered in high doses. While fluoroscopy typically uses low doses, repeated use may create a risk of harm to a patient. Further, there is the risk of accidental administration of too high of a dose to a patient.

Ultrasound-based systems and methods provide advantages over the aforementioned systems and methods. Ultrasound is an oscillating sound pressure wave with a frequency greater than the upper limit of the human hearing range. Ultrasound is thus not separated from 'normal' (audible) sound based on differences in physical properties, only the fact that humans cannot hear it. Although this limit varies from person to person, it is approximately 20 kilohertz (20,000 hertz) in healthy, young adults. Ultrasound devices operate with frequencies from 20 kHz up to several gigahertz.

Ultrasonic devices may be used to detect objects and measure distances. Ultrasonic imaging (sonography) is used in both veterinary medicine and human medicine. In the nondestructive testing of products and structures, ultrasound is used to detect invisible flaws. Industrially, ultrasound is used for cleaning and for mixing, and to accelerate chemical processes. Animals such as bats and porpoises use ultrasound for locating prey and obstacles.

Ultrasonics is the application of ultrasound. Ultrasound can be used for medical imaging, detection, measurement and cleaning. At higher power levels, ultrasonics is useful for changing the chemical properties of substances.

Medical sonography (ultrasonography) is an ultrasound-based diagnostic medical imaging technique used to visualize muscles, tendons, and many internal organs, to capture their size, structure and any pathological lesions with real time tomographic images. Ultrasound has been used by radiologists and sonographers to image the human body for at least 50 years and has become a widely used diagnostic tool. The technology is relatively inexpensive and portable, especially when compared with other techniques, such as magnetic resonance imaging (MRI) and computed tomography (CT). Ultrasound is also used to visualize fetuses during routine and emergency prenatal care. Such diagnostic applications used during pregnancy are referred to as obstetric sonography. As currently applied in the medical field, properly performed ultrasound poses no known risks to the patient. Sonography does not use ionizing radiation, and the power levels used for imaging are too low to cause adverse heating or pressure effects in tissue.

Ultrasound is also increasingly being used in trauma and first aid cases, with emergency ultrasound becoming a staple of most EMT response teams. Furthermore, ultrasound is used in remote diagnosis cases where teleconsultation is required, such as scientific experiments in space or mobile sports team diagnosis. Ultrasounds are also useful in the detection of pelvic abnormalities and can involve techniques known as abdominal (transabdominal) ultrasound, vaginal (transvaginal or endovaginal) ultrasound in women, and also rectal (transrectal) ultrasound in men.

Ultrasound has been used in many different contexts, and it presents advantages when used in the intragastric device locating and characterizing context.

Medical imaging is necessary to diagnose a large number of diseases. The oldest method, die X-ray technology, delivers high-resolution images within a short examination time; however, it has the disadvantage of exposing the patient to X-rays. Ultrasound imaging is a method of image acquisition that works without using radiation. With said ultrasound imaging, ultrasound signals are sent via an ultrasound transducer into the object to be examined and a corresponding control device receives the reflected ultrasound signals and processes the receive signals for imaging purposes.

U.S. Pat. No. 8,535,230, the contents of which are incorporated herein by reference in their entirety, describes an ultrasound device including an ultrasound transducer on a robotic arm to track an object as it moves. However, such a system is incompatible with tracking a device inside the body.

U.S. Pat. No. 8,105,247, the contents of which are incorporated herein by reference in their entirety, describes use of ultrasonic transceivers to measure the size of a gastric banding device. However, that system is intended for a stationary gastric banding device and is not directly applicable to locating and characterizing a translating, rotating and transforming intragastric device.

SUMMARY OF THE INVENTION

There remains a need for a device and method of locating and characterizing in vivo an intragastric balloon device that has capabilities beyond the prior art and that avoids one or more of the aforementioned drawbacks.

A free-floating or tethered intragastric volume-occupying device or devices that maintain volume and/or internal pressure within a predetermined range over time, or which undergoes a predetermined adjustment in volume and/or internal pressure over time, is desirable. By maintaining a predetermined volume and/or internal pressure, stresses on the device leading to a breach in structural integrity can be minimized, which prevents premature and/or uncontrolled deflation or other device failure. By undergoing a predetermined adjustment in volume and/or internal pressure over time, a preselected volume profile can be obtained to accommodate changes in stomach size over the course of treatment with the device. The devices can be self-inflating (also referred to as automatic inflating) or inflatable (also referred to as manually inflating via a tether).

Volume-occupying devices and methods for manufacturing, deploying, inflating, tracking, locating, deflating and retrieving of such devices are provided. The devices and methods of the preferred embodiments may be employed for treating over weight and obese individuals. Methods employing the device of the preferred embodiments need not utilize invasive procedures, but rather the device may simply be swallowed by a patient, with or without a catheter attached. Once in the stomach of the patient, the device is inflated with a preselected gas or mixture of gases, to a preselected volume. The wall of the device is preselected for its particular gas diffusion properties. Once in the in vivo environment, the gas(es) within the device diffuse out through the wall of the device, and gases diffuse into the device from the in vivo environment. By preselecting the device wall and gas(es) initially employed to inflate the device, taking into account diffusion properties of gases into the device from the in vivo environment, the volume and/or internal pressure of the device can be maintained within a preselected range, or can follow a preselected profile of volume and/or pressure changes. After a predetermined time period, the device can be removed using endoscopic tools or will decrease in volume or deflate so as to pass through the remainder of the patient's digestive tract.

Inflation may be achieved by use of a removable catheter that initially remains in fluid contact with the device after it has been swallowed by the patient. Alternatively, inflation may be achieved by a self-inflation process, e.g., generation of gas in the device once it reaches the stomach by reaction of gas-generating components contained within the device upon swallowing, or by introduction of one or more components in the gas generating process into the device by use of a removable catheter.

The volume-occupying subcomponent of devices may be formed by injection, blow or rotational molding of a flexible, gas-impermeable, biocompatible material, such as, for example, polyurethane, nylon or polyethylene terephthalate. Materials that may be used to control the gas permeability/impermeability of the volume-occupying subcomponent include, but are not limited to, silicon oxide (SiOx), gold or any noble metal, saran, conformal coatings and the like, when it is desired to reduce permeability. To enhance gas-impermeable characteristics of the wall of the device, if desirable, the volume-occupying subcomponent may be further coated with one or more gas-barrier compounds, or be formed of a Mylar polyester film coating or kelvalite, silver or aluminum as a metalized surface to provide a gas impermeable barrier.

In further embodiments, the device employs a delivery state in which the device is packaged such that the device may be swallowed while producing minimal discomfort to the patient. In a delivery state, the device may be packaged into a capsule. Alternatively, the device may be coated with a material operable to confine the device and facilitate swallowing. Various techniques may also be employed to ease swallowing of the device including, for example, wetting, temperature treating, lubricating, and treating with pharmaceuticals such as anesthetics.

In other embodiments, the devices incorporate a tracking or visualization component that enables physicians to determine the location and/or orientation and/or state of the device within the patient's body using ultrasonic methods. Tracking subcomponents may incorporate materials that are responsive to ultrasonic energy. The device may be tracked and located using a complementary ultrasonic energy sensor that is responsive to the acoustic properties of the device. Such techniques may also be used to obtain certain device specific information and specifications while the device remains inside the patient's body, including but not limited to device location, orientation, size or state as it travels inside the body. The acoustically-responsive sensor outside the body can detect and process information related to the acoustic energy relayed by the internal device, which energy may be reflected off, created by, or otherwise propagated from the intragastric device or materials or objects in or on the intragastric device. This information can then be interpreted to identify the device's location, orientation, size and other attributes while still inside the body. An ultrasound system provides a simple, non-invasive and less harmful method of tracking, locating and characterizing intragastric devices.

DETAILED DESCRIPTION OF THE EMBODIMENTS

Figure 1:
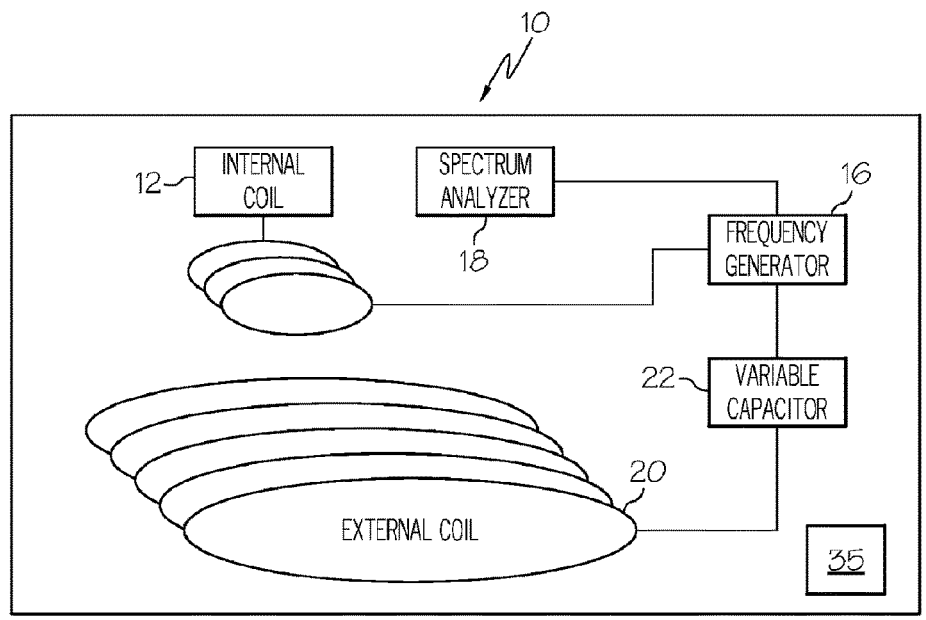
FIG. 1 depicts a system for locating or otherwise characterizing an intragastric device using ultrasound.

The following description and examples illustrate embodiments of the present invention in detail. Those of skill in the art will recognize that there are numerous variations and modifications of this invention that are encompassed by its scope. Accordingly, the description of a preferred embodiment should not be deemed to limit the scope of the present invention.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes. Degradation after a predetermined time, or within a predetermined window of time, after ingestion is particularly preferred.

The term "$CO_2$ barrier material" as used herein is a broad term, and is to be given its ordinary and customary meaning to a person of ordinary skill in the art (and is not to be limited to a special or customized meaning), and refers without limitation to a material having a permeability to $CO_2$ of 10 $cc/m^2/day$ or less under simulated in vivo conditions (100% humidity and body temperature of 37° C.). As used herein, the term "in vivo conditions" as used herein refers to both actual in vivo conditions, such as in vivo intragastric conditions, and simulated in vivo conditions. The permeability of a material to $CO_2$ may vary depending upon the conditions under which it is measured.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach via normal peristalsis movement. While the systems of preferred embodiments are swallowable, they are also configured by ingestion by methods other than swallowing. The swallowability of the system is derived, at least in part, by the outer container size for the self-inflating system and the catheter and outer container size for the manual inflation system. For the self-inflating system, the outer capsule is sufficient to contain the inner container and its constituents, an amount of activation agent injected prior to administration, the balloon size, and the balloon material thickness. The system is preferably of a size less than the average normal esophagus diameter.

Described herein is a system for an orally ingestible device with ultrasound locating and tracking of the device. In preferred embodiments, the device is able to traverse the alimentary canal. The device may be useful, for example, as an intragastric volume-occupying device. The device overcomes one or more of the above-described problems and shortcomings found in current intragastric volume-occupying devices.

In order to more clearly describe the subject matter of the preferred embodiments, different embodiments of the same subcomponent will be described under a single relevantly-titled subheading. This organization is not intended to limit the manner in which embodiments of different subcomponents may be combined in accordance with the present invention. The various subcomponents for use in the presently disclosed ultrasound locating system may be discussed under their respective subheaded sections or in any other section, including the section on the tracking and visualization subcomponent.

Swallowable Intragastric Balloon System

A swallowable, self-inflating or inflatable intragastric balloon system according to selected preferred embodiments includes the following components: self-sealing valve system for addition of fluid to the lumen of the balloon or to the inner container ("valve system"), a balloon in a deflated and compacted state ("balloon") and an outer capsule, container, or coating ("outer container") that contains the balloon. For self-inflating balloons, an inner capsule or other container ("inner container") that contains one or more $CO_2$ generating components is present inside the lumen of the balloon. For inflatable balloons, an inflation fluid source, a catheter, and tubing ("inflation assembly") are provided for inflating the balloon after ingestion or placement in the stomach. In the self-inflating balloon configuration, the valve is preferably attached to the inner surface of the balloon by an adhesive or other means (e.g., welding), and provided with an inoculation spacer to prevent puncture of the wall of the balloon and inner container by a needle or other means for injecting an liquid activation agent into the lumen of the balloon via the self-sealing valve. A valve providing releasable attachment of the tubing to the balloon is provided in the inflatable balloon configuration. Preferably, the self-sealing valve system attached to the balloon (e.g., on its inside surface) in the inflatable configuration is "universal" or compatible with a swallowable catheter or a physician-assisted catheter. The valve system serves to allow for balloon inflation using a miniature catheter that includes a needle assembly and also provides a mechanism for detachment of the catheter after inflation has been completed.

The outer container preferably incorporates the balloon in a compacted state (e.g., folded and rolled), preferably with sufficient space to allow for activation liquid to be injected into the balloon in the self-inflating balloon configuration, wherein the liquid activation agent initiates separation, erosion, degradation, and/or dissolution of the inner container and generation of $CO_2$ upon contact with the inflation agent contained within the inner container, which subsequently causes outer container separation, erosion, degradation, and/or dissolution due to $CO_2$ gas pressure. In the inflatable balloon configuration, the outer container need only incorporate the balloon in a compacted state.

Selected components of a swallowable intragastric balloon system of a preferred embodiment can include a silicone head with radioopacity ring, trimmed 30 D silicone septum, Nylon 6 inoculation spacer, compacted balloon, inner container (if self-inflating), and outer container as constituents of the system in unassembled form. A fully assembled outer container can include a vent hole aligned with a septum for puncture to inject liquid activation agent (if self-inflating) or a port for connection of tubing (if inflatable). As discussed further below, the components of particularly preferred systems possess the attributes described herein; however, in certain embodiments systems can be employed which utilize components having other attributes and/or values.

Devices according to the preferred embodiments are intended for ingestion by a patient and deployment without the need to resort to invasive methods. It is therefore desirable that the device of the preferred embodiments be operable to conform to a compact delivery state which can be swallowed by a patient with minimal discomfort. Once in the stomach, it is desirable for the device to assume a substantially larger deployed state. In order to achieve the transition from a delivery state to a deployed state the device is subjected to inflation.

Inner Container

In order to initiate inflation in the self-inflating configuration, the inflation subcomponent may require outside inputs such as an activation agent. The activation agent is preferably injected using a syringe having a needle with a gauge diameter of from 25 to 32. The needle length is preferably from about 0.25 inches (0.6 cm) to 1 inches (2.54 cm) in length so as to create a flow rate that allows for delivery of the full volume of inflation agent within 30 seconds, but in a manner/stream/flow that does not physically damage the inner container, thereby causing premature $CO_2$ generation and inflation. The activation agent is preferably pure water, or a solution containing up to 50% concentration of anhydrous citric acid at 20° C., or the equivalent thereof at varying solution temperatures based on solubility of anhydrous citric acid. Preferably, the system is configured to have an occupyable void space in the central lumen of the balloon when in compacted form in the outer container of from about 0.3 ml to about 4.5 ml, such that a corresponding volume of activation agent can be injected into the void space.

In one embodiment, prior to folding, the free-floating inner container with inflation agent for $CO_2$ generation is preferably vertically aligned with the self-sealing valve system such that the septum/inoculation spacer is placed directly above the tip of the capsule. The balloon contains an inner container. A self-sealing valve system is adhesively adhered to the interior of the wall of the balloon, and the inverted configuration of the balloon is provided by inversion through a hole sealed with a patch. The top approximate ¼ of the balloon wall is folded over the inner capsule, and the pleats where the capsule is are creased similar to the pleats formed in the second step of making a paper airplane, then folded over to the left or to the right. The bottom approximate ¾ of the sphere is then accordioned using no more than 2 creases and folded over the capsule. The left half is then folded over the right half of the capsule or vice versa so that the wings touch. Then the material is rolled over until it creates a tight roll. The device is then placed inside the outer container.

In a self-inflating configuration, the balloon is folded so as to form a pocket around the inner capsule, to insure that the liquid injected through the self-sealing valve system is contained in an area less than 10% of the entire balloon surface area. It is not necessary to provide a pocket in the inflatable configuration, as no inner capsule is provided. The balloon is folded such that the number of total folds is minimized so as to minimize possible damage to the outer material or compromise of barrier properties. The number of total folds is preferably less than 10 folds. The balloon material is rolled when at all possible such that the number of creases required to fit the balloon in an outer container is minimized. This is done in effort to also to prevent lumen material damage. The self-sealing valve is also preferably constructed off-center of the balloon so as to minimize the number of folds that layer on top of each other.

In the self-inflating configuration, the material forming the wall of the balloon is processed and folded to maximize reaction efficiency by localizing the initiation agent injected into the balloon so that it is maintained proximal to the reactants within the inner container. The balloon is folded such that once the reaction initiates and the outer container separates, the balloon unfolds in a manner that creates the largest possible surface area, which prohibits the balloon from readily passing through the pyloric sphincter. The ratio of reactants in the inflation agent and activation agent are selected such that the pH of any remnant liquid inside the lumen of the balloon is acidic, with a pH of less than 6, such that any balloon leakage or breach that allows stomach acid to enter does not cause additional $CO_2$ generation and resulting unintentional re-inflation.

In a self-inflating configuration, an inflation agent is compressed, formed or otherwise held in a shape which provides good surface area availability for the reactants for $CO_2$ generation, while minimizing the space and/or volume sufficient to hold the inner container. Preferably, the inner container has a length (longest dimension) of from about 0.748 inches (1.9 cm) to 1.06 inches (2.7 cm) and a diameter or width of from about 0.239 inches (0.6 cm) to about 0.376 inches (1 cm). The volume of the inner container is preferably from about 0.41 ml to about 1.37 ml. The inner container is preferably in the form of a standard push-fit gelatin capsule but a gelatin tape may be used in lieu of a push-fit capsule. The container is preferably relied upon for containing the inflation agent; however, additional sealing or other encapsulation can be employed to control timing of inflation. Gelatin is particularly preferred for use as the inner container; however other materials can also be suitable for use, e.g., cellulose. In order to minimize the internal volume of the system, it is generally preferred to include only a single inner container; however, in certain embodiments two or more internal containers can advantageously be employed. Timing of self-inflation is selected based on a normal esophageal transit time and a normal time of gastric emptying of large food particles, such that the balloon does not inflate to a size that can block the esophageal passageway or prematurely pass through the pyloric sphincter. Timing is also controlled by compacting the balloon such that the activation agent is substantially localized in the balloon next to the inner capsule, creating an efficient $CO_2$ self-inflation method. Balloon inflation is initiated by the liquid activation agent causing degradation of the inner container, such that the inflation agent in the inner container contacts the liquid activation agent, thereby initiating the gas generation reaction.

Inflation Assembly

In certain preferred embodiments, the volume-occupying subcomponent is filled with a fluid using tubing which is subsequently detached and pulled away from the volume-occupying subcomponent. One end of the volume-occupying subcomponent has a port connected to tubing of sufficient length that when unwound can span the entire length of the esophagus, from mouth to stomach. This tubing is connected to the volume-occupying subcomponent with a self-sealable valve or septum that can tear away from the volume-occupying subcomponent and self-seal once the volume-occupying subcomponent is inflated. A physician or other health care professional secures one end of the tubing as the patient swallows the device. Once the device is residing within the stomach, the physician uses the tube to transmit a fluid, such as air, other gas(es), saline solution, pure water, or the like, into the volume-occupying subcomponent and thereby inflate it. After the volume-occupying subcomponent is fully inflated, the tubing is released and can be pulled out from inside the patient.

The tube may be released in a number of manners. For example, the tubing may be detached by applying a gentle force, or tug, on the tubing. Alternatively, the tubing may be detached by actuating a remote release, such as a magnetic or electronic release. Additionally, the tubing may be released from the volume-occupying subcomponent by an automatic ejection mechanism. Such an ejection mechanism may be actuated by the internal pressure of the inflated volume-occupying subcomponent. For example, the ejection mechanism may be sensitive to a specific pressure beyond which it will open so as to release any excess pressure and simultaneously release the tube. This embodiment provides a desirable feature through combining release of the tubing with a safety valve that serves to avert accidental over inflation of the volume-occupying subcomponent in the patient's stomach.

This automatic release embodiment also provides the benefit that the device inflation step may be more closely monitored and controlled. Current technology allows for a self-inflating intragastric volume-occupying subcomponent which generally begins to inflate in a four minute timeframe after injection with an activation agent such as citric acid. In this approach, the volume-occupying subcomponent may, in some instances, begin to inflate prior to residing within the stomach (e.g., in the esophagus), or, in patients with gastric dumping syndrome or rapid gastric emptying, the volume-occupying subcomponent may end up in the small intestine prior to the time that inflation occurs. Accordingly, in certain embodiments it can be desirable to inflate the volume-occupying subcomponent on command, once it is ascertained that the volume-occupying subcomponent is residing in the correct location.

In certain embodiments, it may also be advantageous for the volume-occupying subcomponent to inflate gradually or in several steps over time, or for the volume-occupying subcomponent to maintain a volume and/or internal pressure within a preselected range. For example, if gas escapes the volume-occupying subcomponent prior to the desired deflation time, it can be beneficial for the device to re-inflate in order to preserve it in its expanded state.

Outer Container

The balloon is preferably provided in a deflated and folded state in a capsule or other retaining, containing or coating structure ("outer container"). The outer container is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container; however other materials can also be suitable for use, e.g., cellulose, collagen, and the like. Preferably, the outer container has a length (longest dimension) of from about 0.95 inches (2.4 cm) to 2.5 inches (6.3 cm) and a diameter or width of from about 0.35 inches (0.9 cm) to about 0.9 inches (2.4 cm). The volume of the inner container is preferably from about 1.2 ml to about 8.25 ml. In the self-inflating configuration, the outer container is preferably configured with one or more holes, slits, passageways or other egresses, preferably on each end, which act as vents such that any gas created due to inflation agent exposure to condensation or other ambient moisture present during processing does not cause premature separation or degradation of the inner container prior to 30 seconds after inoculation of the liquid activation agent, which may have an undesirable effect on reaction efficiency. Such egresses can also expedite dissolution of the outer container to prepare the balloon for inflation in the inflatable configuration. The process of the outer capsule degrading (e.g., separates, dissolves, or otherwise opens) is expedited by pressure build up caused by inflation (self-inflation or inflation via catheter) of the balloon. The outer capsule can be dipped in water for a brief time to soften the materials but not release the balloon prior to swallowing to minimize the time lapse between swallowing and balloon inflation. In the inflatable configuration, the outer container is provided with a hole to house the inflation tube needle assembly, wherein the diameter of the catheter needle housing is mechanically compatible with the diameter of the outer container hole such that the needle can be inserted into the self-sealing valve while maintaining therein the housed balloon to facilitate pushing or swallowing of the balloon assembly. In a preferred embodiment, the outer container is a capsule. The distal half of the capsule may be flared to prevent abrasion of the balloon materials by the leading edge of the capsule as the compacted balloon is inserted into the capsule. The capsule can also comprise two parts held together with a gel band and encompassing the folded balloon that allows for quicker separation of the capsule so that inflation can take place more expeditiously. The outer capsule degrades (e.g., separates, dissolves, or otherwise opens) due to contact with ingested fluid ingestion (e.g., water intake) and preferably degrades within 5 minutes or less, more preferably within 2 minutes or less, so as not to cause discomfort to the patient while the balloon/catheter tube is in place.

In a preferred embodiment, the device is fitted into a standard sized gelatin capsule. The capsule may be formed of a material that has a known rate of degradation such that the device will not be released from the capsule or otherwise deployed prior to entry into the stomach. For example, the capsule materials may include one or more polysaccharide and/or one or more polyhydric alcohols.

Alternatively, the device, in its delivery state, may be coated in a substance that confines the device in its delivery state while also facilitating swallowing. The coating may be applied by a dipping, sputtering, vapor deposition, a spraying process which may be conducted at an ambient or positive pressure, a gelling process, or any other deposition processes. The coating can include a deformable or shapeable coating configured to ease swallowing of the device.

In certain preferred embodiments, the encapsulated or coated device is lubricated or otherwise treated so as to facilitate swallowing. For example, the encapsulated or coated device may be wetted, heated, or cooled, prior to swallowing by the patient. Alternatively, the encapsulated or coated device may be dipped in a viscous substance that will serve to lubricate the device's passage through the esophagus. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the coating or capsule is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule may be weighted at a certain end in order for it to be oriented appropriately when it is administered, as it travels down the esophagus, and/or when it is in the stomach. The weighting components may include polymer materials or inflation reactants.

The swallowable, self-inflating intragastric balloon is provided with mechanisms to reliably control timing of self-inflation such that premature inflation while in the esophagus during swallowing is avoided and sufficient inflation once in the stomach so as to prevent passage through the pyloric sphincter is ensured. Normal esophageal transit time for large food particles has been documented as 4-8 seconds, and gastric emptying of large food particles through the pylorus does not occur for at least 15-20 minutes. The outer container is preferably configured to separate, dissolve, degrade, erode, and/or otherwise allow the deflated/folded balloon to begin unfolding not less than 60 seconds but not more than 15 minutes after inoculation with liquid activation agent. The inner container is preferably configured chemically, mechanically or a combination thereof to retard the initial $CO_2$ generating chemical reaction such that sufficient $CO_2$ to begin inflating the balloon is not available earlier than 30 seconds after inoculation with the liquid activation agent, but to permit generation of sufficient $CO_2$ such that at least 10% of the occupyable volume of the balloon is filled within 30 minutes, at least 60% of the occupyable volume of the balloon is filled within 12 hours, and at least 90% of the occupyable volume of the balloon is filled within 24 hours. This timing allows for injection of the activation agent into the outer container by the medical professional, passing the device to the patient, and swallowing by normal peristaltic means by the patient. This timing also prohibits potential passing of an uninflated balloon into the duodenum by the balloon being inflated to a sufficient size such that gastric emptying of the balloon cannot be easy, as objects more than 7 mm in diameter do not readily pass.

Delivery Components

It certain embodiments, it may advantageous for an administrator of the device to use a delivery tool for delivering the device to the mouth or facilitating its passage through the esophagus in the optimal orientation. A delivery tool may enable the device administrator to inject the device with one or more inflation agents or inflation gases as part of administering the device to the patient. In a preferred embodiment, such injection may be accomplished in the same mechanical action(s) of the administrator that are employed to release the device from the delivery tool into the mouth or esophagus. For example, the delivery tool may include a plunger, a reservoir containing a fluid, and an injection needle. The administrator pushes the plunger which, either in sequence or approximately simultaneously, forces the injection needle into the device and thereby injects the liquid contained in reservoir into the device. Subsequent application of force to the plunger pushes the device out of the delivery tool and into the desired location within the patient. Furthermore, the delivery tool may also include a subcomponent that administers an anesthetic or lubricant into the patient's mouth or esophagus to ease the swallowability of the device.

Balloon

The volume-occupying subcomponent ("balloon") of the preferred embodiments is generally formed of a flexible material forming a wall which defines an exterior surface and an interior cavity. Various of the above-described subcomponents may be either incorporated into the wall or interior cavity of the volume-occupying subcomponent. The volume-occupying subcomponent can vary in size and shape according to the patient's internal dimensions and the desired outcome. The volume-occupying subcomponent may be engineered to be semi-compliant, allowing the volume-occupying subcomponent to stretch or expand with increases in pressure and/or temperature. Alternatively, in some embodiments, a compliant wall offering little resistance to increases in volume may be desirable.

Spherical volume-occupying subcomponents are preferred in certain embodiments. Alternatively, the volume-occupying subcomponent may be constructed to be donut-shaped, with a hole in the middle of it, and may be weighted and shaped in such a way that it orients in the stomach to cover all or part of the pyloric sphincter, similar to a check valve. The hole in the middle of the volume-occupying subcomponent can then serve as the primary passage for the contents of the stomach to enter the small intestine, limiting the passage of food out of the stomach and inducing satiety by reducing gastric emptying. Volume-occupying subcomponents may be manufactured with different-sized donut-holes according to the degree that gastric emptying is desired to be reduced. Delivery, inflation and deflation of the volume-occupying subcomponent may be accomplished by any of the methods described above.

It is advantageous for the volume-occupying subcomponent wall to be both high in strength and thin, so as to minimize the compacted volume of the device as it travels the esophagus of the patient. In certain embodiments, the volume-occupying subcomponent wall materials are manufactured with a biaxial orientation that imparts a high modulus value to the volume-occupying subcomponent.

In one embodiment, the volume-occupying subcomponent is constructed of a polymeric substance such as polyurethane, polyethylene terephthalate, polyethylene naphthalate, polyvinyl chloride (PVC), Nylon 6, Nylon 12, or polyether block amide (PEBA). The volume-occupying subcomponent may be coated with one or more layers of substances that modify (increase, reduce, or change over time) gas-barrier characteristics, such as a thermoplastic substance.

Preferably, the gas-barrier materials have a low permeability to carbon dioxide or other fluids that may be used to inflate the volume-occupying subcomponent. The barrier layers should have good adherence to the base material. Preferred barrier coating materials include biocompatible poly(hydroxyamino ethers), polyethylene naphthalate, polyvinylidene chloride (PVDC), saran, ethylene vinyl alcohol copolymers, polyvinyl acetate, silicon oxide (SiOx), acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent include metals such as silver or aluminum. Other materials that may be used to improve the gas impermeability of the volume-occupying subcomponent include, but are not limited to, gold or any noble metal, PET coated with saran, conformal coatings and the like, as listed, for example, in Tables 1a-b.

In certain preferred embodiments, the volume-occupying subcomponent is injection, blow or rotational molded. Either immediately following such molding, or after a period of curing, the gas-barrier coating may be applied if not already applied within the composite wall.

In another embodiment, the intragastric volume-occupying subcomponent is formed using a Mylar polyester film coating silver, aluminum or kelvalite as a metalized surface, to improve the gas impermeability of the volume-occupying subcomponent.

In the event that the volume-occupying subcomponent's wall is composed of multiple layers of materials, it may be necessary to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent. Accordingly, it may be advantageous to include as an additional layer in the volume-occupying subcomponent certain materials that seal. For example, a volume-occupying subcomponent comprised of a combination of PET and SiOx layers, which impart favorable mechanical and gas impermeability characteristics to the volume-occupying subcomponent, may be sealed by including a layer of sealable polyethylene in such volume-occupying subcomponent.

According to another embodiment of the preferred embodiments, the functionality of the volume-occupying subcomponent and the deflation component is combined either in part or in whole. For example, the volume-occupying subcomponent may be formed of a substance that is degraded within the stomach over a desired period of time. Once the degradation process has formed a breach in the wall of the volume-occupying subcomponent, the volume-occupying subcomponent deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent into the desired delivery state. For example, the evacuation of air from the volume-occupying subcomponent may be actuated by vacuum or mechanical pressure (e.g. rolling the volume-occupying subcomponent). In certain embodiments, it is desirable to minimize the number of creases produced in the volume-occupying subcomponent when in the delivery state.

Deflation and/or inflation of the volume-occupying subcomponent may be achieved through one or more injection sites within the wall of the volume-occupying subcomponent. For example, two self-sealing injection sites can be incorporated at opposite sides of the volume-occupying subcomponent. The volume-occupying subcomponent may be positioned within a fixture that employs two small-gauge needles to evacuate the air from the volume-occupying subcomponent.

In one embodiment, the self-sealing injection sites may further be used to insert chemical elements of the inflation subcomponent into the interior of the volume-occupying subcomponent. After injection of the chemical elements into the volume-occupying subcomponent, the same needles may be used to perform evacuation of the volume-occupying subcomponent.

It may be desirable that the volume-occupying subcomponent is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties can, for example, be advantageous if deflation of the volume-occupying subcomponent were initiated by a tearing or puncturing of the volume-occupying subcomponent wall, since such initial tear or puncture may then increase in scope, hastening and/or maximizing the deflation process.

The volume-occupying subcomponent may also be coated by a lubricious substance that facilitates its passage out of the body following its deflation. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may be applied by a dipping, sputtering, vapor deposition or spraying process which may be conducted at an ambient or positive pressure.

The balloon composite wall materials can be of similar construction and composition as those described in U.S. Patent Publication No. 2010-0100116-A1, the contents of which is hereby incorporated by reference in its entirety. The materials are able to contain a fluid, preferably in compressed or non-compressed gas form, such as, e.g., $N_2$, Ar, $O_2$, $CO_2$, or mixture(s) thereof, or atmospheric air (composed of a mixture of $N_2$, $O_2$, Ar, $CO_2$, Ne, $CH_4$, He, Kr, $H_2$, and Xe) that simulate gastric space concentrations. In certain embodiments, the balloon is able to hold the fluid (gas) and maintain an acceptable volume for up to 6 months, preferably for at least 1 to 3 months after inflation. Particularly preferred fill gases include non-polar, large molecule gases that can be compressed for delivery.

Prior to placement in the outer container, the balloon is deflated and folded. In the inverted configuration in a deflated state, the balloon is flat, with the inverted seam extending around the perimeter of the balloon. The self-sealing valve system is affixed to the inner wall of the lumen close to the center of the deflated balloon, with the inner container positioned adjacent to the self-sealing valve system. The walls of the balloon are then folded. As part of the balloon design, the self-sealing valve system is manufactured in a manner such that it is placed "off center" to minimize the number of folds upon themselves (e.g., doubling or tripling up) required to fit the balloon in the outer container. For example, the self-sealing valve system can advantageously be placed ½ r±¼ r from the center of the balloon, wherein r is the radius of the balloon along a line extending from the center of the balloon through the septum.

Valve System

In preferred embodiments, a self-sealing valve system which contains a self-sealing septum housed within a metallic concentric cylinder is provided. In the inflatable configuration, the self-sealing valve system is preferably adhered to the underside of the balloon material such that only a portion of the valve protrudes slightly outside of the balloon surface to ensure a smooth surface. The valve system for the inflatable configuration can utilize the same self-sealing septum designed for the self-inflating configuration. The septum preferably consists of a material possessing a durometer of 20 Shore A to 60 Shore D. The septum is inserted or otherwise fabricated into the smaller cylinder of the concentric metallic retaining structure that is preferably cylindrical in shape. The smaller cylinder within the larger cylinder controls alignment of the catheter needle sleeve/needle assembly with the septum, provides a hard barrier so that the catheter needle does not pierce the balloon material (needle stop mechanism), and provides compression such that the valve/septum re-seals after inflation and subsequent needle withdrawal.

The concentric valve system can also provide radio opacity during implantation and is preferably titanium, gold, stainless steel, MP35N (nonmagnetic, nickel-cobalt-chromium-molybdenum alloy) or the like. Non-metallic polymeric materials can also be used, e.g., an acrylic, epoxy, polycarbonate, nylon, polyethylene, PEEK, ABS, or PVC or any thermoplastic elastomer or thermoplastic polyurethane that is fabricated to be visible under x-ray (e.g., embedded with barium).

The septum is preferably cone shaped, so that the compressive forces are maximized for self-sealing after inflation. The self-sealing septum allows air to be evacuated from the balloon for processing/compacting and insertion into the outer container, and allows for piercing by an inflation agent syringe needle (self-inflating configuration) or inflation catheter needle (inflatable configuration), and then subsequent withdrawal of the inflation agent syringe needle or detachment of the inflation catheter and withdrawal of the catheter needle significantly limiting gas leakage outside of the balloon during the inflation process and needle withdrawal/catheter detachment. The septum is inserted into the valve using a mechanical fit mechanism to provide compression. An additional ring can be placed at the distal end of the inner cylinder to provide additional compression to ensure the septum material is dense enough to re-seal itself. The ring is preferably metallic in nature, but can also be a non-metallic polymeric material such as an acrylic, epoxy, or thermoplastic elastomer or thermoplastic polyurethane. The ring material is preferably the same material as the cylinder, titanium, but can also be gold, stainless steel, MP35N or the like.

In the inflatable configuration, a larger, outer cylinder of the concentric valve housing contains a slightly harder durometer material than the inner cylinder (50 Shore A or greater), but is also preferably silicone. The purpose of using a harder durometer material is to ensure sealing when connected to the needle sleeve for inflation. The silicone located in the outer ring of the concentric valve is adhered to the balloon from the inside surface. The entire outer cylinder is filled and a small circular lip of this same material is provided that is slightly larger than the diameter of the inner cylinder and extends to the outside surface of the balloon. The lip is compatible with the bell shaped needle sleeve and provides sealing to enhance connection of the valve to the catheter to withstand the inflation pressures applied and also increases the tensile force of the catheter. This silicone lip preferably does not protrude past the balloon surface more than 2 mm to ensure that the balloon surface remains relatively smooth and does not cause abrasion or ulcerations of the mucosa. It is designed to provide compressive forces against the needle sleeve of the catheter for inflation and detachment whereby when connected to the needle sleeve of the inflation catheters, the connection force during the inflation process can withstand up to 35 PSI. The seal is then broken during detachment using hydrostatic pressure that is more than 40 PSI less than 200 PSI to break the connection force. Two additional retaining rings, preferably made of the same material as concentric valve, are included in the valve system to further enhance the seal between the metal and the valve silicone and provide additional mechanical support to ensure proper mechanical fit and are intended to disrupt slippage of the silicone material from the hard (metallic) valve system (causing an increase in tensile force).

The valve structure for the inflatable configuration uses a mechanical fit mechanism to provide the functions of the self-sealable valve for inflation by the catheter and subsequent catheter detachment; however, primer and/or adhesive may be used to provide additional support in maintaining the assembly. The configuration can be modified by modifying the surfaces of the metal components, making them more sticky or slippery to provide the desired mechanical/interference fit. The interference fit between the valve and the catheter can be modified to change the pressure requirements for inflation and/or detachment. Additional assemblies can include overmolding the metallic portions or the concentric system in silicone such that additional support rings to ensure the mechanical fit and the tensile strength and forces required to sustain the assembly during catheter inflation and detachment can be omitted.

The total valve diameter in the inflatable configuration is designed to fit a miniature catheter system that does not exceed 8 French (2.7 mm, 0.105 inches) in diameter. The total diameter does not exceed 1 inch (2.54 cm) and is preferably less than 0.5 inches (1.27 cm), to facilitate swallowing. Additional valves can be added, if desired; however, it is generally preferred to employ a single valve so as to maintain the volume of the deflated/folded balloon (and thus the outer container dimensions) as small as possible. The valve system is preferably attached to the inner surface of the balloon such that a shear force greater than 9 lbs (40 N) is required to dislodge the valve system.

In a self-inflating configuration, the valve system can be attached to the balloon (e.g., on its inside surface) without the use of an opening, orifice, or other conduit in the wall of the balloon. The valve system can utilize a septum with a durometer of 20 Shore A to 60 Shore D. The valve can be inserted or otherwise fabricated into a retaining structure that has a higher durometer, e.g., 40 Shore D to 70 Shore D or more. The retaining structure can be fabricated from a silicone, rubber, soft plastic or any suitable non-metallic polymeric material such as an acrylic, an epoxy, a thermoplastic elastomer, or thermoplastic polyurethane. Preferably, a structure, such as a ring, that can be metallic or non-metallic but radiopaque (e.g., barium) and visible under X-ray, can be embedded in the retaining structure. Using a mechanical fit mechanism of two structures of different durometers, one softer (septum) with a large diameter, can be inserted into a snug, more rigid durometer structure creates compressive forces in the once open orifice to enable $CO_2$ retention and reduce susceptibility for $CO_2$ gas leaks. The metallic ring for radio-opacity also helps to create compressive forces on the septum. The self-sealing septum allows air to be evacuated from the balloon for processing/compacting and inserting in the outer container, and also allows for the inflation agent to be injected into the outer container for inflation initiation. Additional septums can be provided, if desired; however, it is generally preferred to employ a single septum so as to maintain the volume of the deflated/folded balloon (and thus the outer capsule) as small as possible. The valve system is preferably attached to the inner surface of the balloon such that a shear force greater than 9 lbs (40 N) is required to dislodge the valve system. A silicone head and opacity ring of a self-sealing valve system can be employed, as can a wedge-shaped septum.

In the self-inflating configuration, an inoculation spacer is preferably incorporated to guide a needle into the self-sealing valve for injection of liquid activation agent into the lumen of the balloon and to prevent the needle from penetrating the wall of the deflated/folded balloon elsewhere such that pressure within the lumen of the balloon cannot be maintained. The inoculation spacer also facilitates preventing liquid activation agent from penetrating the inner container or the folded balloon material, thereby focusing the activation agent in an appropriate manner to properly mix the reactants for $CO_2$ generation according to the criteria described above. The inoculation spacer is generally in the form of a tube or cylinder. The inoculation spacer is preferably attached to the inner container and/or the self-sealing valve system with an adhesive or other fixing means; however, in certain embodiments the inoculation spacer can be "free-floating" and maintained in position by the folding or rolling of the walls of the balloon. The inoculation spacer can comprise any suitable material that can be passed after separation, erosion, degradation, digestion, and/or dissolution of the outer container; however, preferable materials include non-metallic materials with a minimum Shore D durometer of 40 or more, any metallic material, or a combination thereof. A cupped needle stop (inoculation spacer) can be employed in preferred embodiments.

Balloon

In a preferred embodiment, a self-inflating balloon is fully sealed 360 degrees around. In the self-inflating configuration, with injection of an inflation agent by needle syringe, there are preferably no external openings or orifices to the central lumen. In the inflatable configuration, a valve structure (either protruding, recessed, or flush with the surface of the balloon) is provided for providing an inflation fluid to the central lumen. The balloon can have a "noninverted," "inverted," or "overlapped" configuration. In a "noninverted" configuration, the seams or welds and seam allowance, if any, are on the outside of the inflated balloon. In an "overlapped" configuration, layers are overlapped, optionally with one or more folds, and secured to each other via welds, a seam, adhesive, or the like, resulting in a smooth external surface. In an "inverted" configuration, the balloon has a smooth external surface with seams, welds, adhesive bead, or the like inside the inflated balloon. In order to create a balloon with an inverted configuration, e.g., a balloon with no external seam allowance (no wall material between the edge of the balloon and the weld, seam, or other feature joining the sides together), two balloon halves are joined together in some fashion (e.g., adhered using adhesive or heat or the like based on the balloon material used). One of the balloon halves encompasses an opening to allow for the balloon to be pulled through itself after adherence of the two halves and to have the seams of the balloon on the inside. The opening created is preferably circular but can be any similar shape, and the diameter of the opening preferably does not exceed 3.8 cm; however, in certain embodiments a larger diameter may be acceptable. A patch of material is adhered (adhesively, heat welded, or the like, based on the material used) to cover the original balloon-half opening. The inversion hole thus created that is subsequently patched is small enough that the forces exerted during inflation do not compromise the material used to maintain fluid in the balloon. The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 $cm^3$ to 350 $cm^3$ (at 37° C. and at internal nominal pressure and/or full inflation), an internal nominal pressure (at 37° C.) of 0 psi (0 Pa) to 15 psi (103421 Pa), and a weight of less than 15 g. The self-inflating balloon is configured for self-inflation with $CO_2$ and is configured to retain more than 75% of the original nominal volume for at least 25 days or more, or at least 30 days, preferably for at least 90 days when residing in the stomach. The inflatable balloon is configured for inflation with an appropriate mixture of gases so as to deliver a preselected volume profile over a preselected time period (including one or more of volume increase periods, volume decrease periods, or steady state volume periods).

The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 $cm^3$ to 350 $cm^3$ (at 37° C. and at internal nominal pressure and/or full inflation), an internal nominal pressure (at 37° C.) of 0 psi (0 Pa) to 15 psi (103421 Pa), and a weight of less than 15 g. In certain embodiments wherein a stable volume over the useful life of the device is preferred, the balloon is configured to maintain a volume of 90% to 110% of its original nominal volume. In other embodiments, it can be desirable for the balloon to increase and/or decrease in volume over its useful life (e.g., in a linear fashion, in a stepwise fashion, or in another non-linear fashion). In other embodiments, the balloon maintains a volume of 75% to 125% of its original nominal volume, or 75% to 150%

The intragastric device can be a single free-floating or tethered device. In some embodiments, it can be desirable to provide multiple devices (2, 3, 4, 5, 6, or more), either free-floating or tethered to each other, e.g., in a similar configuration to a cluster of grapes. The individual devices can be simultaneously inflated with one inflation system connected to all of the devices, or each device can be provided with a separate inflation system.

Inner Container

The inner container for the self-inflating balloon is contained within the lumen of the balloon and contains the $CO_2$ generator for balloon self-inflation. The $CO_2$ generator comprises an inflation agent mixture housed within the container. Preferably, from about 10% to about 80% of the total inflation agent used comprises powdered citric acid, with the remainder comprising powdered sodium bicarbonate. Sufficient inflation agent is provided such that upon completion of the $CO_2$ generating reaction, the balloon achieves inflation at the nominal inflation pressure described above. Preferably, a total of from about 0.28 to 4 grams inflation agent mixture is employed, depending upon the balloon size to be inflated; preferably up to 1.15 grams of sodium bicarbonate is used with the remainder being powdered citric acid to generate 300 $cm^3$ of $CO_2$ at nominal pressure.

Inflation Assembly

An intragastric balloon system that is manually inflated by a miniature catheter can be employed in certain embodiments. The system preferably remains "swallowable." The balloon for delivery is in a compacted state and is attached to a flexible, miniature catheter, preferably no larger than 4 French (1.35 mm) in diameter. The catheter is designed such that a portion of the catheter can be bundled or wrapped upon itself for delivery with the encapsulated balloon, allowing the patient to swallow both catheter and balloon for delivery to the stomach. The balloon can contain a self-sealable valve system for attachment of the catheter and inflation of the balloon once it reaches the stomach cavity. The proximal end of the catheter can be left just outside of the patient's mouth, permitting connection to an inflation fluid container that can house the preferred inflation fluid (gas or liquid). After inflation the catheter can be detached from the balloon valve and pulled back through the mouth. This method allows for the intragastric balloon to maintain its swallowability but allow for inflation by a fluid source or a mixture of fluid sources via the catheter. Alternatively, a more rigid, pushable system can be employed wherein the balloon valve is compatible with either the swallowable, flexible catheter or the pushable, rigid catheter assembly.

The inflation catheters (swallowable or administrator-assisted pushable) described herein are configured to deliver the balloon device orally and without any additional tools. The administration procedure does not require conscious sedation or other similar sedation procedures or require endoscopy tools for delivery. However, other versions of the device can be used in conjunction with endoscopy tools for visualization or can be adapted such that the balloon device can be delivered nasogastrically as well.

In operation, the proximal end of the inflation catheter is connected to a valve or connector that allows for connection to the inflation source or the disconnect source, this is preferably a Y-arm connector or inflation valve. The connector materials may consist of polycarbonate or the like and can connect to a single or multi-lumen catheter tube. The distal end of the inflation catheter is connected to the universal balloon valve of the balloon that has been compacted and housed within a gelatin capsule or compacted using gelatin bands. The catheter tube is preferably from 1 French (0.33 mm) to 6 French (2 mm) in diameter. The catheter is preferably long enough to extend out past the mouth (connected to the inflation connector or valve) and transverse the esophagus down to at least the middle of the stomach—approximately 50-60 cm. Measurement ticks can be added to the tubing or catheter to aid in identifying where the end of the tube is located. Timing for inflation can be initiated by having the tube contain a pH sensor that determines a location difference between the esophagus (pH 5-7) and the stomach (pH 1-4) based on the different pH between the two anatomical sources, or can be derived or verified from the expected pressure in a contained (i.e., esophagus) versus a less-constrained space (i.e., stomach). The tube can also contain nitinol that has a tunable transmission to the body temperature, taking into account the timing for swallowing. The tube can also be connected to a series of encapsulated or compacted balloons on a single catheter. Each can be inflated and released separately. The number of balloons released can be tune-able to the patient's needs and desired weight loss.

In certain embodiments, a catheter with the balloon at the distal end (inflated with air) is employed to temporarily and firmly hold the balloon in place. A small deflated balloon catheter can be positioned through the head of the gastric balloon (e.g., a "balloon within the balloon"), and then inflated with air during delivery to firmly hold the capsule and balloon in place and prevent spontaneous detachment of balloon from the catheter. This balloon catheter can incorporate a dual channel that can also allow the bigger gastric balloon to be inflated (by gas or liquid). Once the gastric balloon has been satisfactorily inflated, the small air balloon catheter can be deflated and pulled out of the valve (allowing the valve to self-seal), and out of the body, leaving the inflated gastric balloon in the stomach.

In other embodiments, the catheter may be coated to enhance swallowability or is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

Dual Lumen Catheter

In a preferred embodiment, a swallowable dual lumen catheter is provided. The dual lumen catheter has two lumens with a diameter of the complete assembly no larger than 5 French (1.67 mm), preferably no larger than 4 French (1.35 mm). The inner lumen preferably does not exceed 3 French (1 mm) and functions as the inflation tube, and the outer lumen preferably does not exceed 5 French (1.67 mm) and functions as the disconnection tube; the inner and outer lumen do not exceed 2 French (0.66 mm) and 4 French (1.35 mm), in diameter, respectively. The catheter assembly is connected to a needle assembly, described in more detail below, at the distal end and to a dual port inflation connector at the proximal end. The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible and have moderate tensile strength and a significant amount of hoop strength to handle applied pressures. The lumens are preferably round and co-axial and free-floating so as to provide flexibility. The dual lumen assembly also preferably requires no adhesive or glue. Alternative lumen configurations can include two D-lumens or a combination of a D-lumen and round lumen, and can be used in stiffer configurations of the final catheter assembly. Preferred materials for the tubing include a thermo-resistant polyethylene tubing such as PEBAX® or a thermo-resistant polyurethane tubing such as PELLETHANE™, PEEK or Nylon. The tubing can also be manufactured out of bioresorbable materials such as polylactic acid (PLA), poly-L-aspartic acid (PLAA), polylactic/glycolic acid (PLG), polycaprolactone (PCL), DL-lactide-co-ε-caprolactone (DL-PLCL) or the like, wherein the tube can be released after inflation and detachment and swallowed as normal.

At the distal end of the catheter assembly, the inner lumen or inflation tube is attached to the needle assembly that is used to puncture the balloon's self-sealing valve, preferably located at one of the apexes of the balloon housed inside of a gelatin capsule as outer container. The outer lumen is connected to the needle sleeve and provides connection force between the catheter assembly and balloon providing the tensile strength to withstand balloon inflation pressures, e.g., pressures of up to 10 psi or higher, while maintaining the assembly together. The needle sleeve is configured to mechanically couple with the balloon valve assembly. The needle is preferably made of metal, preferably stainless steel or the like, with a maximum size of 25 gauge (0.455 mm), preferably no smaller than 30 gauge (0.255 mm) for inflation timing purposes. The needle sleeve is preferably a soft material such as nylon or the like, or can also be polycarbonate, polyethylene, PEEK, ABS or PVC. The needle sleeve covers the length of the needle in its entirety, such that the body is protected from the needle and the needle can only pierce the balloon septum. Preferably the needle sleeve is flush or extends out slightly more than the needle length. The needle is inserted into the balloon septum prior to swallowing and maintains a retention force of approximately 0.33 lb (0.15 kg) when coupled to the silicone area of the balloon valve. The needle sleeve is preferably slightly bell shaped or contains a circular relief or lip so that when inserted into the silicone area of the valve a lock and key mechanism is created to increase the tensile strength of the assembly and enhance the sealing for inflation.

At the proximal end, the catheter assembly is connected to a Y-adapter assembly preferably made of polycarbonate. The y-adapter is "keyed" so that the inflation gas and connection fluid are connected to the catheter assembly appropriately and travel down the correct lumen.

Prior to inflation, priming of the disconnection lumen may be employed using a liquid. For example, the outer lumen is first flushed with 2 cc of water, saline, DI water or the like prior to balloon inflation. Thereafter, the inflation source container is attached to the connector leading to the inner lumen. The inflation source container works on the premise of the ideal gas law and a pressure decay model. For a given compressed gas formulation, the device is designed to equalize such that a higher starting pressure is used to inflate the balloon than is the resulting end pressure of the balloon. The starting pressure and volume are dependent upon the gas formulation selected, as well as the length of the catheter and the starting temperature (typically ambient temperature) and ending temperature (typically body temperature).

After inflation, the balloon is detached from the catheter assembly using hydraulic pressure. A syringe filled with water, DI water, or preferably saline is attached to the female end of the Y-assembly. The syringe contains 2 cc of liquid and when the syringe plunger is pushed in, enough hydraulic pressure is exerted such that the needle is ejected from the balloon valve.

Single Lumen Catheter

To further reduce the diameter of the inflation catheter, thereby increasing swallowability comfort, a single lumen catheter can be employed that does not exceed 2 French (0.66 mm) in diameter.

The needle/needle sleeve assembly is similar in design to that of the dual lumen catheter described herein. However, with the single lumen system, the distal end of the catheter lumen connects to the needle sleeve only and there is no second catheter inside. Instead, a single thread attached to a needle hub runs co-axially the length of the catheter to aid in tensile strength for detachment and overall flexibility.

The needle sleeve is slightly bell shaped or contains a circular relief or lip so that when inserted into the silicone area of the valve a lock and key mechanism is created to increase the tensile strength of the assembly, enhance the sealing for inflation, and since this is a single lumen assembly, the lip increases the force required to remove the needle from the valve so this does not occur haphazardly during the inflation process.

The proximal end of the catheter is connected to a 3-way valve and uses a method of exclusion for inflation and detachment of the balloon. The distal end of the catheter contains the needle sleeve, which is made of nylon or other similar source. The needle is metallic and preferably stainless steel.

The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible, preferably co-axial, and resistant to necking or buckling or kinking. For a single lumen system, the catheter tubing is preferably made of PEBAX®, but can also comprise bioresorbable materials such as PLA, PLAA, PLG, PCL, DL-PLCL or the like, wherein the tube can be released after inflation and detachment and swallowed as normal. The wire inside the catheter tubing attached to the needle is preferably a nylon monofilament, but Kevlar or nitinol wire or other suitable materials can also be used.

To inflate the balloon, the distal end of the catheter is attached to the balloon capsule where the needle protrudes through the self-sealable valve. The container is swallowed and a portion of the inflation catheter remains outside of the mouth. The inflation source container is connected to the proximal 3-way valve, where the port for inflation gas is chosen by excluding the other ports. The inflation fluid (preferably compressed nitrogen gas or a mixture of gases) travels down the single catheter lumen, whereby the inflation gas selects the path of least resistance, or more specifically through the needle cavity and into the balloon. The balloon is preferably inflated in less than 3 minutes.

To detach and withdraw the needle from the balloon valve, 2 cc or other suitable volume of water or other liquid is injected into the catheter at a high pressure. Since water has a high surface tension and viscosity, it occludes the needle pathway and the pressure is transferred to the outside needle sleeve, thereby breaking the fit between the needle sleeve and the balloon valve.

If it is desired to place a substance inside the balloon, such as water or acid or any alternative liquid, it can be done by using a lower pressure to inject the liquid.

Miniature Stiff-Bodied Inflation Catheter

In certain embodiments, a stiff-bodied inflation catheter can be employed, which can be placed orally or transnasally. This system can be from 1 French (0.33 mm) to 10 French (3.3 mm), preferably 8 French (2.7 mm) in diameter. A larger diameter is typically preferred to enhance pushability, with wall thickness also contributing to pushability and kink resistance. The length of the tube can be approximately 50-60 cm. As discussed above, measurement ticks can be added to the tubing to identify where the end of the tube is located, or a pH or pressure sensor on the catheter can be employed to detect location of the balloon.

This system for inflation/detachment is similar to the dual lumen system described above, but with a larger needle sleeve to accommodate the larger diameter tube. Materials that can be used in the lumen include, e.g., expanded polytetrafluoroethylene (EPTFE) for the outer lumen and polyetheretherketone (PEEK) for the inner lumen. To also enhance pushability, a strain relief device can be added to the distal and proximal ends. It is particularly preferred to have strain relief at the distal end, e.g., 1 to 8 inches, preferably 6 inches, to ensure the catheter bypasses the larynx and follows into the esophagus. The proximal end can have strain relief as well, e.g., to ensure fit of the Y-arm. The preferred material for the strain relief is a polyolefin. The method for inflation/detachment is the same method as for the dual lumen configuration where the outer lumen connects to the needle sleeve and the inner lumen connects to the needle. As part of the procedure, the patient can swallow water or other suitable liquid so as to distend esophageal tissue for smooth passage down of the device. Patients can also be administered an anesthetic at the back of the throat to numb the area and lessen the gag reflex.

The tube can also be connected to a series of encapsulated or compacted balloons on a single catheter such that a total volume of up to 1000 cc or more can be administered, as necessary. Each can be inflated and released separately. The number of balloons released can be tunable to the patient's needs and desired weight loss.

In addition, a catheter can be used for administering a gastric balloon that is similar to balloon catheters used in angioplasty termed "over-the-wire" or rapid exchange catheters. In this case where the patients attempts to swallow the catheter but fails so the stiff catheter—or physician assisted catheter can slide over the flexible catheter and the balloon can be pushed down in the same manner as the physician-assisted catheter. Different materials can be used to provide the varying degrees of flexibility or one material that is fabricated with different diameters across the length to vary the degree of stiffness can be used.

The swallowable self-inflating balloon construction method and the swallowable inflation tube construction method both remove the requirement for endoscopy to place the balloon and make the balloon administration process less invasive. This also allows for the total volume to be placed in a patient to be "titratable," or adjustable. When a balloon is placed for 30 days, a patient may report that over time they lose their feeling of fullness without eating. To compensate, another balloon can be placed easily without sedation and endoscopy. When a non-deflatable balloon is to be removed endoscopically, it is desirable to color-code the balloon composite walls with different colors so that the physician has a visual marker for removing the balloon at the end of its useful life while keeping the balloon that has remaining useful life in the patient's stomach.

In addition, the balloon wall can be marked approximately 180° from the self-sealing valve such that when the balloon is punctured endoscopically it folds more efficiently on itself so as to facilitate removal of the thin-walled structure without causing esophageal perforations and/or other damage by the balloon due to its shape, stiffness, and/or thickness of the wall material.

Inflation Fluid Container

The inflation fluid container is employed to control the amount or volume of fluid placed inside of the balloon. This can be in the form of a canister of, e.g., PVC, stainless steel, or other suitable material. The container can also be in syringe form. The materials employed are able contain a fluid, preferably in gas form, e.g., compressed or non-compressed $N_2$, Ar, $O_2$, $CO_2$, or mixture(s) thereof, or compressed or non-compressed atmospheric air (a mixture of $N_2$, $O_2$, Ar, $CO_2$, Ne, $CH_4$, He, Kr, $H_2$, and Xe). The balloon composite wall materials and respective diffusion gradients and gas permeability characteristics are used to select a fluid for inflation of the intragastric balloon, so as to provide a desired volume profile over time for the inflated balloon. The inflation fluid container materials are selected to ensure no or minimal diffusion or leakage of the fluid before it is connected to the y-arm connector or valve of the inflation catheter. The inflation fluid container preferably incorporates a pressure gauge and a connector. It can also contain a smart chip that notifies the healthcare professional of whether inflation is successful or if the balloon should be detached due to an error in the system.

To maintain "swallowability" of the balloon and to ensure comfort of the patient during the procedure, it is preferred to minimize the amount of time the catheter is placed in the mouth/esophagus. Timing of inflation is can be selected so as to minimize time in place. The outer container-catheter assembly, once swallowed, takes approximately 4-8 seconds to reach the stomach. Once in the stomach, the Inflation source container can be attached to the valve or port of catheter system. Inflation timing can be controlled by selecting the length of catheter, diameter of the catheter tube, the starting temperature, and the starting pressure. Using the Ideal Gas Law for nitrogen and Boyle's Law ($P_1V_1=P_2V_2$) the amount of starting volume/pressure can be derived, where temperature is controlled inside the inflation source container to match that of the body. It is desired to have an inflation time after swallow of less than 5 minutes, and preferably 2-3 minutes, before balloon detachment and catheter withdrawal. The inputs use to derive inflation of the balloon (preferably in less than 3 minutes) include inflation container volume, type of inflation fluid (preferably a compressed gas or compressed gas mixture), starting pressure, catheter length and diameter, and desired end volume and pressure of the balloon. Thus, due to differences in diameter, a 2 French catheter system requires a higher starting pressure to achieve the same target balloon volume and pressure in the same time frame, assuming use of the same compressed gas formulation. In general, it is understood that starting with a higher pressure with the same flow rate/volume can decrease the inflation time.

The inflation source container provides feedback to the end user based on a pressure decay system. Where there is an expected starting pressure and expected ending pressure to indicate whether the balloon is inflated properly, there is no need for endoscopic visualization. Each scenario of expected pressure outputs can have its own tolerances around it to reduce possibilities of false positives, and the inflation fluid container can provide feedback based on these tolerances as to the status of balloon inflation and detachment. This is derived based on the Ideal Gas Law, where there is an expected end pressure based on the fixed volume of the balloon. If the pressure remains high and doesn't decay as expected, this can indicate a failure in the system (e.g., the balloon container did not dissolve, the balloon is expanding in the esophagus because there is, e.g., a kink in the tube or other failure in the catheter system). For example, for a successful decay using nitrogen only as the inflation fluid, the starting pressure is 22 PSI to inflate a balloon to 250 cc and 1.7 psi (0.120 $kg/cm^2$) for a nylon-based material. To indicate successful balloon inflation, a math chip can be added to the inflation source container that provides at least one of a visual, audible, or tactile notification, or otherwise transmits a notification to a healthcare professional or administrator of whether inflation is successful or if there is an error in the system based on the pressure curve and a set of predetermined pressure tolerances and expected timing of inflation.

Another method for detection of any degree of constraint that the balloon may be experiencing (e.g., capsule dissolved but balloon is in the esophagus or duodenum, or balloon is in the stomach and the capsule has not dissolved by reading the gauge output is to employ an inflation canister that has at least two reservoirs (one large and one small) and at least two gauges, with one or more valves that allow for selection of gas release into the second reservoir or into the balloon itself. With two reservoirs, the larger reservoir can contain the total amount of fluid required to fill the balloon. A small amount of fluid can be released from the larger reservoir into the smaller reservoir first to determine the location of the balloon and its readiness for full inflation. If the small amount of fluid in the smaller reservoir is released into the balloon catheter and the feedback on the gauge of the smaller reservoir indicates that the pressure is high, this indicates that the balloon is still contained in the capsule and it is not ready to be inflated. When the gauge reads back a medium pressure level (e.g., 1-4 psi), this indicates that the balloon is in a constrained space, such as the esophagus or duodenum, and should not be inflated. When the balloon catheter's feedback as read on the gauge is approximately 1 psi, this indicates that the balloon is in the stomach and ready to be inflated. If the feedback is at 0 psi, this indicates is a leak in the balloon valve catheter system and that the device should be retrieved. Once the balloon is detected in the stomach space, then the larger reservoir is opened and the balloon is inflated to its desired pressure.

Alternatively, the balloon can be filled based on a starting pressure by using a spring mechanism, a balloon-within-balloon mechanism, or other pressure source. These mechanisms can potentially result in more predictable/consistent pressure decay curves, and again can have accompanying, predetermined tolerances for feedback back to the end user.

Composite Wall

The materials selected for the composite wall of the balloon may be optimized to maintain the original inflation gas without significant diffusion, or may also allow for diffusion of the gases located in the gastric environment, e.g., $CO_2$, $O_2$, argon, or $N_2$ to diffuse through the wall of the balloon to inflate, partially or wholly, once the balloon is placed in the stomach. A fluid (a liquid or gas) can also be added inside of the balloon using the inflation catheter(s) described herein to change diffusion direction of the balloon composite wall and when it reaches stasis based on the internal and external environment.

A gastric balloon inflated by nitrogen, $CO_2$ gas, a single fluid (gas) or a mixture of gasses employs a composite wall that provides barrier properties (fluid retention), properties imparting resistance to pH and moisture conditions in the gastric environment or the environment within the central lumen of the balloon, and structural properties to resist gastric motility forces, abrasion of the balloon wall in vivo, and damage during manufacturing and folding of the balloon. Certain materials employed in the balloon materials are able to withstand a hostile gastric environment designed to break down foreign objects (e.g., food particles). Some of the variables that the gastric environment encompasses are as follows: gastric liquid pH of from 1.5-5; temperature of approx. 37° C.; a relative humidity of 90-100%; ingress of gastric space gas content; and constant gastric motility external pressures of from 0-4 psi at variable frequencies and cycle times based on the fed state of the stomach. The external pressure imparted by gastric motility can also cause abrasions on the surface of the balloon. The inside of the balloon lumen may contain moisture from a solution injected in the balloon for timing of auto-deflation or any moisture that has transferred across the membrane due to the external humid environment. In addition to these environmental stresses the wall materials meet biocompatibility requirements and are constructed such that the total thickness of the wall (barrier material) is thin enough to be compacted and placed inside of a swallowable-sized container ("outer container") without significant damage or lodging. The outer container is small enough to transcend the esophagus (which has a diameter of approximately 2.5 cm). The wall or barrier material is also heat formable and sealable for balloon construct and maintains a bond strength that can contain internal gas pressures of up to 10 psi generated by the initial inflation pressure as well as pressure due to the ingress of gas molecules from the stomach cavity until the system's gas environment reaches stasis. The film properties that are evaluated to determine suitability for use in the composite wall of the balloon include pH resistance, water vapor transmission rate, gas barrier properties, mechanical strength/abrasion properties, temperature resistance, formability, flex-crack (Gelbo) resistance, surface energy (wettability) compliance, and heat bond potential.

The various layers in the composite wall can impart one or more desirable properties to the balloon (e.g., $CO_2$ retention, resistance to moisture, resistance to acidic environment, wettability for processing, and structural strength). A list of polymer resins and coatings that can be combined into a multi-layer preformed system ("composite wall") is provided in Tables 1a-b. These films can be adhesively bonded together, co-extruded, or adhered via tie layers or a combination thereof to obtain the desired combination of properties for the composite wall, as discussed below. The materials identified as film coatings in Tables 1a-b are provided as coatings applied to a base polymer film, e.g., PET, Nylon, or other structural layer.

TABLE 1a

Film Resins

| FILM RESINS | Characteristics | | |
|---|---|---|---|
| | Good Structural/ Behavior/Mechanical Strength/ Compliance | Good Fluid Retention Barrier Properties | Good Manufacturability/ Surface Energy Properties |
| Polyethylene Terephthalate (PET) | X | X | |
| Polytrimethylene Terephthalate (PTT) | | | |
| Liquid Crystal Polymer (LCP) | X | X | |
| Polytrimethylene naphthalate (PTN) | X | X | |
| Polyethylene naphthalate (PEN) | X | X | |
| Polyimide (PI) | X | X | |
| Linear Low Density Polyethylene (LLDPE) | | | X |
| Ethylene Vinyl Alcohol (EVOH) | | X | |
| Polyamide: Nylon (PA) and Nylon-6 (PAG)/Nylon 12 | | X | X |
| High Density Polyethylene (HDPE) | | | X |
| Polypropylene (PP) | | | X |
| Polyurethane | | | X |
| PVDC (Saran) | | X | X |
| Polyether Block Amide (Pebax) | | | X |
| Polyvinyl Alcohol (PVOH) | | X | |
| Silicone | X | | X |

TABLE 1b

Film Coatings

| FILM COATINGS | Characteristics | | |
|---|---|---|---|
| | Good Structural/ Behavior/Mechanical Strength/ Compliance | Good Fluid Retention Barrier Properties | Good Manufacturability/ Surface Energy Properties |
| Silicon Dioxide (SiO2) | | X | |
| Aluminum Oxide ($Al_2O_3$) | | X | |
| Nanopolymers (Nano/Clay) | | X | |
| External Organic Coatings (e.g., epoxy amine) | | X | |
| Inorganic Coatings (e.g., Amorphous Carbon) | | X | |
| Oxygen Scavengers | | X | |
| Parylene C | | X | |

Fluid Retention Layers

In preferred embodiments, a blended polymer resin using multiple layers is employed to maintain the inflated balloon's shape and volume by retaining the inflation fluid for the duration of the intended use. Certain barrier films, widely used in the food packaging and plastic bottling industries, can advantageously be employed for this purpose in the composite wall of the balloon. Preferably, the barrier materials have a low permeability to carbon dioxide (or other gases, liquids, or fluids that are alternatively or additionally used to inflate the volume-occupying subcomponent). These barrier layers preferably have good adherence to the base material. Preferred barrier coating materials and films include polyethylene terephthalate (PET), linear low density polyethylene (LLDPE), ethylene vinyl alcohol (EVOH), polyamides such as Nylon (PA) and Nylon-6 (PA-6), polyimide (PI), liquid crystal polymer (LCP), high density polyethylene (HDPE), polypropylene (PP), biocompatible poly(hydroxyamino ethers), polyethylene naphthalate, polyvinylidene chloride (PVDC), saran, ethylene vinyl alcohol copolymers, polyvinyl acetate, silicon oxide (SiOx), silicon dioxide ($SiO_2$), aluminum oxide ($Al_2O_3$), polyvinyl alcohol (PVOH), nanopolymers (e.g., nanoclay), polyimide thermoset film, EVALCA EVAL EF-XL, Hostaphan GN, Hostaphan RHBY, RHB MI, Techbarrier HX (SiOx-coated PET), Triad Silver (silver metalized PET), Oxyshield 2454, Bicor 84 AOH, acrylonitrile copolymers, and copolymers of terephthalic acid and isophthalic acid with ethylene glycol and at least one diol. Alternative gas-barrier materials include polyamine-polyepoxides. These materials are typically provided as a solvent-based or aqueous-based thermosetting composition and are typically spray-coated onto a preform and then heat-cured to form the finished barrier coating. Alternative gas barrier materials that can be applied as coatings to the volume-occupying subcomponent include metals such as silver or aluminum. Other materials that may be used to improve the gas impermeability of the volume occupying subcomponent include, but are not limited to, gold or any noble metal, PET coated with saran, and conformal coatings.

One method that is used in the packaging industry to delay diffusion of the inflation fluid is to thicken the material. Thickening the material is generally not preferred, as the total composite wall thickness preferably does not exceed 0.004 inches (0.010 cm) in order for the balloon to be foldable into the desired delivery container size for swallowing by a patient.

A multilayer polymer film that is able to withstand the gastric environment over the course of the usable life of the balloon includes linear low density polyethylene (LLDPE) adhesively bonded to a Nylon 12 film. Alternatively, an additional film layer with barrier properties, such as PVDC can be added to the composite wall.

The layers providing gas barrier properties are preferably situated as inner layers in the composite wall as they are less mechanically robust than resins that are considered "structural" such as Nylon and the like.

Structural Layers

Layers such as polyurethane, Nylon, or polyethylene terephthalate (PET) can be added to the composite wall for structural purposes, and are preferably placed as outermost (proximal to the gastric environment or proximal to the central lumen of the balloon) layers, provided that the pH resistance of such layers can withstand the acidic environment of the stomach or the central lumen of the balloon.

Layer Chemistry

Polyethylene Terephthalate (PET)

Polyethylene terephthalate is a thermoplastic polymer resin of the polyester family. Polyethylene terephthalate may exist as an amorphous (transparent) or as a semi-crystalline material. The semi-crystalline material can appear transparent (spherulites <500 nm) or opaque and white (spherulites up to a size of some µm) depending on its crystal structure and spherulite size. Its monomer (bis-β-hydroxyterephthalate) can be synthesized by the esterification reaction between terephthalic acid and ethylene glycol with water as a byproduct, or by transesterification reaction between ethylene glycol and dimethyl terephthalate with methanol as a byproduct. Polymerization is through a polycondensation reaction of the monomers (done immediately after esterification/transesterification) with ethylene glycol as the byproduct (the ethylene glycol is directly recycled in production). Some of the trade names of PET products are Dacron, Diolen, Tergal, Terylene, and Trevira fibers, Cleartuf, Eastman PET and Polyclear bottle resins, Hostaphan, Melinex, and Mylar films, and Amite, Ertalyte, Impet, Rynite and Valox injection molding resins.

PET consists of polymerized units of the monomer ethylene terephthalate, with repeating $C_{10}H_8O_4$ units. PET can be semi-rigid to rigid, depending on its thickness, and is very lightweight. It makes a good gas and fair moisture barrier, as well as a good barrier to alcohol and solvents. It is strong and impact-resistant. It is naturally colorless with high transparency.

When produced as a thin film (biaxially oriented PET film, often known by one of its trade names, "Mylar"), PET can be aluminized by evaporating a thin film of metal onto it to reduce its permeability, and to make it reflective and opaque (MPET). These properties are useful in many applications, including flexible food packaging. When filled with glass particles or fibers, it becomes significantly stiffer and more durable. This glass-filled plastic, in a semi-crystalline formulation, is sold under the trade name Rynite, Amite, Hostadur, and Crastin.

One of the most important characteristics of PET is intrinsic viscosity. The intrinsic viscosity of the material, measured in deciliters per gram (dl/g) is dependent upon the length of its polymer chains. The longer the chains, the stiffer the material, and therefore the higher the intrinsic viscosity. The average chain length of a particular batch of resin can be controlled during polymerization. An intrinsic viscosity of about: 0.65 dl/g-0.84 dl/g is preferred for use in a composite wall.

In addition to pure (homopolymer) PET, PET modified by copolymerization is also available. In some cases, the modified properties of copolymer are more desirable for a particular application. For example, cyclohexane dimethanol (CHDM) can be added to the polymer backbone in place of ethylene glycol. Since this building block is much larger (6additional carbon atoms) than the ethylene glycol unit it replaces, it does not fit in with the neighboring chains the way an ethylene glycol unit can. This interferes with crystallization and lowers the polymer's melting temperature. Such PET is generally known as PETG (Eastman Chemical and SK Chemicals are the only two manufacturers). PETG is a clear amorphous thermoplastic that can be injection molded or sheet extruded. It can be colored during processing. Another common modifier is isophthalic acid, replacing some of the 1,4-(para-) linked terephthalate units. The 1,2-(ortho-) or 1,3-(meta-) linkage produces an angle in the chain, which also disturbs crystallinity. Such copolymers are advantageous for certain molding applications, such as thermoforming. On the other hand, crystallization is important in other applications where mechanical and dimensional stability are important. For PET bottles, the use of small amounts of CHDM or other comonomers can be useful: if only small amounts of comonomers are used, crystallization is slowed but not prevented entirely. As a result, bottles are obtainable via stretch blow molding ("SBM"), which are both clear and crystalline enough to be an adequate barrier to aromas and gases such as carbon dioxide in carbonated beverages.

Crystallization occurs when polymer chains fold up on themselves in a repeating, symmetrical pattern. Long polymer chains tend to become entangled on themselves, which prevents full crystallization in all but the most carefully controlled circumstances. 60% crystallization is the upper limit for commercial products, with the exception of polyester fibers.

PET in its natural state is a crystalline resin. Clear products can be produced by rapidly cooling molten polymer to form an amorphous solid. Like glass, amorphous PET forms when its molecules are not given enough time to arrange themselves in an orderly fashion as the melt is cooled. At room temperature the molecules are frozen in place, but if enough heat energy is put back into them, they begin to move again, allowing crystals to nucleate and grow. This procedure is known as solid-state crystallization.

Like most materials, PET tends to produce many small crystallites when crystallized from an amorphous solid, rather than forming one large single crystal. Light tends to scatter as it crosses the boundaries between crystallites and the amorphous regions between them. This scattering means that crystalline PET is opaque and white in most cases. Fiber drawing is among the few industrial processes that produces a nearly single-crystal product.

Comonomers such as CHDM or isophthalic acid lower the melting temperature and reduces the degree of crystallinity of PET (especially important when the material is used for bottle manufacturing). Thus the resin can be plastically formed at lower temperatures and/or with lower force. This helps to prevent degradation, reducing the acetaldehyde content of the finished product to an acceptable (that is, unnoticeable) level. Other ways to improve the stability of the polymer is by using stabilizers, mainly antioxidants such as phosphites. Recently, molecular level stabilization of the material using nanostructured chemicals has also been considered.

Unreinforced PET has the following properties: Bulk Density 0.800-0.931 g/cc; Density 1.10-1.20 g/cc @Temperature 285-285° C.; 1.25-1.91 g/cc; Apparent Bulk Density 0.000850 g/cc; Water Absorption 0.0500-0.800%; Moisture Absorption at Equilibrium 0.200-0.300%; Water Absorption at Saturation 0.400-0.500%; Particle Size 2500 μm; Water Vapor Transmission 0.490-6.00 g/m$^2$/day; Oxygen Transmission 5.10-23.0 cc-mm/m$^2$-24 hr-atm; Viscosity Measurement 0.550-0.980; Viscosity Test 74.0-86.0 cm$^3$/g; Thickness 250-254 microns; Linear Mold Shrinkage 0.00100-0.0200 cm/cm; Linear Mold Shrinkage, Transverse 0.00200-0.0110 cm/cm; Hardness, Rockwell M 80.0-95.0; Hardness, Rockwell R 105-120 105-120; Ball Indentation Hardness 160-170 MPa; Tensile Strength, Ultimate 22.0-207 MPa; Film Tensile Strength at Yield, MD 55.0-59.0 MPa; Film Tensile Strength at Yield, TD 53.0-57.0 MPa; Film Elongation at Break, MD 40.0-600%; Film Elongation at Break, TD 200-600%; Film Elongation at Yield, MD 4.00-6.00%; Film Elongation at Yield, TD 4.00-6.00%; Tensile Strength, Yield 47.0-90.0 MPa; Elongation at Break 1.50-600%; Elongation at Yield 3.50-30.0%; Modulus of Elasticity 1.83-14.0 GPa; Flexural Modulus 1.90-15.2 GPa; Flexural Yield Strength 55.0-240 MPa; Compressive Yield Strength 20.0-123 MPa; Izod Impact, Unnotched 2.67 J/cm-NB; Izod Impact, Unnotched Low Temp (ISO) 160-181 kJ/m$^2$; Izod Impact, Notched, Low Temp (ISO) 3.10-4.20 kJ/m$^2$; Charpy Impact Unnotched 3.00 J/cm$^2$-NB; Charpy Impact, Notched, Low Temp 0.270-0.500 J/cm$^2$; Charpy Impact, Notched 0.200-1.40 J/cm$^2$; Impact Test 0.800-8.20 J @Temperature −40.0° C.; Coefficient of Friction 0.190-0.250; Tear Strength, Total 15.0-120 N; Elmendorf Tear Strength, MD 3.14-4.00 g/micron; Elmendorf Tear Strength, TD 3.24-5.20 g/micron; Dart Drop 1.08-2.00 g/micron; Taber Abrasion, mg/1000 Cycles; Film Tensile Strength at Break, MD 13.8-60.0 MPa; Film Tensile Strength at Break, TD 39.0-48.0 MPa; Izod Impact, Notched @−40° C. 0.270-0.630 J/cm; Izod Impact, Notched 0.139-100 J/cm; Izod Impact, Notched (ISO) 2.00-10.0 kJ/m$^2$; Electrical Resistivity 5.00e+6-1.00e+16 ohm-cm; Surface Resistance 1.00e+14-1.00e+16 ohm; Dielectric Constant 2.40-3.90; Dielectric Strength 15.7-60.0 kV/mm; Dissipation Factor 0.00100-0.0250; Arc Resistance 80.0-181 sec; Comparative Tracking Index 175-600 V; Heat of Fusion 56.0-65.0 J/g; CTE, linear 25.0-92.0 μm/m-° C.; CTE, linear, Transverse to Flow 48.0-80.0 μm/m-° C.; Specific Heat Capacity 1.10-1.20 J/g-° C.; 1.30-2.30 J/g-° C. @Temperature 60.0-280° C.; Thermal Conductivity 0.190-0.290 W/m-K; Melting Point 200-255° C.; Maximum Service Temperature, Air 100-225° C.; Deflection Temperature at 0.46 MPa (66 psi) 66.0-245° C.; Deflection Temperature at 1.8 MPa (264 psi) 60.0-240° C.; Vicat Softening Point 74.0-85.0° C.; Minimum Service Temperature, Air −20.0° C.; Glass Temperature 70.0-78.0° C.; UL RTI, Electrical 75.0-175° C.; Haze 0.300-10.0%; Gloss 108-166%; Transmission, Visible 67.0-99.0%; Gardner Color Number −3.00-85.0; Processing Temperature 120-295° C.; Mold Temperature 10.0-163° C.; Drying Temperature 70.0-160° C.; Dry Time 3.00-8.00 hour; Moisture Content 0.0100-0.400%; Injection Pressure 68.9-120 MPa; Back Pressure 8.00-18.0 MPa.

Polyethylene terephthalate films are available from Mitsubishi Polyester Film of Wiesbaden, Germany under the trade name Hostaphan®. Hostaphan® GN is a glass clear biaxially oriented film, made of polyethylene terephthalate (PET) and is characterized by its high transparency and surface gloss and its low haze accompanied by its excellent mechanical strength and dimensional stability. Hostaphan® GN is one or two side chemically treated for improved slip and processability as well as for improvement of the adhesion of coatings, printing inks or metallic layers. Hostaphan® RHBY is a biaxially oriented film made of polyethylene terephthalate (PET) with a structure optimized to offer previously unattainable barrier properties against oxygen, water vapor and other gases as well as aroma substances after vacuum coating with aluminum, $Al_2O_3$ or SiOx.

Linear Low-Density Polyethylene (LLDPE)

Linear low-density polyethylene (LLDPE) is a substantially linear polymer (polyethylene), with significant numbers of short branches, commonly made by copolymerization of ethylene with longer-chain olefins. Linear low-density polyethylene differs structurally from conventional low-density polyethylene because of the absence of long chain branching. The linearity of LLDPE results from the different manufacturing processes of LLDPE and LDPE. In general, LLDPE is produced at lower temperatures and pressures by copolymerization of ethylene and such higher alpha olefins as butene, hexene, or octene. The copolymerization process produces an LLDPE polymer that has a narrower molecular weight distribution than conventional LDPE and in combination with the linear structure, significantly different rheological properties.

The production of LLDPE is initiated by transition metal catalysts, particularly Ziegler or Philips type of catalyst. The actual polymerization process can be done in either solution phase or gas phase reactors. Usually, octene is the copolymer in solution phase while butene and hexene are copolymerized with ethylene in a gas phase reactor. The LLDPE resin produced in a gas phase reactor is in granular form and may be sold as granules or processed into pellets. LLDPE has higher tensile strength and higher impact and puncture resistance than LDPE. It is very flexible and *elongates* under stress. It can be used to make thinner films, with better environmental stress cracking resistance. It has good resistance to chemicals and to ultraviolet radiation. It has good electrical properties. However it is not as easy to process as LDPE, has lower gloss, and narrower range for heat sealing.

LDPE and LLDPE have unique theoretical or melt flow properties. LLDPE is less shear sensitive because of its narrower molecular weight distribution and shorter chain branching. During a shear process, such as extrusion, LLDPE remains more viscous, therefore harder to process than an LDPE of equivalent melt index. The lower shear sensitivity of LLDPE allows for a faster stress relaxation of the polymer chains during extrusion and therefore the physical properties are susceptible to changes in blow-up ratios. In melt extension, LLDPE has lower viscosity at all strain rates. This means it will not strain harden the way LDPE does when elongated. As the deformation rate of the polyethylene increases, LDPE demonstrates a dramatic rise in viscosity because of chain entanglement. This phenomena is not observed with LLDPE because of the lack of long-chain branching in LLDPE allows the chains to "slide by" one another upon elongation without becoming entangled. This characteristic is important for film applications because LLDPE films can be downgauged easily while maintaining high strength and toughness.

Properties of film grade LLDPE include: Density 0.902-0.960 g/cc; Moisture Vapor Transmission 0.240-0.470 cc-mm/mg-24 hr-atm; Water Vapor Transmission 6.00-8.00 g/m$^2$/day; Oxygen Transmission 0.720-236 cc-mm/mg-24 hr-atm; Oxygen Transmission Rate 3500-5000 cc/m$^2$/day; Viscosity 37000-79000 cP @Temperature 190-190° C.; 37000-79000 cP @Shear Rate 300-5000 l/s; 37000-79000 cP @Shear Rate 300-5000 l/s; Thickness 12.7-76.2 microns; Melt Flow 0.200-40.0 g/10 min; Base Resin Melt Index 0.700-3.50 g/10 min; Antiblock Level 3500-9000 ppm; Slip Level 0.000-1700 ppm; Tensile Strength, Ultimate 9.80-26.2 MPa; Film Tensile Strength at Yield, MD 7.38-74.0 MPa; Film Tensile Strength at Yield, TD 6.90-77.0 MPa; Film Elongation at Break, MD 80.0-1460%; Film Elongation at Break, TD 460-1710%; Film Elongation at Yield, MD 435-640%; Film Elongation at Yield, TD 670-890%; Tensile Strength, Yield 9.70-22.1 MPa; Elongation at Break 8.00-1000%; Modulus of Elasticity 0.0110-0.413 GPa; Secant Modulus, MD 0.0103-0.717 GPa; Secant Modulus, TD 0.0106-0.869 GPa; Impact 48.0-65.0; Impact Test 0.452-5.00 J; Coefficient of Friction 0.100-2.00; Coefficient of Friction, Static 0.170-1.00; Elmendorf Tear Strength MD 25.0-1080 g 2; Elmendorf Tear Strength TD 180-1470 g; Elmendorf Tear Strength, MD 0.0750-20.9 g/micron; Elmendorf Tear Strength, TD 0.275-37.8 g/micron; Dart Drop 1.57-42.5 g/micron; Dart Drop Test 30.0-1350 g; Seal Strength 1800-2400 g/25 mm; Film Tensile Strength at Break, MD 9.65-82.7 MPa; Film Tensile Strength at Break, TD 7.24-55.1 MPa; Heat Seal Strength Initiation Temperature 72.0-100° C.; Melting Point 120-128° C.; Crystallization Temperature 104-115° C.; Vicat Softening Point 93.0-123° C.; Haze 0.700-80.0%; Gloss 3.00-140%; Processing Temperature 90.0-310° C.; Die Opening 0.0810-0.254 cm; Blow-up Ratio (BUR) 1.50-4.00.

Ethylene Vinyl Alcohol (EVOH)

Ethylene Vinyl Alcohol is a formal copolymer of ethylene and vinyl alcohol. Because the latter monomer mainly exists as its tautomer acetaldehyde, the copolymer is prepared by polymerization of ethylene and vinyl acetate followed by hydrolysis. The plastic resin is commonly used in food applications, and in plastic gasoline tanks for automobiles. Its primary purpose is to provide barrier properties, primarily as an oxygen barrier for improved food packaging shelf life and as a hydrocarbon barrier for fuel tanks EVOH is typically coextruded or laminated as a thin layer between cardboard, foil, or other plastics. EVOH copolymer is defined by the mole % ethylene content: lower ethylene content grades have higher barrier properties; higher ethylene content grades have lower temperatures for extrusion.

Ethylene Vinyl Alcohol (EVOH) is one of the most common clear high barrier films used today. It is applied as a discrete layer in a coextrusion. EVOH provides excellent oxygen barrier properties (0.006-0.12 cc-mil/100 in$^2$-day). The barrier that a particular EVOH film provides is dependent upon a number of factors: mole percent—as the ethylene mole percent increases, the barrier decreases; degree of crystallinity—as the degree of crystallinity increases, the barrier properties improve; thickness—as with all films, as the thickness increases, the barrier increases; temperature—as the temperature increases, the barrier decreases; humidity—at high humidity levels, the barrier provided by EVOH drops rapidly (it is the humidity level at the EVOH interface rather than ambient humidity that is critical). In addition to providing an excellent oxygen barrier, EVOH is also an excellent odor and aroma barrier. It has the added advantage of being thermoformable making it popular for 3D applications.

EVALCA EVAL® EF-XL Ethylene Vinyl Alcohol Copolymer Film has the following properties: Moisture Vapor Transmission 0.600 cc-mm/mg-24 hr-atm 40° C., 90% RH; Oxygen Transmission 0.00400 cc-mm/mg-24 hr-atm 20° C.; 65% RH (permeability increases significantly at higher moisture content); thickness 15.2 microns; Film Elongation at Break, MD 100% 10%/min.; ASTM D638 Film Elongation at Break, TD 100% 10%/min.; ASTM D638 Secant Modulus, MD 3.50 GPa; Youngs Modulus, ASTM D638, 10%/min.; Secant Modulus, TD 3.50 GPa; Youngs Modulus, ASTM D638, 10%/min.; Elmendorf Tear Strength MD 260 g; ASTM D638 Elmendorf Tear Strength TD 330 g; ASTM D638 Elmendorf Tear Strength, MD 17.0 g/micron; ASTM D638 Elmendorf Tear Strength, TD 21.7 g/micron; ASTM D638 Film Tensile Strength at Break, MD 205 MPa 10%/min.; ASTM D638 Film Tensile Strength at Break, TD 195 MPa 10%/min.; Surface Resistance 2.70e+15 ohm; Dielectric Constant 5.00; Dissipation Factor 0.220; Specific Heat Capacity 2.40 J/g-° C.; Thermal Conductivity 0.340 W/m-K; Melting Point 181° C. DSC; Haze 0.500% 65% RH; Gloss 95.0% 65% RH. EVAL® ethylene vinyl alcohol films are available from Kuraray America, Inc. of Houston, Tex.

Nylon

Nylon is a generic designation for a family of synthetic polymers known generically as polyamides. Nylon is a thermoplastic silky material. There are two common methods of making nylon for fiber applications. In one approach, molecules with an acid (COOH) group on each end are reacted with molecules containing amine (NH2) groups on each end. The resulting nylon is named on the basis of the number of carbon atoms separating the two acid groups and the two amines. These are formed into monomers of intermediate molecular weight, which are then reacted to form long polymer chains.

Solid nylon is used for mechanical parts such as machine screws, gears and other low- to medium-stress components previously cast in metal. Engineering-grade nylon is processed by extrusion, casting, and injection molding. Solid nylon is used in hair combs. Type 6/6 Nylon 101 is the most common commercial grade of nylon, and Nylon 6 is the most common commercial grade of molded nylon. Nylon is available in glass-filled variants which increase structural and impact strength and rigidity, and molybdenum sulfide-filled variants which increase lubricity.

Aramids are another type of polyamide with quite different chain structures which include aromatic groups in the main chain. Such polymers make excellent ballistic fibers.

Nylons are condensation copolymers formed by reacting equal parts of a diamine and a dicarboxylic acid, so that peptide bonds form at both ends of each monomer in a process analogous to polypeptide biopolymers. The numerical suffix specifies the numbers of carbons donated by the monomers; the diamine first and the diced second. The most common variant is nylon 6-6 which refers to the fact that the diamine (hexamethylene diamine) and the diacid (adipic acid) each donate 6 carbons to the polymer chain. As with other regular copolymers like polyesters and polyurethanes, the "repeating unit" consists of one of each monomer, so that they alternate in the chain. Since each monomer in this copolymer has the same reactive group on both ends, the direction of the amide bond reverses between each monomer, unlike natural polyamide proteins which have overall directionality. In the laboratory, nylon 6-6 can also be made using adipoyl chloride instead of adipic. It is difficult to get the proportions exactly correct, and deviations can lead to chain termination at molecular weights less than a desirable 10,000 daltons. To overcome this problem, a crystalline, solid "nylon salt" can be formed at room temperature, using an exact 1:1 ratio of the acid and the base to neutralize each other. Heated to 285° C., the salt reacts to form nylon polymer. Above 20,000 daltons, it is impossible to spin the chains into yarn, so to combat this some acetic acid is added to react with a free amine end group during polymer elongation to limit the molecular weight. In practice, and especially for nylon 6,6, the monomers are often combined in a water solution. The water used to make the solution is evaporated under controlled conditions, and the increasing concentration of "salt" is polymerized to the final molecular weight.

Homopolymer nylon 6, or polycaprolactam, is not a condensation polymer, but formed by a ring-opening polymerization (alternatively made by polymerizing aminocaproic acid). The peptide bond within the caprolactam is broken with the exposed active groups on each side being incorporated into two new bonds as the monomer becomes part of the polymer backbone. In this case, all amide bonds lie in the same direction, but the properties of nylon 6 are sometimes indistinguishable from those of nylon 6,6—except for melt temperature (N6 is lower) and some fiber properties in products like carpets and textiles. There is also nylon 9.

Nylon 5,10, made from pentamethylene diamine and sebacic acid has superior properties, but is more expensive to make. In keeping with this naming convention, "nylon 6,12" (N-6,12) or "PA-6,12" is a copolymer of a 6C diamine and a 12C diacid. Similarly for N-5,10 N-6,11; N-10,12, etc. Other nylons include copolymerized dicarboxylic acid/diamine products that are not based upon the monomers listed above. For example, some aromatic nylons are polymerized with the addition of diacids like terephthalic acid (Kevlar) or isophthalic acid (Nomex), more commonly associated with polyesters. There are copolymers of N-6,6/N6; copolymers of N-6,6/N-6/N-12; and others. Because of the way polyamides are formed, nylon can seem to be limited to unbranched, straight chains. But "star" branched nylon can be produced by the condensation of dicarboxylic acids with polyamines having three or more amino groups.

Above their melting temperatures, Tm, thermoplastics like nylon are amorphous solids or viscous fluids in which the chains approximate random coils. Below Tm, amorphous regions alternate with regions which are lamellar crystals. The amorphous regions contribute elasticity and the crystalline regions contribute strength and rigidity. The planar amide (—CO—NH—) groups are very polar, so nylon forms multiple hydrogen bonds among adjacent strands. Because the nylon backbone is so regular and symmetrical, especially if all the amide bonds are in the trans configuration, nylons often have high crystallinity and make excellent fibers. The amount of crystallinity depends on the details of formation, as well as on the kind of nylon. Apparently it can never be quenched from a melt as a completely amorphous solid.

Nylon 6,6 can have multiple parallel strands aligned with their neighboring peptide bonds at coordinated separations of exactly 6 and 4 carbons for considerable lengths, so the carbonyl oxygens and amide hydrogens can line up to form interchain hydrogen bonds repeatedly, without interruption. Nylon 5,10 can have coordinated runs of 5 and 8 carbons. Thus parallel (but not antiparallel) strands can participate in extended, unbroken, multi-chain β-pleated sheets, a strong and tough supermolecular structure similar to that found in natural silk fibroin and the β-keratins in feathers (proteins have only an amino acid a-carbon separating sequential —CO—NH— groups). Nylon 6 will form uninterrupted H-bonded sheets with mixed directionalities, but the β-sheet wrinkling is somewhat different. The three-dimensional disposition of each alkane hydrocarbon chain depends on rotations about the 109.47° tetrahedral bonds of singly-bonded carbon atoms.

Block nylon tends to be less crystalline, except near the surfaces due to shearing stresses during formation. Nylon is clear and colorless, or milky, but is easily dyed. Multistranded nylon cord and rope is slippery and tends to unravel. The ends can be melted and fused with a heat source such as a flame or electrode to prevent this.

When dry, polyamide is a good electrical insulator. However, polyamide is hygroscopic. The absorption of water will change some of the material's properties such as its electrical resistance. Nylon is less absorbent than wool or cotton.

Nylon can be used as the matrix material in composite materials, with reinforcing fibers like glass or carbon fiber, and has a higher density than pure nylon. Such thermoplastic composites (25% glass fiber) are frequently used in car components next to the engine, such as intake manifolds, where the good heat resistance of such materials makes them feasible competitors to metals.

All nylons are susceptible to hydrolysis, especially by strong acids, a reaction essentially the reverse of the synthetic reaction shown above. The molecular weight of nylon products so attacked drops fast, and cracks form quickly at the affected zones. Lower members of the nylons (such as nylon 6) are affected more than higher members such as nylon 12. This means that nylon parts cannot be used in contact with sulfuric acid for example, such as the electrolyte used in lead-acid batteries. When being molded, nylon must be dried to prevent hydrolysis in the molding machine barrel since water at high temperatures can also degrade the polymer.

Polyimide (PI)

Polyimide is a polymer of imide monomers. Thermosetting polyimides are commercially available as uncured resins, stock shapes, thin sheets, laminates and machines parts. Thermoplastic polyimides are very often called pseudothermoplastic. There are two general types of polyimides. One type, so-called linear polyimides, is made by combining imides into long chains. Aromatic heterocyclic polyimides are the other usual kind Examples of polyimide films include Apical, Kapton, UPILEX, VTEC PI, Norton TH and Kaptrex. Polyimide parts and shapes include VTEC PI, Meldin, Vespel and typical monomers include pyromellitic dianhydride and 4,4'-oxydianiline.

Thermosetting polyimides are known for thermal stability, good chemical resistance, excellent mechanical properties, and characteristic orange/yellow color. Polyimides compounded with graphite or glass fiber reinforcements have flexural strengths of up to 50,000 psi and flexural moduli of 3,000,000 psi. Thermoset polyimides exhibit very low creep and high tensile strength. These properties are maintained during continuous use to temperatures of 232° C. and for short excursions, as high as 482° C. Molded polyimide parts and laminates have very good heat resistance. Normal operating temperatures for such parts and laminates range from cryogenic to those exceeding 260° C. Polyimides are also inherently resistant to flame combustion and do not usually need to be mixed with flame retardants. Most carry a UL rating of VTM-0. Polyimide laminates have a flexural strength half-life at 249° C. of 400 hours.

Typical polyimide parts are not affected by commonly used solvents and oils including hydrocarbons, esters, ethers, alcohols and freons. They also resist weak acids but are not recommended for use in environments that contain alkalis or inorganic acids. Some polyimides, such as CP1 and CORIN XLS, are solvent-soluble and exhibit high optical clarity. The solubility properties lend them towards spray and low temperature cure applications.

The polyimide materials are lightweight, flexible, resistant to heat and chemicals. Therefore, they are used in the electronics industry for flexible cables, as an insulating film on magnet wire and for medical tubing. For example, in a laptop computer, the cable that connects the main logic board to the display (which must flex every time the laptop is opened or closed) is often a polyimide base with copper conductors. The semiconductor industry uses polyimide as a high-temperature adhesive; it is also used as a mechanical stress buffer. Some polyimide can be used like a photoresist; both "positive" and "negative" types of photoresist-like polyimide exist in the market.

Thermoset film polyimide has the following properties: Density 1.40-1.67 g/cc; Water Absorption 1.40-3.00%; Moisture Absorption at Equilibrium 0.400-1.80%; Water Absorption at Saturation 1.20-2.50%; Moisture Vapor Transmission 2.40-17.5 cc-mm/m$^2$-24 hr-atm; Oxygen Transmission 9.90 cc-mm/mg-24 hr-atm; Thickness 22.0-187 microns; Film Tensile Strength at Yield, MD 49.0-255 MPa; Film Tensile Strength at Yield, TD 100-160 MPa; Film Elongation at Break, MD 10.0-85.0%; Film Elongation at Yield, MD 40.0-50.0%; Film Elongation at Yield, TD 45.0-55.0%; Tensile Strength, Yield 73.3-160 MPa; Elongation at Yield 10.0-45.0%; Poissons Ratio 0.340; Secant Modulus 2.28-5.20 GPa; Secant Modulus, MD 1.76-9.12 GPa; Impact Test 0.686-1.56 J; Coefficient of Friction 0.400-0.480; Coefficient of Friction, Static 0.630; Tear Strength Test 7.20-430; Peel Strength 0.240 kN/m; Elmendorf Tear Strength MD 8.20-270 g; Film Tensile Strength at Break, MD 98.1-736 MPa; Electrical Resistivity 1.00e+10-2.30e+17 ohm-cm; 1.00e+15-1.00e+16 ohm-cm @Temperature 200° C.; Surface Resistance 10000-1.00e+17 ohm; 1.00e+15-1.00e+15 ohm @Temperature 200° C.; Dielectric Constant 2.70-4.00; Dielectric Strength 48.0-272 kV/mm @Temperature 200° C.; Dissipation Factor 0.00130-0.0100; CTE, linear 12.0-20.0 μm/m-° C.; 32.0-40.0 μm/m-° C. @Temperature 100-300° C.; Specific Heat Capacity 1.09-1.13 J/g-° C.; Thermal Conductivity 0.120-0.289 W/m-K; Maximum Service Temperature, Air 180-400° C.; Minimum Service Temperature, Air −269° C.; Glass Temperature 360-500° C.; Oxygen Index 37.0-66.0%; Shrinkage 0.0100-0.200%; Refractive Index 1.70.

Liquid Crystal Polymer (LCP)

Liquid-crystal polymers (LCPs) are a class of aromatic polyester polymers. They are extremely unreactive and inert, and highly resistant to fire. Liquid crystallinity in polymers may occur either by dissolving a polymer in a solvent (lyotropic liquid-crystal polymers) or by heating a polymer above its glass or melting transition point (thermotropic liquid-crystal polymers). Liquid-crystal polymers are present in melted/liquid or solid form. In liquid form liquid-crystal polymers have primarily applications in liquid-crystal displays (LCDs). In solid form the main example of lyotropic LCPs is the commercial aramid known as Kevlar. The chemical structure of this aramid consists of linearly substituted aromatic rings linked by amide groups. In a similar way, several series of thermotropic LCPs have been commercially produced by several companies (e.g., Vectra). A high number of LCPs, produced in the 1980s, displayed order in the melt phase analogous to that exhibited by nonpolymeric liquid crystals. Processing of LCPs from liquid-crystal phases (or mesophases) gives rise to fibers and injected materials having high mechanical properties as a consequence of the self-reinforcing properties derived from the macromolecular orientation in the mesophase. Today, LCPs can be melt-processed on conventional equipment at high speeds with excellent replication of mold details.

A unique class of partially crystalline aromatic polyesters based on p-hydroxybenzoic acid and related monomers, liquid-crystal polymers is capable of forming regions of highly ordered structure while in the liquid phase. However, the degree of order is somewhat less than that of a regular solid crystal. Typically LCPs have a high mechanical strength at high temperatures, extreme chemical resistance, inherent flame retardancy, and good weatherability. Liquid-crystal polymers come in a variety of forms from sinterable high temperature to injection moldable compounds. LCP can be welded, though the lines created by welding are a weak point in the resulting product. LCP has a high Z-axis coefficient of thermal expansion.

LCPs are exceptionally inert. They resist stress cracking in the presence of most chemicals at elevated temperatures, including aromatic or halogenated hydrocarbons, strong acids, bases, ketones, and other aggressive industrial substances. Hydrolytic stability in boiling water is excellent. Environments that deteriorate the polymers are high-temperature steam, concentrated sulfuric acid, and boiling caustic materials. Because of their various properties, LCPs are useful for electrical and mechanical parts, food containers, and any other applications requiring chemical inertness and high strength.

High-Density Polyethylene (HDPE)

High-density polyethylene (HDPE) or polyethylene high-density (PEHD) is a polyethylene thermoplastic made from petroleum. HDPE has little branching, giving it stronger intermolecular forces and tensile strength than lower-density polyethylene. It is also harder and more opaque and can withstand somewhat higher temperatures (120° C. for short periods, 110° C. continuously). High-density polyethylene, unlike polypropylene, cannot withstand normally-required autoclaving conditions. The lack of branching is ensured by an appropriate choice of catalyst (e.g., Ziegler-Natta catalysts) and reaction conditions. HDPE contains the chemical elements carbon and hydrogen. Hollow goods manufactured through blow molding are the most common application area for HDPE.

Polypropylene (PP)

Polypropylene or polypropene (PP) is a thermoplastic polymer, made by the chemical industry and used in a wide variety of applications, including packaging, textiles (e.g. ropes, thermal underwear and carpets), stationery, plastic parts and reusable containers of various types, laboratory equipment, loudspeakers, automotive components, and polymer banknotes. An addition polymer made from the monomer propylene, it is rugged and unusually resistant to many chemical solvents, bases and acids.

Most commercial polypropylene is isotactic and has an intermediate level of crystallinity between that of low density polyethylene (LDPE) and high density polyethylene (HDPE); its Young's modulus is also intermediate. PP is normally tough and flexible, especially when copolymerized with ethylene. This allows polypropylene to be used as an engineering plastic, competing with materials such as ABS. Polypropylene is reasonably economical, and can be made translucent when uncolored but is not as readily made transparent as polystyrene, acrylic or certain other plastics. It is often opaque and/or colored using pigments. Polypropylene has good resistance to fatigue.

Polypropylene has a melting point of ~160° C. (320° F.), as determined by Differential scanning calorimetry (DSC). The MFR (Melt Flow Rate) or MFI (Melt Flow Index) is a measure of PP's molecular weight. This helps to determine how easily the molten raw material will flow during processing. Higher MFR PPs fill the plastic mold more easily during the injection or blow molding production process. As the melt flow increases, however, some physical properties, like impact strength, will decrease.

There are three general types of PP: homopolymer, random copolymer and block copolymer. The comonomer used is typically ethylene. Ethylene-propylene rubber or EPDM added to PP homopolymer increases its low temperature impact strength. Randomly polymerized ethylene monomer added to PP homopolymer decreases the polymer crystallinity and makes the polymer more transparent.

Polypropylene is liable to chain degradation from exposure to UV radiation such as that present in sunlight. For external applications, UV-absorbing additives must be used. Carbon black also provides some protection from UV attack. The polymer can also be oxidized at high temperatures, a common problem during molding operations. Anti-oxidants are normally added to prevent polymer degradation.

The relative orientation of each methyl group relative to the methyl groups on neighboring monomers has a strong effect on the finished polymer's ability to form crystals, because each methyl group takes up space and constrains backbone bending.

Like most other vinyl polymers, useful polypropylene cannot be made by radical polymerization due to the higher reactivity of the allylic hydrogen (leading to dimerization) during polymerization. Moreover, the material that can result from such a process can have methyl groups arranged randomly, so called atactic PP. The lack of long-range order prevents any crystallinity in such a material, giving an amorphous material with very little strength and only specialized qualities suitable for niche end uses.

A Ziegler-Natta catalyst is able to limit incoming monomers to a specific orientation, only adding them to the polymer chain if they face the right direction. Most commercially available polypropylene is made with such Ziegler-Natta catalysts, which produce mostly isotactic polypropylene. With the methyl group consistently on one side, such molecules tend to coil into a helical shape; these helices then line up next to one another to form the crystals that give commercial polypropylene many of its desirable properties.

More precisely engineered Kaminsky catalysts have been made, which offer a much greater level of control. Based on metallocene molecules, these catalysts use organic groups to control the monomers being added, so that a proper choice of catalyst can produce isotactic, syndiotactic, or atactic polypropylene, or even a combination of these. Aside from this qualitative control, they allow better quantitative control, with a much greater ratio of the desired tacticity than previous Ziegler-Natta techniques. They also produce narrower molecular weight distributions than traditional Ziegler-Natta catalysts, which can further improve properties.

To produce a rubbery polypropylene, a catalyst can be made which yields isotactic polypropylene, but with the organic groups that influence tacticity held in place by a relatively weak bond. After the catalyst has produced a short length of polymer which is capable of crystallization, light of the proper frequency is used to break this weak bond, and remove the selectivity of the catalyst so that the remaining length of the chain is atactic. The result is a mostly amorphous material with small crystals embedded in it. Since each chain has one end in a crystal but most of its length in the soft, amorphous bulk, the crystalline regions serve the same purpose as vulcanization.

Melt processing of polypropylene can be achieved via extrusion and molding. Common extrusion methods include production of melt blown and spun bond fibers to form long rolls for future conversion into a wide range of useful products such as face masks, filters, nappies and wipes. The most common shaping technique is injection molding, which is used for parts such as cups, cutlery, vials, caps, containers, housewares and automotive parts such as batteries. The related techniques of blow molding and injection-stretch blow molding are also used, which involve both extrusion and molding.

The large number of end use applications for PP is often possible because of the ability to tailor grades with specific molecular properties and additives during its manufacture. For example, antistatic additives can be added to help PP surfaces resist dust and dirt. Many physical finishing techniques can also be used on PP, such as machining Surface treatments can be applied to PP parts in order to promote adhesion of printing ink and paints.

Since polypropylene is resistant to fatigue, most plastic living hinges, such as those on flip-top bottles, are made from this material. However, it is important to ensure that chain molecules are oriented across the hinge to maximize strength. Very thin sheets of polypropylene are used as a dielectric within certain high performance pulse and low loss RF capacitors.

High-purity piping systems are built using polypropylene. Stronger, more rigid piping systems, intended for use in potable plumbing, hydronic heating and cooling, and reclaimed water applications, are also manufactured using polypropylene. This material is often chosen for its resistance to corrosion and chemical leaching, its resilience against most forms of physical damage, including impact and freezing, and its ability to be joined by heat fusion rather than gluing.

Many plastic items for medical or laboratory use can be made from polypropylene because it can withstand the heat in an autoclave. Its heat resistance also enables it to be used as the manufacturing material of consumer-grade kettles. Food containers made from it will not melt in the dishwasher, and do not melt during industrial hot filling processes. For this reason, most plastic tubs for dairy products are polypropylene sealed with aluminum foil (both heat-resistant materials). After the product has cooled, the tubs are often given lids made of a less heat-resistant material, such as LDPE or polystyrene. Such containers provide a good hands-on example of the difference in modulus, since the rubbery (softer, more flexible) feeling of LDPE with respect to PP of the same thickness is readily apparent. Rugged, translucent, reusable plastic containers made in a wide variety of shapes and sizes for consumers from various companies such as Rubbermaid and Sterilite are commonly made of polypropylene, although the lids are often made of somewhat more flexible LDPE so they can snap on to the container to close it. Polypropylene can also be made into disposable bottles to contain liquid, powdered or similar consumer products, although HDPE and polyethylene terephthalate are commonly also used to make bottles. Plastic pails, car batteries, wastebaskets, cooler containers, dishes and pitchers are often made of polypropylene or HDPE, both of which commonly have rather similar appearance, feel, and properties at ambient temperature.

Polypropylene is a major polymer used in nonwovens, with over 50% used for diapers or sanitary products where it is treated to absorb water (hydrophilic) rather than naturally repelling water (hydrophobic). Other interesting nonwoven uses include filters for air, gas and liquids where the fibers can be formed into sheets or webs that can be pleated to form cartridges or layers that filter in various efficiencies in the 0.5 to 30 micron range. Such applications can be seen in the house as water filters or air conditioning type filters. The high surface area and naturally hydrophobic polypropylene nonwovens are ideal absorbers of oil spills with the familiar floating barriers near oil spills on rivers.

A common application for polypropylene is as Biaxially Oriented polypropylene (BOPP). These BOPP sheets are used to make a wide variety of materials including clear bags. When polypropylene is biaxially oriented, it becomes crystal clear and serves as an excellent packaging material for artistic and retail products.

Polypropylene's most common medical use is in the synthetic, nonabsorbable suture Prolene, manufactured by Ethicon Inc.

Polypropylene is most commonly used for plastic moldings where it is injected into a mold while molten, forming complex shapes at relatively low cost and high volume, examples include bottle tops, bottles and fittings.

Recently it has been produced in sheet form and this has been widely used for the production of stationary folders, packaging and storage boxes. The wide color range, durability and resistance to dirt make it ideal as a protective cover for papers and other materials. It is used in Rubik's cube stickers because of these characteristics.

Expanded Polypropylene (EPP) is a foam form of polypropylene. EPP has very good impact characteristics due to its low stiffness; this allows EPP to resume its shape after impacts. EPP is extensively used in model aircraft and other radio controlled vehicles by hobbyists. This is mainly due to its ability to absorb impacts, making this an ideal material for RC aircraft for beginners and amateurs.

Silicon Dioxide ($SiO_2$)

The chemical compound silicon dioxide, also known as silica, is an oxide of silicon with a chemical formula of $SiO_2$. Oxides of silicon, commonly referred to as "SiOx," include silicon dioxide. Silica is most commonly found in nature as sand or quartz, as well as in the cell walls of diatoms. It is a principal component of most types of glass and substances such as concrete. Silica is the most abundant mineral in the Earth's crust.

$SiO_2$ has a number of distinct crystalline forms in addition to amorphous forms. With the exception of stishovite and fibrous silica, all of the crystalline forms involve tetrahedral $SiO_4$ units linked together by shared vertices in different arrangements. Silicon-oxygen bond lengths vary between the different crystal forms. In a-quartz the Si—O—Si angle is 144°. The only stable form under normal conditions is a-quartz and this is the form in which crystalline silicon dioxide is usually encountered.

Silicon dioxide is formed when silicon is exposed to oxygen (or air). A very thin layer (approximately 1 nm or 10 Å) of so-called 'native oxide' is formed on the surface when silicon is exposed to air under ambient conditions. Higher temperatures and alternative environments are used to grow well-controlled layers of silicon dioxide on silicon, for example at temperatures between 600 and 1200° C., using the so-called "dry" or "wet" oxidation with $O_2$ or $H_2O$, respectively. The thickness of the layer of silicon replaced by the dioxide is 44% of the thickness of the silicon dioxide layer produced. Alternative methods used to deposit a layer of SiO2 include: Low temperature oxidation (400-450° C.) of silane; Decomposition of tetraethyl orthosilicate (TEOS) at 680-730° C.; Plasma enhanced chemical vapor deposition using TEOS at about 400° C.; Polymerization of tetraethyl orthosilicate (TEOS) at below 100° C. using amino acid as catalyst.

Pyrogenic silica (sometimes called fumed silica or silica fume), which is a very fine particulate form of silicon dioxide, is prepared by burning SiCl4 in an oxygen rich hydrocarbon flame to produce a "smoke" of $SiO_2$. Amorphous silica, silica gel, is produced by the acidification of solutions of sodium silicate to produce a gelatinous precipitate that is then washed and then dehydrated to produce colorless microporous silica.

Aluminum Oxide ($Al_2O_3$)

Aluminum oxide is an amphoteric oxide of aluminum with the chemical formula $Al_2O_3$. It is also commonly referred to as alumina, corundum, sapphire, ruby or aloxite. Aluminum oxide is an electrical insulator but has a relatively high thermal conductivity (40 $Wm^{-1}K^{-1}$) for a ceramic material. In its most commonly occurring crystalline form, called corundum or a-aluminum oxide, its hardness makes it suitable for use as an abrasive and as a component in cutting tools. Aluminum oxide is responsible for resistance of metallic aluminum to weathering. Metallic aluminum is very reactive with atmospheric oxygen, and a thin passivation layer of alumina (4 nm thickness) forms in about 100 picoseconds on any exposed aluminum surface. This layer protects the metal from further oxidation. The thickness and properties of this oxide layer can be enhanced using a process called anodizing. A number of alloys, such as aluminum bronzes, exploit this property by including a proportion of aluminum in the alloy to enhance corrosion resistance. The alumina generated by anodizing is typically amorphous, but discharge assisted oxidation processes such as plasma electrolytic oxidation result in a significant proportion of crystalline alumina in the coating, enhancing its hardness. The most common form of crystalline alumina, a-aluminum oxide, is known as corundum. Alumina also exists in other phases. Each has a unique crystal structure and properties. Aluminum hydroxide minerals are the main component of bauxite, the principal ore of aluminum. Alumina tends to be multi-phase; e.g., constituting several of the alumina phases rather than solely corundum.

Polyvinyl Alcohol (PVOH, PVA, or PVAL)

Polyvinyl alcohol (PVOH, PVA, or PVAL) is a water-soluble synthetic polymer. Polyvinyl alcohol has excellent film forming, emulsifying, and adhesive properties. It is also resistant to oil, grease and solvent. It is odorless and non-toxic. It has high tensile strength and flexibility, as well as high oxygen and aroma barrier properties. However these properties are dependent on humidity, in other words, with higher humidity more water is absorbed. The water, which acts as a plasticizer, will then reduce its tensile strength, but increase its elongation and tear strength. PVA is fully degradable and is a quick dissolver. PVA has a melting point of 230° C. and 180-190° C. for the fully hydrolyzed and partially hydrolyzed grades, respectively. It decomposes rapidly above 200° C. as it can undergo pyrolysis at high temperatures.

PVA is an atactic material but exhibits crystallinity as the hydroxyl groups are small enough to fit into the lattice without disrupting it. Unlike most vinyl polymers, PVA is not prepared by polymerization of the corresponding monomer. The monomer, vinyl alcohol, almost exclusively exists as the tautomeric form, acetaldehyde. PVA instead is prepared by partial or complete hydrolysis of polyvinyl acetate to remove acetate groups.

Nanopolymers

Polymer nanocomposite (PNC) is a polymer or copolymer having dispersed in its nanoparticles. These may be of different shape (e.g., platelets, fibers, spheroids), but at least one dimension is in the range of 1 to 50 nm. The transition from micro- to nano-particles leads to changes in physical as well as chemical properties. Two of the major factors in this are the increase in the ratio of the surface area to volume, and the size of the particle. The increase in surface area-to-volume ratio, which increases as the particles get smaller, leads to an increasing dominance of the behavior of atoms on the surface area of particle over that of those interior of the particle. This affects the properties of the particles when they are reacting with other particles. Because of the higher surface area of the nano-particles the interaction with the other particles within the mixture is more and this increases the strength, heat resistance etc. and many factors do change for the mixture.

An example of a nanopolymer is silicon nanospheres which show quite different characteristics. The particle size is 40-100 nm and it is much harder than silicon (a hardness between that of sapphire and diamond). Many technical applications of biological objects like proteins, viruses or bacteria such as chromatography, optical information technology, sensors, catalysis and drug delivery require their immobilization. Carbon nanotubes, gold particles and synthetic polymers are used for this purpose. This immobilization has been achieved predominantly by adsorption or by chemical binding and to a lesser extent by incorporating these objects as guests in host matrices. In the guest host systems, an ideal method for the immobilization of biological objects and their integration into hierarchical architectures should be structured on a nanoscale to facilitate the interactions of biological nano-objects with their environment. Due to the large number of natural or synthetic polymers available and the advanced techniques developed to process such systems to nanofibers, rods, tubes etc. make polymers a good platform for the immobilization of biological objects.

Polymer fibers are, in general, produced on a technical scale by extrusion, e.g., a polymer melt or a polymer solution is pumped through cylindrical dies and spun/drawn by a take-up device. The resulting fibers have diameters typically on the 10-μm scale or above. To come down in diameter into the range of several hundreds of nanometers or even down to a few nanometers, electrospinning is today still the leading polymer processing technique available. A strong electric field of the order of 103 V/cm is applied to the polymer solution droplets emerging from a cylindrical die. The electric charges, which are accumulated on the surface of the droplet, cause droplet deformation along the field direction, even though the surface tension counteracts droplet evolution. In supercritical electric fields, the field strength overbears the surface tension and a fluid jet emanates from the droplet tip. The jet is accelerated towards the counter electrode. During this transport phase, the jet is subjected to strong electrically driven circular bending motions that cause a strong elongation and thinning of the jet, a solvent evaporation until, finally, the solid nanofiber is deposited on the counter electrode.

Electro spinning, co-electrospinning, and the template methods based on nanofibers yield nano-objects which are, in principle, infinitively long. For a broad range of applications including catalysis, tissue engineering, and surface modification of implants this infinite length is an advantage. But in some applications like inhalation therapy or systemic drug delivery, a well-defined length is required. The template method to be described in the following has the advantage such that it allows the preparation of nanotubes and nanorods with very high precision. The method is based on the use of well-defined porous templates, such as porous aluminum or silicon. The basic concept of this method is to exploit wetting processes. A polymer melt or solution is brought into contact with the pores located in materials characterized by high energy surfaces such as aluminum or silicon. Wetting sets in and covers the walls of the pores with a thin film with a thickness of the order of a few tens of nanometers. This process happens typically within a minute for temperatures about 50 K above the melting temperature or glass transition temperature, even for highly viscous polymers, such as, for instance, polytetrafluoroethylene, and this holds even for pores with an aspect ratio as large as 10,000. To obtain nanotubes, the polymer/template system is cooled down to room temperature or the solvent is evaporated, yielding pores covered with solid layers. The resulting tubes can be removed by mechanical forces for tubes up to 10 μm in length, e.g., by just drawing them out from the pores or by selectively dissolving the template. The diameter of the nanotubes, the distribution of the diameter, the homogeneity along the tubes, and the lengths can be controlled.

The size-dependent and pressure-dependent glass transition temperatures of free-standing films or supported films having weak interactions with substrates decreases with decreasing of pressure and size. However, the glass transition temperature of supported films having strong interaction with substrates increases of pressure and the decrease of size.

Nanocomposites are polymer structures that contain fillers, typically silicate nanoclays, with at least one dimension in the nanometer range. The fillers separate into tiny platelets that disperse into a matrix of layers. Because the matrix of layers creates a tortuous path for gasses trying to permeate through the film, the barrier properties of the modified polymer are improved. However, the challenge is to ensure that that the filler dispersion is consistent. In addition to better barrier properties, nanocomposites modified films also have improved dimensional stability and stiffness and, because crystallinity is increased, enhanced clarity. Nanocomposite masterbatches are commercially available for nylon and polyolefins. The oxygen barrier of nylon nanocomposite films can be as much as 50 percent higher than a nonmodified nylon. Polyethylene and polypropylene nanocomposite structures have shown improvement in gas barrier of 25 to 50 percent and in water vapor of 10 to 15 percent in laboratory settings. Achieving consistent barrier properties on a commercial scale remains challenging. Nanocomposite technology is very much an emerging science. It shows a great deal of promise and as more options become available for film applications it will have a significant impact on barrier material options.

Saran

Saran is the trade name for a number of polymers made from vinylidene chloride (especially polyvinylidene chloride or PVDC), along with other monomers. Saran film has a very low permeability to water vapor, flavor and aroma molecules, and oxygen compared to other plastics. The barrier to oxygen prevents food spoilage, and the barrier to flavor and aroma molecules helps food retain its flavor and aroma. Saran also possesses gas barrier properties.

Polytrimethylene Terephthalate (PTT)

Polytrimethylene Terephthalate (PTT) is a semi crystalline polymer that has many of the same advantages as PET. PTT exhibits good tensile strength, flexural strength, and stiffness. It has excellent flow and surface finish. PTT can have more uniform shrinkage and better dimensional stability in some applications than competing semicrystalline materials. PTT has excellent resistance to a broad range of chemicals at room temperature, including aliphatic hydrocarbons, gasoline, carbon tetrachloride, perchloroethylene, oils, fats, alcohols, glycols, esters, ethers and dilute acids and bases. Strong bases may attack PTT compounds. Impact modifiers and reinforcing fibers (long glass, short glass, or carbon) can be used to increase the impact properties, as well as the strength and stiffness of PTT.

Polytrimethylene Naphthalate (PTN)

Poly(trimethylene phthalates or naphthalate) and copolymers are aromatic polyesters made by polycondensation of 1,3-propanediol (PDO) and terephthalic acid (PTT), isophthalic acid (PTI) or naphthalic acid (PTN) and/or with comonomers (isophthalic acid, 1,4-butanediol, etc.). Films of PTN possess good barrier properties.

Polyethylene Naphthalate (PEN)

Polyethylene naphthalate (PEN) is a polyester with good barrier properties (even better than polyethylene terephthalate). Because it provides a very good oxygen barrier, it is particularly well-suited for bottling beverages that are susceptible to oxidation, such as beer. It is prepared from ethylene glycol and one or more naphthalene dicarboxylic acids by condensation polymerization.

Polyurethane

A polyurethane is any polymer consisting of a chain of organic units joined by urethane (carbamate) links. Polyurethane polymers are formed through step-growth polymerization by reacting a monomer containing at least two isocyanate functional groups with another monomer containing at least two hydroxyl (alcohol) groups in the presence of a catalyst. Polyurethane formulations cover an extremely wide range of stiffness, hardness, and densities. Though the properties of the polyurethane are determined mainly by the choice of polyol, the diisocyanate exerts some influence, and must be suited to the application. The cure rate is influenced by the functional group reactivity and the number of functional isocyanate groups. The mechanical properties are influenced by the functionality and the molecular shape. The choice of diisocyanate also affects the stability of the polyurethane upon exposure to light. Polyurethanes made with aromatic diisocyanates yellow with exposure to light, whereas those made with aliphatic diisocyanates are stable. Softer, elastic, and more flexible polyurethanes result when linear difunctional polyethylene glycol segments, commonly called polyether polyols, are used to create the urethane links. This strategy is used to make spandex elastomeric fibers and soft rubber parts, as well as foam rubber. More rigid products result if polyfunctional polyols are used, as these create a three-dimensional cross-linked structure which, again, can be in the form of a low-density foam.

Polyether Block Amide (PEBAX®)

Polyether block amide is a thermoplastic elastomer or a flexible polyamide without plasticizer consisting of a regular linear chain of rigid polyamide segments and flexible polyether segments.

Parylene C

Parylene is the trade name for a variety of chemical vapor deposited poly(p-xylylene) polymers used as moisture barriers and electrical insulators. Among them, Parylene C is the most popular due to its combination of barrier properties, cost, and other manufacturing advantages.

Silicone

Silicones, also referred to as polymerized siloxanes or polysiloxanes, are mixed inorganic-organic polymers with the chemical formula $[R_2SiO]_n$, where R is an organic group such as methyl, ethyl, or phenyl. These materials consist of an inorganic silicon-oxygen backbone ( . . . —Si—O—Si—O—Si—O— . . . ) with organic side groups attached to the silicon atoms, which are four-coordinate. In some cases organic side groups can be used to link two or more of these —Si—O— backbones together. By varying the —Si—O— chain lengths, side groups, and crosslinking, silicones can be synthesized with a wide variety of properties and compositions. They can vary in consistency from liquid to gel to rubber to hard plastic. The most common siloxane is linear polydimethylsiloxane (PDMS), a silicone oil. The second largest group of silicone materials is based on silicone resins, which are formed by branched and cage-like oligosiloxanes.

Fabrication of the Composite Wall

The various layers of the composite wall, including the gas barrier layers, need not be situated in any particular order, but those of superior resistance to acidity, temperature, mechanical abrasion, and superior biocompatibility profile are preferably employed as layers contacting the gastric environment. Those with superior resistance to, e.g., acidity and temperature, are preferably employed as layers contacting the central lumen of the balloon.

The various layers of the wall can include a single layer or up to 10 or more different monolayers; however, a film thickness of from 0.001 inches (0.0254 cm) to 0.004 inches (0.010 cm) thick is desirable such that the resulting balloon compacted to fit into a swallowable capsule. The resulting composite wall preferably has good performance specifications with respect to each category listed in Tables 1a-b.

Films that are co-extruded are advantageously employed, as some adhesives may contain leachables that are undesirable from a biocompatibility perspective. In addition, coextrusion allows for better blending such that the materials maintain their original properties when combined in this fashion and are less likely to be subject to delamination when exposed to gastric motility forces.

Combining films with similar properties, e.g., two film layers with excellent gas barrier properties, in a composite wall is advantageous for use in a gastric balloon containing nitrogen, oxygen, $CO_2$ or a mixture thereof as the inflation gas or where the external environment the product is to be placed in, contains a mixture of gases including $CO_2$, e.g., the stomach. A primary advantage of such composite films is that restrictions on film thickness can be observed without sacrifice of gas barrier properties. Such a configuration also contributes to reducing the effects of processing damage (e.g., manufacturing and compacting) and damage due to exposure to in vivo conditions (e.g., gastric motility forces).

In a particularly preferred embodiment, the composite wall includes a plurality of layers. The first layer is an outer protective layer that is configured for exposure to the gastric environment. This layer is resistant to mechanical forces, exposure to water (vapor), abrasion, and high acidity levels. Nylon or more specifically, Nylon 12 is particularly preferred for the layer exposed to the gastric environment, and is especially resistant to mechanical forces.

In an alternative embodiment, polyurethane is RF welded to saran to yield a 6-7 mil thick composite wall. In another embodiment, a five layer system is provided comprising a layer of saran sandwiched between two polyurethane layers. Between the saran layer and each of the polyurethane layers is a tie layer. The layers can be welded together, co-extruded or adhered using an adhesive. This tri-layer is then co-extruded to Nylon on each side, and then a final sealing layer (polyethylene or the like) is added to one of the nylon layers for the total composite wall. A representative example of material combinations that are commercially available or manufacturable is provided in Table 2. The orientation of the layers (innermost—in contact with the central balloon lumen, or outermost—in contact with the gastric environment) is also indicated if more than two layers are described to support a suggested composite wall.

Most of the film resins listed in Table 2 provide some degree of gas barrier properties. Therefore, many can be used solely to form the balloon wall as a monolayer film; however they can also be used in conjunction with other film resins to meet the desired gas retention and mechanical specifications for the useful life of the balloon based on the inflation gas and external environment the balloon is to be placed in. These film resins can also be coated with gas barrier coatings listed in Tables 1a-b. Additional film layers can be added to form the total composite wall. While such additional layers may not impart substantial barrier properties, they can provide structural and/or mechanical properties, protection for the other layers of the composite wall that are susceptible to water vapor, humidity, pH, or the like, or other desirable properties. The film layers can be assembled using various adhesives, via co-extrusion, via lamination, and/or using tie layers and such to create a composite wall that meets the requirements of an intragastric balloon suitable for use for at least 25 days, or up to 90 days or more, with the specified gas retention properties. Table 2 provides a list of layers and layer combinations suitable for use in composite walls for an intragastric balloon. The composite description, resin abbreviation, configuration (single layer, bilayer, trilayer, or the like) and trade name of commercially available combinations are listed. The number of layers indicated does not include any adhesive layers or tie layers used to fabricate the composite wall, such that a 6-layer composite wall may, for example, have two or three adhesive layers and/or tie layers that make up the total composite wall, and therefore the total number of layers can be eight or nine in final form. The term "layer" as used herein is a broad term, and is to be given its ordinary and customary meaning to a person of ordinary skill in the art (and is not to be limited to a special or customized meaning), and refers without limitation to a single thickness of a homogenous substance (e.g., a coating such as SiOx, or a layer such as PET), as well as to a supporting layer having a coating thereon (wherein a "coating" is, e.g., a material typically employed in conjunction with substrate that provides structural support to the coating layer). For example, a PET-SiOx "layer" is referred to herein, wherein a layer of Si-Ox is provided on a supporting PET layer.

TABLE 2

| Example Film Composite Walls* | Abbreviation | Trade name |
| --- | --- | --- |
| polyethylene terephthalate | PET | Mylar |
| metalized oriented polyethylene terephthalate | metalized OPET | Custom |
| polyvinyl alcohol coated oriented polypropylene | PVOH coated OPP | Bicor |
| metalized biaxially oriented nylon 6 | metalized OPA6 | Custom |
| Biaxally oriented Nylon/ ethylene vinyl alcohol/ biaxially oriented Nylon | OPA/EVOH/ OPA | Honeywell Oxyshield Plus |
| Nylon/ethylene vinyl alcohol/Low Density Polyethylene | Nylon/EVOH/ LDPE | Custom |
| polyvinylidene chloride coated oriented polyethylene terephthalate | PVDC/OPET | Mylar |
| polyvinylidene chloride coated oriented polypropylene | PVCD/OPP | Custom |
| polyvinylidene chloride coated biaxially oriented | PVCD/OPA6 | Honeywell Oxyshield |

TABLE 2-continued

| Example Film Composite Walls* | Abbreviation | Trade name |
|---|---|---|
| Nylon 6 high density polyethylene/ ethylene vinyl alcohol | HDPE/EVOH | Custom |
| polypropylene/ethylene vinyl alcohol laminate | PP/EVOH | Custom |
| polyethylene terephthalate/ ethylene vinyl alcohol | PET/EVOH | Custom |
| metalized oriented polypropylene | metalized OPP | Custom |
| sealable PVDC coated oriented polypropylene | PVDC coated PP | Custom |
| polyvinylidene fluoride | PVDF | Custom |
| Polyvinyl chloride | PVC | Custom |
| polyvinyl fluoride | PVF | Tedlar |
| polychlorofluoroethylene | PCTFE | ACLAR UltRx, SupRx, Rx |
| amine-based epoxy coated Nylon | epoxy coated PA6 | Bairocade |
| polyvinyl chloride-polyvinylidene chloride copolymer | PVC-PVDC | Custom |
| medium density polyethylene | MDPE | Custom |
| Nylon/Polypropylene | Nylon/PP laminate | Custom |
| Nylon-High Density Polyethylene | Nylon-HDPE laminate | Custom |
| Nylon 12/Ethyl Methyl Acrylate/Polyvinylidene Chloride/Ethyl Methyl Acrylate/ | Co-extruded Nylon 12-encapsulated | Custom Co-extruded blend |
| Nylon 12/Linear Low Density Polyethylene + Low Density Polyethylene | PVDC-Nylon 12-LLDPE + LDPE | Custom |
| Multi-layer Nylon 12/Linear Low Density Polyethylene + Low Density Polyethylene | Co-extruded multi-layer Nylon 12-LLDPE + LDPE | Custom Co-Extruded Blend |
| acetylene plasma coating on polyester | PET/A | Custom |
| difluoroethylene coating on polyethylene terephthalate | PET/DA | Custom |
| oriented polypropylene | OPP | Custom |
| cast propylene | CPP | Custom |
| high density polyethylene | HDPE | Custom |
| cyclic olefin copolymer | COC | Custom |
| oriented polystyrene | OPS | Custom |
| Fluorinated Ethylene Propylene | FEP | Custom |
| difluoroethylene coating on low density polyethylene | LDPE/D | Custom |
| difluoroethylene coating on polypropylene | PP/D | Custom |
| acetylene plasma coating on polypropylene | PP/A | Custom |
| acetylene plasma coating on low density polyethylene | LDPE/A | Custom |
| polybutylene terephthalate polyether glycol copolymer | TPC-ET | Hytrel |
| polyether block amide TPE | PEBA | Pebax |
| oxide coated biaxially oriented Nylon | oxide coated PA | Honeywell Oxyshield Ultra |
| Nanoclay/nylon | MXD6/ Nanoclay | Imperm/Aegis OXCE |
| Polyethylene Terephthalate/ Silicone Dioxide | PET/SiOx | BestPET/ TechBarrier |
| Polyethylene Terephthalate/ Oxygen scavengers | PET + O2 Scavengers | MonoxBar |
| Modified Polyethylene Terephthalate | Modified PET | DiamondClear |
| Polyethylene Terephthalate/ Nylon 6 | PET/MXD6 | HP867 |
| Amorphous polyvinyl alcohol | Amorphous PVOH | Nichigo G-Polymer |
| Nylon 6/Ethyl vinyl alcohol/ Linear Low Density Polyethylene | Nylon 6/EVOH/ LLDPE | Custom |
| Ethyl vinyl alcohol/Poly-Propylene/Ethyl vinyl alcohol | EVOH/PP/EVOH | Custom |
| Ethyl vinyl alcohol/Nylon | EVOH/Nylon | Custom |
| Polyethylene/Ethyl vinyl alcohol/Polyethylene | PE/EVOH/PE | Custom |
| Polyethylene/Ethyl vinyl alcohol/Polyethylene Terephthalate | PE/EVOH/PET | Custom |
| Silicon dioxide-coated Polyethylene Terephthalate/ Linear Low Density Polyethylene/ Ethyl vinyl alcohol/Linear Low Density Polyethylene | PET-SiOx/ LLDPE/EVOH/ LLDPE | Custom |
| Aluminum Oxide-coated Polyethylene Terephthalate/ Polyethylene | PET-Al₂O₃/ LLDPE | Custom |
| Polyethylene/Ethyl vinyl alcohol/Linear Low Density Polyethylene | PE/EVOH/ LLDPE | Custom |
| Polyethylene Terephthalate/ Polyethylene/Polyethylene/Bi-axially oriented Ethyl vinyl alcohol | PET/PE/ OEVOH/PE | Custom |
| Polyethylene Terephthalate/ Polyethylene/Ethyl vinyl alcohol/Ethyl vinyl alcohol/ Ethyl vinyl alcohol/ Polyethylene | PET/PE/ EVOH/EVOH/ EVOH/PE | Custom |
| Polyethylene Terephthalate/ Polyethylene/Nylon 6/Ethyl vinyl alcohol/Nylon 6/ Polyethylene | PET/PE/ Nylon 6/ EVOH/Nylon 6/PE | Custom |
| Silicon dioxide-coated Polyethylene Terephthalate/ Polyethylene/Ethyl vinyl alcohol/Polyethylene | PET-SiOx/ PE/EVOH/ PE | Custom |
| Polyethylene/Ethyl vinyl alcohol/polyvinylchloride | PE/EVOH/ PVDC | Custom |
| Polyethylene Terephthalate/ Linear Low Density Polyethylene/Ethyl vinyl alcohol/Linear Low Density Polyethylene | PET/LLDPE/ EVOH/ LLDPE | Custom |
| Kurrarister C-coated Polyethylene Terephthalate/ Polyethylene/ Ethyl vinyl alcohol/Polyethylene | PET-Kurrarister-C/PE/ EVOH/PE | Custom |
| Polyethylene Terephthalate/ Polyethylene/Nylon 6/Ethyl vinyl alcohol/Nylon 6/ Polyethylene | PET/PE/ Nylon 6/ EVOH/Nylon 6/PE | Custom |
| Nylon 6/Ethyl vinyl alcohol/ Polyvinylchloride/Low Density Polyethylene | Nylon 6/EVOH/ PVDC/Nylon 6/LDPE | Custom |
| Polyimide | PI | Custom |
| Polyimide/Linear Low Density Polyethylene | PI/LLDPE | Custom |
| Polyimide/Polyvinylchloride | PI/PVdC | Custom |
| Polyimide/Polyvinylchloride/ Linear Low Density Polyethylene | PI/PVdC/ LLDPE | Custom |

In particularly preferred embodiments, the composite wall has a thickness of 0.005 inches or less (5.0 mil or less); however, in certain embodiments a thicker composite wall may be acceptable. Generally it is preferred that the composite wall have a thickness of no more than 0.004 inches (4.0 mil).

Fabrication of the Balloon

To ensure good mechanical strength of the balloon, the balloon is preferably thermoformed and sealed such that the edges of the pieces used to form the balloon are overlapping. This can be accomplished by any suitable method. For example, two flat sheets of material can be placed in a frame with magnetized edges to hold the two sheets in place. Slack can be added to the piece of film to orient the material such that it maintains its properties after the thermoforming process. The frame can be placed over a mold that represents a hemisphere the balloon. A heater (e.g., a 4520 watt infrared heater) can be used to form the material, and a vacuum can be pulled. The material, with slack put in it prior to vacuum being applied, re-orients the material such that it is more evenly distributed around the hemisphere shape. The material is preferably thickest in the middle and is made thinner on the sides where it will be welded to a second piece to create a sphere or ellipsoid having a substantially uniform wall thickness. For example, starting with a 0.0295" film, the middle of the film or subsequent apex has an ending film thickness of 0.0045" and the edges have an ending thickness of 0.0265" for subsequent overlapping during the welding process.

The valve can be adhered to the (e.g., polyethylene, PE) side of one of the hemispheres and protrude out of the opposite (e.g., nylon) side. One hemisphere typically consists of Nylon as the outermost layer and the second hemisphere typically has polyethylene (sealing web) as the outermost layer. The edges of the two hemispheres are preferably aligned such that they overlap by at least 1 mm and no more than 5 mm. Alignment and overlay of the two hemispheres is done to compensate for the thinning at the edges during the thermoforming process, which in turn inhibits seam bursts in vivo. Each half of the spheroid is placed on a fixture and the excess from the thermoforming process is trimmed. On a multi-layer film, the sealing layer, a PE or similar layer is bonded to the sealing layer of the second film half. To do this the film of the hemisphere that has the nylon exposed to the external environment is folded up along the edges of the sphere on one half such that it can be bonded to the hemisphere with the polyethylene on the outermost layer.

The two film pieces are then sealed using a roller bonder or a band heater. In the roller bonder, the air provides the compression, the heater provides the sealing heat, and a motor that moves the bonder around the area controls the time that is required to ensure proper sealing. In the band heater, there is a heating element, an expandable plug that provides the compression, and a timer. The band is a metal, preferably copper and a spool-like fixture provides the compression needed. Using film layers of different melt temperatures helps ensure integrity of the barrier layers of the final balloon configuration. If two similar materials are welded, then an insulator can be employed. In a preferred embodiment, one sphere is provided with the Nylon layer facing out and the second sphere has a PE layer facing out.

Balloons with Resistance to Spontaneous Deflation

The largest percentage of intragastric balloon malfunctions is due to spontaneous deflations. Spontaneous deflations can occur due to (1) external puncture of the intragastric balloon due to gastric motility forces, (2) over inflation of the balloon due to increased internal pressure of the balloon from uptake of the gastric environment of the gasses and water vapor and (3) under inflation of the balloon that leads to fatiguing of the excess material and subsequent puncture of the balloon. By managing these two variables and tuning these variables to withstand the dynamic gastric environment, the balloon system can be tailored to ensure it remains inflated throughout its useful life. Instances of spontaneous deflation in this intragastric balloon can be minimized by selection of the starting inflation gas in conjunction with selection of the composite wall materials and construction. Selection of the permeability characteristics with respect to water vapor transmission and gas permeability of the composite wall so as to take advantage of the properties of the gastric space contents can enable the rate of diffusion of gases into and out of the balloon to be controlled. This method allows for a tunable method for prevention of under inflation and over inflation.

Another phenomenon seen with gastric balloons and obesity in general is stomach accommodation. In the process of stomach accommodation, the stomach grows to accommodate the space occupying device or excess food that is ingested. In the process of stomach accommodation, the volume of a stomach containing an intragastric balloon grows over time, such that the patient becomes hungrier. However, by controlling gas diffusion and water vapor transmission across the balloon wall over time, the balloon size can also be increased over time by selecting the starting inflation gas(es) and water and other in vivo gas permeability characteristics of the film so as to maintain weight loss. In addition to spontaneous deflations, selecting the permeability characteristics of the composite wall in conjunction with the starting gases and utilizing the transfer of gases and water inside of the balloon from the gastric environment, the balloon can be designed to grow over its useful life in response to stomach accommodation.

Experiments were performed wherein various starting inflation gases were selected in conjunction with varying external gas environments that mimic the stomach gas and water environment in vivo. The stomach environment consists of water, acid (hydrochloric acid), a mixture of gases, and chyme (the semifluid mass of partly digested food expelled by the stomach into the duodenum). Stomach gas usually arises from swallowing air during eating. The composition of air is nitrogen ($N_2$) 78.084%; oxygen ($O_2$) 20.9476%; argon (Ar) 0.934%; carbon dioxide ($CO_2$) 0.0314%; neon (Ne) 0.001818%; methane ($CH_4$) 0.0002%; helium (He) 0.000524%; krypton (Kr) 0.000114%; hydrogen ($H_2$) 0.00005%; and xenon (Xe) 0.0000087%.

Five gases constitute greater than 99% of the gases in gastrointestinal system: $N_2$, $O_2$, $CO_2$, $H_2$ and methane, with nitrogen predominating. Gastric $pCO_2$ closely parallels local (splanchnic) arterial and draining venous blood $pCO_2$ values. Neutralization of stomach acid can also generate gas. For example, when the stomach acid reacts with bicarbonates (e.g., as are present in certain antacids) in the digestive juices, the chemical process creates $CO_2$, which is normally absorbed into the blood stream. Digestion of food in the intestines, mainly through fermentation by colonic bacteria, generates $CO_2$, $H_2$, and methane. Microbes appear to be the sole source of all of the hydrogen and methane produced in the intestine. These arise from fermentation and digestion of nutrients (polysaccharides from fruits and vegetables are not digested in the small intestines). Small quantities of a few other gases, including hydrogen sulfide, indoles, and ammonia can also be generated.

In certain embodiments, it is preferred that the composition of the initial fill gas is substantially characteristic of the composition of the mixture of gases in the in vivo gastric environment. Such an initial fill gas can include only $N_2$ and $CO_2$, or can include only $N_2$, $CO_2$, and $O_2$, or can include $N_2$ and $CO_2$ as well as one or more other gases present in the in vivo environment (e.g., water vapor, $H_2$, $CH_4$, Ar, $H_2S$, or $NH_3$). Argon or another inert gas (or inert gases) can be substituted in part or in whole for $N_2$, which is considered an inert gas in the context of the preferred embodiments. In those embodiments wherein the fill gas includes only $N_2$ or $CO_2$, it is preferred that the initial fill gas comprises from about 75% v/v to about 96% v/v $N_2$, from about 5% v/v to about 15% (vol.) $O_2$, and from about 1% v/v to about 10% v/v $CO_2$, more preferably from about 80% (vol.) to about 85% (vol.) $N_2$, from about 5% (vol.) to about 13% (vol.) $O_2$, and from about 4% (vol.) to about 8% (vol.) $CO_2$. In those embodiments wherein the fill gas includes only $N_2$ or $CO_2$, it is preferred that the initial fill gas comprises from about 4% (vol.) to about 8% (vol.) $CO_2$, with the remainder $N_2$ or another inert gas. In embodiments wherein the initial fill gas comprises other gases in addition to $CO_2$ and the inert gas(es), it is preferred that the initial fill gas comprises from about 4% (vol.) to about 8% (vol.) $CO_2$.

Controlled self-inflation of the intragastric balloon in the in vivo environment can be achieved by using a semi-permeable or permeable composite wall in the balloon and initially filling the balloon with a preselected single gas, such as $N_2$ or $O_2$. The balloon utilizes differences in concentrations of gases and water concentration differences between the internal balloon environment and the external environment in vivo (GI/stomach) to increase and/or decrease the volume and/or pressure over time. To achieve a controlled decrease in volume and/or pressure, a wall can be employed that has a relatively higher permeability to the single gas used to inflate the balloon than to other gases present in the in vivo gastrointestinal environment. For example, if nitrogen gas is employed as the inflation gas, over time in the in vivo environment, the volume and/or pressure in the balloon will decrease as nitrogen diffuses out into the in vivo environment through the oxygen permeable wall. Similarly, if oxygen gas is employed as the inflation gas, over time in the in vivo environment, the volume and/or pressure in the balloon will decrease as oxygen diffuses out into the in vivo environment through the oxygen permeable wall. The differential in partial pressure of the single gas in the balloon (higher) versus the in vivo environment (lower) will drive the process until equilibrium or homeostasis is reached. To achieve a controlled increase in volume and/or pressure, a wall can be employed that has a relatively lower permeability to the single gas used to inflate the balloon than to other gases present in the in vivo gastrointestinal environment. For example, if nitrogen gas is employed as the inflation gas, over time in the in vivo environment, the volume and/or pressure in the balloon will increase as $CO_2$, and all of the other gases present in the gastric environment, diffuse into the balloon through the $CO_2$ permeable wall. The differential in partial pressure of the permeable gas in the balloon (lower) versus the in vivo environment (higher) will drive the process until equilibrium is reached.

In addition, maintaining and/or controlling inflation of the balloon can also be done using the differences in concentrations between the internal balloon environment and external gastric environment in which the balloon volume/pressure can be increased or decreased as needed to extend the useful life of the product. One reason to decrease the pressure can be to first inflate the balloon with a large, but highly diffusible/soluble gas molecule such as $CO_2$ in addition to a more inert gas like nitrogen to pre-stretch the balloon, with the soluble gas diffusing out of the balloon and other gases not originally present in the balloon migrating in to fill the balloon.

Inflation gases can be selected to start with the majority of the gas in the balloon comprising a large, inert gas or a gas that has low diffusivity through the selected composite wall. Examples of inert gases include but are not limited to nitrogen, as well as $SF_6$, $C_2F_6$, $C_3F_8$, $C_4F_{10}$, $C_4F_8$, $C_4F_8$, $C_3F_6$, $CF_4$, and $CClF_2$—$CF_3$. An inert gas in conjunction with a less inert gas(es) that are more soluble in the gastric environment, can be combined to comprise the starting balloon inflation gas composition where the inert gas would be in excess to the more soluble/diffusible gas. Patient diet and medications can also affect/control balloon inflation status—primarily by $CO_2$ concentration effects produced in the gastric environment. In addition, gastric pH also affects $CO_2$ concentration. This particular method can also allow for a greater degree of tuning of the device's useful life based on the composite wall material, e.g., barrier/non-barrier and whether the gas that diffuses in is maintained longer in the balloon if it has a barrier wall versus a non-barrier wall. This particular form of self-inflation can be employed using a self-inflating gastric balloon (e.g., initially inflated by a gas generating reaction in the balloon initiated after swallowing), or an inflatable gastric balloon (e.g., inflated using a catheter, with or without endoscopic assistance, delivered nasogastrically or any other delivery method). The method can be used with any gastric balloon, including swallowable balloons and balloons placed in the stomach by, e.g., endoscopic methods. The method is particularly preferred for use in connection with intragastric devices; however, it can also be applied to use in, e.g., pulmonary wedge catheters and urinary incontinence balloon devices. The advantages to this technology include the ability to compensate for stomach accommodation, allowing the balloon to adapt to a stomach that may increase in volume over time, thereby maintaining patient satiety. It also permits starting with a smaller amount of inflation gas constituents for a self-inflating balloon. It can prevent spontaneous deflations by utilizing diffusion gradients between gastric balloon systems and the in vivo gastric environment.

In a particularly preferred embodiment, used in connection with $N_2$ (with or without $CO_2$) as the inflation agent, a multi-layer co-extruded blend for the wall layers is employed. A particularly preferred configuration is Nylon 12/Ethyl Methyl Acrylate/Polyvinylidene Chloride/Ethyl Methyl Acrylate/Nylon 12/Linear Low Density Polyethylene+Low Density Polyethylene (also referred to as co-extruded Nylon 12-encapsulated PVDC-Nylon 12-LLDPE+LDPE multilayer). Another particularly preferred configuration is a co-extruded multi-layer Nylon 12/Linear Low Density Polyethylene+Low Density Polyethylene. Selection of the resins for the composite wall construction (as well as selection of using a coextrusion method or adhesives) can be varied to control compliance (stretchiness), puncture resistance, thickness, adhesion, sealing bond strength, orientation, acid resistance, and permeability characteristics to gasses and water vapor to achieve a particular effect.

Automatic Deflation of Intragastric Balloon Systems

The self-inflating (also referred to as automatic inflating) or inflatable (also referred to as manually inflating) intragastric balloon is provided with mechanisms to reliably control timing of deflation. In preferred embodiments, the balloon auto-deflates and passes through the stomach, through the lower gastrointestinal tract, and out of the body at the end of its pre-determined useful life (non-spontaneous), preferably between 30 and 90 days but can be timed to deflate within 6 months. In the preferred embodiments described below, the timing of deflation can be accomplished via the external gastric environment (by conditions of temperature, humidity, solubility, and/or pH, for example) or via the environment within the lumen of the inflated balloon. It is preferable for consistency to control the initiation of the self-deflation process by manipulating the internal balloon environment.

In other embodiments, the patch applied to allow for inverted seams as described above and/or one or more additional patches or other structures added to the balloon construction are made out of an erodible, degradable, or dissolvable material (natural or synthetic) and are incorporated into the wall of the balloon. The patch(s) are of sufficient size to ensure opening of a sufficient surface area to cause rapid deflation, and to prevent re-inflation by seepage of stomach fluid into the balloon. The balloon patch(s) comprise materials that can be applied to the balloon such that a substantially smooth surface is maintained, and preferably comprise a single layer or multi-layered material. The patch(s) are constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), poly(lactide-co-glycolide) (PLG), polyglycolic acid (PGA), polycaprolactone (PCL), polyesteramide (PEA), polyhydroxyalkanoate (PHBV), polybutylene succinate adipate (PBSA), aromatic copolyesters (PBAT), poly (lactide-co-caprolactone) (PLCL), polyvinyl alcohol (PVOH), polylactic acid (PLA), poly-L-lactic acid PLAA, pullulan, polyethylene glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. Degradation/erosion occurs, is initiated by, and/or is controlled by the gastric environment (e.g., by conditions of temperature, humidity, solubility, and/or pH, for example), or is controlled within the lumen of the balloon (e.g., by conditions of humidity and/or derived pH, for example) based on what the patch is exposed to. Thickness of the polymer as well as environment which affects degradation and time of exposure can also facilitate degradation timing. Degradation/erosion are timed such that they occur once the pre-determined balloon useful life is completed (e.g., inflation is maintained for from 25 to 90 days in vivo in the stomach before degradation/erosion results in formation of an opening permitting deflation). As an alternative to (or in connection with) using an degradable material for the patch, the patch can comprise a similar fluid retention barrier film or the same film as the remaining wall of the balloon which is adhered to the balloon using a weak adhesive, or welded or adhered such that after a specified amount of time the patch delaminates from the applied area and allows for an opening for inflation fluid release for deflation. Or if deemed necessary for rapid deflation the entire balloon composite wall can be made of the erodible material. The mechanism of using an erodible material or a material that mechanically fails after a pre-specified time is be similar for all embodiments for deflation mechanisms described below as well. The timing of degradation or erosion can be controlled using the external gastric environment (e.g., by conditions of temperature, humidity, solubility, and/or pH, for example) and/or can be controlled by conditions within the lumen of the balloon (e.g., by conditions of humidity and/or pH of residual liquid in the balloon).

In other embodiments, a plug or plugs (optionally in conjunction another degradable retaining structure) can be incorporated into the balloon construction and can consist, all or in part, of an erodible, disintegrable, or otherwise degradable synthetic or natural polymer similar to those described above (e.g., PLGA, PLAA, PEG, or the like). The plug can be formed into various shapes (e.g., cylinder shape) to achieve various surface-to-volume ratios so as to provide a preselected and predictable bulk degradation pattern for the erodible polymer. The plug can incorporate a releasing mechanism that can be chemically initiated after degradation/erosion begins, such that the septum or plug material pops out of the balloon or falls inside of the balloon, thereby creating a passageway for fluid release and subsequent deflation of the balloon. Mechanical additions that can be used in conjunction with a plug include a degradable/erodible/disintegrable material that holds a plug (e.g., of a non-degradable or degradable material) in place or a compressed spring housed within the retaining structure or plug structure. More specifically one preferred embodiment to achieve deflation can comprise a housing, a radial seal, a solid eroding core, and a protective film attached to the external surface of the eroding core. The inside of the eroding core is exposed to the internal balloon liquid. The core creates a compressive force that holds the seal against the housing. As the core erodes, the compression between the housing and the radial seal is reduced until there is clearance between the housing and the seal. Once there is clearance, gas can move freely from the inside of the balloon to the outside environment. The seal can fall out of the housing and into the balloon. The diameter, length, and material types can be adjusted in order to create the deflation at a desired time point. Example materials for each component used to achieve this deflation mechanism can be as follows: Housing: Biocompatible structural material, capable of withstanding enough radial force to form an air tight seal. Possible materials include: polyethylene, polypropylene, polyurethane, UHMWPE, titanium, stainless steel, cobalt chrome, PEEK, or nylon; Radial Seal: The radial seal needs to be composed of a biocompatible elastic material, capable of providing liquid and gas barrier to acidic environments. Possible materials include: silicon, polyurethane, and latex; Eroding Core: The eroding core needs to be a material capable of breaking down at a predictable rate at given environmental conditions. Possible materials include: PLGA, PLA, or other polyanhydrides that are capable of losing integrity over time or any materials listed above that provide erodible characteristics.

For the spring mechanism, once the material degrades, the spring is released and/or the plug/septum is pulled into the balloon or pushed out of the balloon, thus releasing fluid once an orifice has been created by release of the spring mechanism and pushing out or pulling in of the plug.

Another preferred embodiment is comprised of a septum, moisture eroding material inside an inlet port, and moisture absorbing expansion material. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired timepoint, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

In certain embodiments, the balloon can incorporate one or more plugs in the wall of the balloon that contain a compressed pellet or gas releasing pellet. The pellet can be comprised of any combination of constituents that, when activated, emit $CO_2$ gas (e.g., sodium bicarbonate and citric acid, or potassium bicarbonate and citric acid, or the like). The pellet can be in tablet or rod form protected by an erodible, disintegrable, or degradable material that is preferably tissue-compatible and degrades into non-toxic products or that slowly hydrolyzes and/or dissolves similarly to the plugs and patches described above (e.g., poly(lactic-co-glycolic acid) (PLGA), polyvinyl alcohol (PVOH), polylactic acid (PLA), poly-L-lactic acid PLAA, Pullulan, Polyethylene Glycol, polyanhydrides, polyorthoesters, polyaryletherketones (PEEK), multi-block polyetheresters, poliglecaprone, polydioxanone, polytrimethylene carbonate, and other like materials). Degradation/erosion of the plug initiates the reaction of the two chemicals in the pellet and subsequently leads to formation of gas (e.g., $CO_2$). As sufficient gas is trapped or built up, sufficient pressure is eventually generated to push out the softened polymer material and create a larger channel for the $CO_2$ gas in the balloon to escape. External pressure applied by the stomach to the balloon (e.g., squeezing) can contribute to the process of creating a larger channel. Dimensions and properties of the plug (diameter, thickness, composition, molecular weight, etc.) comprised of the polymer drives the timing of degradation.

In other embodiments, plugs or patches of different shapes or sizes similar to those of the plugs described above can be employed within the balloon lumen in a multi-layer configuration including a semi-permeable membrane to facilitate balloon deflation. The plug or patch is made of similar degradable/erodible/dissolvable material as described above (e.g., poly(lactic-co-glycolic acid) (PLGA), polyvinyl alcohol (PVOH), polylactic acid (PLA), PLAA, pullulan, and other like materials) and contains a compartment enclosed by a semi-permeable membrane (impermeable to an osmolyte) that contains a concentrated solution of a solute or osmolyte (such as glucose, sucrose, other sugars, salts, or combination thereof). Once the plug or patch begins to degrade or erode, the water molecules move by osmosis down the water gradient from the region of greater water concentration to the region of lower water concentration across the semi-permeable membrane into the hypertonic solution in the compartment. The compartment containing the osmolyte swells and eventually bursts, pushing the membranes and the degraded plug or patch out, thereby allowing rapid gas loss through the newly created channels or areas.

In certain embodiments, a balloon composed of a septum, moisture eroding material inside an inlet port, and moisture absorbing expansion material is employed. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired time point has been reached, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

Another mechanism for self-deflation is to create a forced de-lamination scheme, which can provide a larger surface area to ensure rapid deflation. In, e.g., a balloon having a tri-layer wall, the outermost layer is substantially strong enough to hold the inflation fluid (e.g., polyethylene terephthalate (PET) or the like), the middle layer is comprised entirely of an erodible material (e.g., PVOH or the like) while the inner layer is comprised of a weaker material (e.g., polyethylene (PE) or the like). The PET or outermost layer is "scored" or hatched with erodible material to create small channels that erode over time. This creates channels such that the gastric fluid seeps into the balloon layers and starts degrading the fully erodible material. When the erodible layer degrades or dissolves, the material that composes the innermost layer also erodes, degrades or dissolves since it is not strong enough to withstand the gastric forces/environment on its own. The balloon then collapses on itself and eventually passes through the lower gastrointestinal tract. Having an erodible layer sandwiched between a strong and weak layer facilitates timing of erosion by creating a longer path length than an erodible plug or patch affected by the gastric environment. The distance between scores or openings can also be selected so as to provide a desired deflation rate.

In another embodiment providing abrupt deflation of the balloon after a desired period of time has elapsed, the composite wall of the entire balloon or a section of the composite wall (patch) includes several material layers that are slowly penetrated by water that has been injected inside the balloon during the manufacturing process or during the inflation process. This water penetrates through the layers, eventually reaching a material that substantially expands, rupturing a thin external protective later, and creating a large hole for gas to escape and the balloon to deflate. The water expanding material is protected from liquid via a coating or sheath, such as parylene, which allows a controllable amount of moisture exposure. Once water reaches the expansion material, it exerts a force on the protective outer layer, causing it to rupture. The outer layer may be created with a weakened bonding area, a partially scored area, or other methods of ensuring a desired rupture location and to facilitate desired timing for auto-deflation to take place. There can be any number of layers between the moist environment and the moisture expanding center. Each material layer can have different erosion rates (e.g., fast or slow) and can be selected by the predetermined time deflation is desired to occur (e.g., after 30 days, 60 days, or more). By varying the number, thickness, and rate of each of the circumferential layers, the time to deflation can be accurately controlled.

Alternatively a pressure sealing button that is adhesively bonded over a perforation in the balloon material can be provided for deflation. The adhesive bonding the button erodes over time when it comes into contact with moisture derived from the gastric fluid or that has been injected inside the balloon. Once the adhesive can no longer bond and create an airtight seal between the adhesive and the button, the balloon will rapidly deflate. By controlling the hole size and moisture exposure of the adhesive, the erosion time can be accurately predicted.

Deflation can also be facilitated by creating a series of connecting ports within the septum or on another similar structure attached to the balloon composite wall. The ports can be constructed using a water- or acid-dissolving, biologically compatible, low permeability substance, such as gelatin. The diameter of the hole, number of holes, channel width, and channel length can all be adjusted to control the dissolving parameters. Once the material in the ports and channel is dissolved, there is a clear path for gas trapped in the balloon to escape, eventually resulting in a deflated balloon. The water can be gastric fluid or controlled internally by including water inside the balloon at assembly or during the inflation process. There can be a plurality of port openings to guarantee gas transmits. Additionally, there are several variables that can be adjusted to control dissolution time: size of the port openings; number of port openings; the length of the internal channel; the width of the internal channel; and the rate of material dissolution. The port/channel layout design can ensure that only a small amount of surface area is exposed to moisture at any particular time, thereby controlling the rate of erosion and ultimately deflation.

A mechanism to facilitate passing involves an erosion mechanism that allows for the balloon to be broken down into a size that has a higher probability of predictably passing through the lower gastrointestinal system. Preferably, the size of the balloon as deflated is less than 5 cm long and 2 cm thick (similar to various foreign objects of similar size that have been shown to pass predictably and easily through the pyloric sphincter). This can be accomplished by providing the balloon with "erodible seams." One seam that breaks the balloon open into (at a minimum) two halves, or more seams are provided so that a plurality of smaller balloon pieces is produced in the dissociation reaction. The number of seams used can be selected based on the original surface area of the balloon and what is required to dissociate the balloon into pieces that are of a size that can predictably pass through the gastrointestinal tract more easily. The rate of seam erosion can be controlled by using a material affected by, e.g., the external gastric environment pH, liquid, humidity, temperature, or a combination thereof. Seams can be single layer consisting of only erodible material, or multi-layer. The timing of self-deflation can be further controlled by the design of the seam layers, e.g., making the reaction and/or degradation of the seam material dependent on the internal environment of the balloon instead of the external environment. By manipulating the reaction such that erosion or degradation is initiated by the internal environment (e.g., the balloon's internal pH, humidity, or other factors), any impact of person-to-person gastric variability (pH, etc.) that can affect erosion timing is minimized. The internal balloon environment can be manipulated by adding excess water at injection to create a more humid internal environment, or the amount of constituents added can be varied to manipulate the pH, etc.

Ultrasound Tracking and Visualization Subcomponent

The present disclosure implements tracking and visualization functionality into devices and systems described above. As used herein, "visualization" is used broadly to refer to locating, characterizing, or otherwise identifying an item of interest in the body in a number of ways, including by ultrasonic and other acoustic wave data such as wave strength, wave orientation, temporal characteristics of the wave, the effects of the wave on a sensor, and other attributes of an ultrasound or acoustic wave that may be used to facilitate tracking, locating, identifying, and characterizing an item of interest, as well as audio, visual, tactile, or other output based on the ultrasound data that characterizes the item of interest. Due to the non-invasive nature of the present device, physicians may desire to determine, or confirm, the location and orientation of the device prior to inflation or during the course of treatment. The present disclosure relates to ultrasound-related devices and methods for determining and confirming the location, orientation and/or state of an intragastric device at all phases of administration. Such ultrasound-related means include but are not limited to ultrasonography or ultrasonic imaging, "very directional" Doppler systems, Doppler imaging systems, and systems related to intravascular ultrasound techniques.

Ultrasound is an oscillating sound pressure wave with a frequency greater than the upper limit of the human hearing range. Ultrasound is thus not separated from 'normal' (audible) sound by differences in physical properties, only by the fact that humans cannot hear it. Although this limit varies from person to person, it is approximately 20 kilohertz (20,000 hertz) in healthy, young adults. Ultrasound devices operate with frequencies from 20 kHz up to several gigahertz.

Diagnostic sonography (ultrasonography) is an ultrasound-based diagnostic imaging technique used for visualizing internal body structures including tendons, muscles, joints, vessels and internal organs for possible pathology or lesions. The practice of examining pregnant women using ultrasound is called obstetric sonography, and is widely used. In physics, 'ultrasound' refers to sound waves with a frequency too high for humans to hear. Ultrasound images (sonograms) are made by sending a pulse of ultrasound into tissue using an ultrasound transducer (probe). The sound reflects and echoes off parts of the tissue; this echo is recorded and displayed as an image to the operator. The techniques employed for imaging tissue and organs using ultrasound can be adapted for imaging the intragastric device or devices of the embodiments Many different types of images can be formed using ultrasound. The most well-known type is a B-mode image, which displays a two-dimensional cross-section of the tissue being imaged. Other types of image can display a three-dimensional region, enabling precise location of the intragastric device within the gastric system. In certain embodiments, application of ultrasound can also be used to rupture the device, facilitating passage of the deflated device out of the body at the end of its useful life.

Compared to other prominent methods of medical imaging, ultrasonography has several advantages. It provides images in real-time (rather than after an acquisition or processing delay), it is portable and can be brought to a sick patient's bedside, it is substantially lower in cost, and it does not use harmful ionizing radiation. Each of these features is particularly advantageous for locating or tracking an intragastric device.

Typical diagnostic sonographic scanners operate in the frequency range of 2 to 18 megahertz, though frequencies up to 50-100 megahertz have been used in biomicroscopy. The choice of frequency is a trade-off between spatial resolution of the image and imaging depth: lower frequencies produce less resolution but image deeper into the body. Higher frequency sound waves have a smaller wavelength and thus are capable of reflecting or scattering from smaller structures. Higher frequency sound waves also have a larger attenuation coefficient and thus are more readily absorbed in tissue, limiting the depth of penetration of the sound wave into the body. Different frequencies can be employed, depending upon the condition of the intragastric device at the time of imaging. For example, an uninflated intragastric device in compacted form may benefit from use of a higher imaging wavelength (e.g., 7-18 MHz) due to the smaller cross section, especially when imaging in the region of the throat, wherein the device would be expected to be close to the surface of the body, while a lower imaging wavelength (e.g., 1-6 MHz) may be desirable for the intragastric device in a larger inflated form in the stomach, where the distance to the surface of the skin may be further, wherein a lower axial and lateral resolution but greater penetration is observed.

Ultrasonography can use a hand-held probe (called a transducer) that is placed directly on and moved over the patient. Sonography is effective for imaging soft tissues of the body. Superficial structures such as muscles, tendons, testes, breast, thyroid and parathyroid glands, and the neonatal brain are imaged at a higher frequency (7-18 MHz), which provides better axial and lateral resolution. Deeper structures such as liver and kidney are imaged at a lower frequency 1-6 MHz with lower axial and lateral resolution but greater penetration.

In ultrasound, a sound wave is typically produced by a piezoelectric transducer or a capacitive micromachined transducer, encased in a housing which can take a number of forms. Strong, short electrical pulses from the ultrasound machine make the transducer ring at the desired frequency. The frequencies can be anywhere between 2 MHz or lower and 18 MHz or higher. The sound is focused either by the shape of the transducer, a lens in front of the transducer, or a complex set of control pulses from the ultrasound scanner machine (beamforming). This focusing produces an arc-shaped sound wave from the face of the transducer. The wave travels into the body and comes into focus at a desired depth.

Transducers focus their beam with physical lenses or use phased array techniques to enable the sonographic machine to change the direction and depth of focus. Almost all piezoelectric transducers are made of ceramic. Materials on the face of the transducer enable the sound to be transmitted efficiently into the body (e.g., a rubbery coating, a form of impedance matching). In addition, a water-based gel is typically placed between the patient's skin and the probe. The techniques of the embodiments can be applied to administration of the gastric device to a patient with an empty stomach, or to a patient with a stomach partially filled with liquid and/or solid gastric contents.

The sound wave is partially reflected from the layers between different tissues, or from the interface between the device in compacted form and the surrounding tissue, or the interface between the device in inflated form and the surrounding tissue or gastric fluids or content. Specifically, sound is reflected anywhere there are density changes, such that some of the reflections return to the transducer. The return of the sound wave to the transducer results in the same process that it took to send the sound wave, except in reverse. The return sound wave vibrates the transducer, the transducer turns the vibrations into electrical pulses that travel to the ultrasonic scanner where they are processed and transformed into a digital image. The sonographic scanner determines from each received echo how long it took the echo to be received from when the sound was transmitted, and how strong the echo was. The focal length for the phased array can also be determined, enabling a sharp image of that echo at that depth. The ultrasonic imaging energy is delivered as a pulse with a specific carrier frequency. Moving objects change this frequency on reflection, so that it is only a matter of electronics to have simultaneous Doppler sonography enabling movement to be imaged. The received image is then digitally displayed.

Ultrasonography (sonography) uses a probe containing multiple acoustic transducers to send pulses of sound into a material. Whenever a sound wave encounters a material with a different density (acoustical impedance), as in a compact or inflated intragastric device, part of the sound wave is reflected back to the probe and is detected as an echo. The time it takes for the echo to travel back to the probe is measured and used to calculate the depth of the tissue interface causing the echo. The greater the difference between acoustic impedances, the larger the echo is. If the pulse hits gases or solids, the density difference is so great that most of the acoustic energy is reflected and it becomes impossible to see deeper. This feature is advantageous in the imaging of an inflated intragastric device.

The frequencies used for imaging are generally in the range of 1 to 18 MHz. Higher frequencies have a correspondingly smaller wavelength, and can be used to make sonograms with smaller details. However, the attenuation of the sound wave is increased at higher frequencies, so in order to have better penetration of deeper tissues, a lower frequency (3-5 MHz) is used.

Seeing deep into the body with sonography is very difficult. Some acoustic energy is lost every time an echo is formed, but most of it (approximately) is lost from acoustic absorption. The speed of sound varies as it travels through different materials, and is dependent on the acoustical impedance of the material. However, the sonographic instrument assumes that the acoustic velocity is constant at 1540 m/s. An effect of this assumption is that in a real body with non-uniform tissues, the beam becomes somewhat de-focused and image resolution is reduced. However, in the various embodiments, the profile of the device in its different forms (compacted, undergoing inflation, inflated, undergoing deflation, deflated) is generally readily ascertained despite the lower image resolution.

To generate a two-dimensional (2D) image, the ultrasonic beam is swept. A transducer may be swept mechanically by rotating or swinging. Or a one dimensional phased array transducer may be used to sweep the beam electronically. The received data is processed and used to construct the image. The image is then a 2D representation of the slice into the body. A 2D image may be acceptable for determining the passage of the device longitudinally through the gastrointestinal tract. Once in place, it may be desirable to image the device in the stomach in three dimensions. 3D images can be generated by acquiring a series of adjacent 2D images. A 2D phased array transducer that can sweep the beam in 3D can be employed, as is commonly used in cardiac imaging. Doppler ultrasonography is used to image motion. The different detected speeds are represented in color for ease of interpretation. Colors may alternatively be used to represent the amplitudes of the received echoes. Such ultrasonography can be advantageously employed to image the device as it moves down the esophagus.

Several modes of ultrasound used in medical imaging can be employed in various embodiments. A-mode (amplitude mode) is the simplest type of ultrasound. A single transducer scans a line through the body with the echoes plotted on screen as a function of depth. A-mode ultrasound also allows for pinpoint accurate focus of a destructive wave energy, e.g., for use in deflating an inflated intragastric device. In B-mode (brightness mode) ultrasound, a linear array of transducers simultaneously scans a plane through the body that can be viewed as a two-dimensional image on screen. This mode is more commonly known as 2D mode now. A C-mode image is formed in a plane normal to a B-mode image. A gate that selects data from a specific depth from an A-mode line is used; then the transducer is moved in the 2D plane to sample the entire region at this fixed depth. When the transducer traverses the area in a spiral, an area of 100 cm2 can be scanned in around 10 seconds. In M-mode (motion mode) ultrasound, pulses are emitted in quick succession—each time, either an A-mode or B-mode image is taken. Over time, this is analogous to recording a video in ultrasound. As the boundaries of the intragastric device produce reflections move relative to the probe, this can be used to determine the velocity of the intragastric device. Doppler mode makes use of the Doppler effect in measuring and visualizing moving objects such as the intragastric device. Velocity information can be presented as a color-coded overlay on top of a B-mode image. Doppler information can be continuously sampled along a line through the body, and all velocities detected at each time point are presented (on a time line). In pulsed wave (PW) Doppler, Doppler information is sampled from only a small sample volume (defined in 2D image), and presented on a timeline. Duplex mode is used to refer to the simultaneous presentation of 2D and (usually) PW Doppler information. Color Doppler can be referred to as Triplex mode. In the pulse inversion mode, two successive pulses with opposite sign are emitted and then subtracted from each other. This means that any linearly responding constituent will disappear while gases with non-linear compressibility stand out. Pulse inversion may also be used in a similar manner as in harmonic mode, wherein a deep penetrating fundamental frequency is emitted into the body and a harmonic overtone is detected. This way noise and artifacts due to reverberation and aberration are greatly reduced. Penetration depth can be gained with improved lateral resolution. An additional expansion or additional technique of ultrasound is biplanar ultrasound, in which the probe has two 2D planes that are perpendicular to each other, providing more efficient localization and detection. An omniplane probe is one that can rotate 180° to obtain multiple images. In 3D ultrasound, many 2D planes are digitally added together to create a 3-dimensional image of the object.

In contrast-enhanced ultrasound, microbubble contrast agents enhance the ultrasound waves, resulting in increased contrast. In a similar fashion, the intragastric device can advantageously be completely or partially filled with a heavy gas such as perfluorocarbon or nitrogen to enhance contrast. Heavy gases suitable for use include but are not limited to nitrogen, argon, $SF_6$, and halocarbons such as $C_2F_6$, $C_3F_8$, $C_4F_{10}$, $C_4F_8$, $C_3F_6$, $CF_4$, and $CClF_2$—$CF_3$.

Sonography can be enhanced with Doppler measurements, which employ the Doppler Effect to assess whether structures such as the intragastric device are moving towards or away from the probe, and the structure's relative velocity. By calculating the frequency shift of a particular sample volume, for example flow in an artery or a jet of blood flow over a heart valve, its speed and direction can be determined and visualized. This is particularly useful in cardiovascular studies (sonography of the vascular system and heart) and essential in many areas such as determining reverse blood flow in the liver vasculature in portal hypertension. The Doppler information is displayed graphically using spectral Doppler, or as an image using color Doppler (directional Doppler) or power Doppler (non-directional Doppler). This Doppler shift falls in the audible range and is often presented audibly using stereo speakers: this produces a very distinctive, although synthetic, pulsating sound. Most modern sonographic machines use pulsed Doppler to measure velocity. Pulsed wave machines transmit and receive series of pulses. The frequency shift of each pulse is ignored; however the relative phase changes of the pulses are used to obtain the frequency shift (since frequency is the rate of change of phase). The major advantages of pulsed Doppler over continuous wave is that distance information is obtained (the time between the transmitted and received pulses can be converted into a distance with knowledge of the speed of sound) and gain correction is applied. The disadvantage of pulsed Doppler is that the measurements can suffer from aliasing. The terminology "Doppler ultrasound" or "Doppler sonography" has been accepted to apply to both pulsed and continuous Doppler systems despite the different mechanisms by which the velocity is measured. There are no standards for the display of color Doppler. A common convention is to use red to indicate flow toward the transducer and blue away from the transducer, or to display a red shift representing longer waves of echoes (scattered) from the target.

Ultrasonography offers a number of advantages for imaging the intragastric device in vivo. Ultrasonography images solid surfaces very well and is particularly useful for delineating the interfaces between solid and fluid-filled spaces, enabling the imaging of the device in both a solid, compacted form as well as an inflated form or even a deflated form. The method enables live images to be obtained, showing motion as well as position of the intragastric device. The method has no known long-term side effects and rarely causes any discomfort to the patient. The equipment is widely available and comparatively flexible. Small, easily carried scanners are available such that examinations can be performed in a physician's office or in a clinic setting. The technology is also relatively inexpensive compared to other methods, such as CAT imaging or magnetic resonance imaging. Spatial resolution is better in high frequency ultrasound transducers than it is in most other imaging modalities, enabling accurate tracking of the intragastric device.

It is known that there might be difficulties imaging tissue structures deep in the body, especially in obese patients, using ultrasound. Body habitus has a large influence on image quality. Image quality and accuracy of diagnosis is limited with obese patients, overlying subcutaneous fat attenuates the sound beam and a lower frequency transducer is required (with lower resolution). However, the device in solid, compacted form provides satisfactory imaging contrast. The device in inflated form, especially when containing nitrogen, $SF_6$, or other halocarbons, exhibits excellent contrast, unlike tissue structures in vivo, enabling ease of imaging even in the morbidly obese.

In some embodiments, an ultrasound sensor comprises a non-contact sensor. An ultrasonic level or sensor or sensing system requires no contact with the target. In the medical industries this is an advantage over inline sensors that may contaminate or otherwise interfere with the marker or item of interest. In some embodiments, the sensor is a microphone.

In some embodiments, a pulsed wave system is used. The principle behind a pulsed-ultrasonic technology is that the transmit signal consists of short bursts of ultrasonic energy. After each burst, the sensor electronics looks for a return signal within a small window of time corresponding to the time it takes for the energy to pass through the medium of interest. Only a signal received during this window will qualify for additional signal processing. In some embodiments a continuous wave system is used. In the pulsed, continuous, or other wave systems, the sensor may be a microphone that receives the return wave signal.

In some embodiments, a marker may transmit ultrasound signals. For instance, Ultrasound Identification (USID) may be used to automatically track and identify the location of intragastric devices in real time using simple, inexpensive nodes (badges/tags) attached to or embedded in the ultrasound devices, which then transmit an ultrasound signal to communicate their location to ultrasound sensors, such as microphones.

A computing system may be implemented in the ultrasound locating system. The computing system comprises hardware and software that receives data from the ultrasound sensor and calculates information related to the location, orientation, and/or state of an intragastric device according to certain algorithms. In some embodiments, the hardware may comprise a central processing unit, memory, an analog to digital converter, analog circuitry, a display. In some embodiments, the software proceeds through a number of steps including calibration, initialization, prediction, estimation, measuring magnetic sensor data, calculating various desired outputs including location, orientation, size, configuration, etc. in accordance with the techniques discussed herein.

The processor's output relating to the location, orientation and/or state of an intragastric device may be communicated to a user in a number of manners. In some embodiments, the output is shown visually on a display.

In some embodiments, the processor's output related to an intragastric device's location, orientation, and/or state is audibly communicated to a user through a speaker.

In some embodiments, the processor's output related to an intragastric device's location, orientation, and/or state is communicated to a user through a combination of methods. For instance, the system may employ a visual graphical display with audible alerts sent through speakers.

In some embodiments, the ultrasound locating system is calibrated before use. The ultrasound marker and the sensor are positioned in pre-planned locations and orientations to verify the output signal is within an expected range. In some embodiments, the ultrasound locating systems are calibrated or otherwise verified using a human patient simulator, or dummy, to test the ultrasound locating system as an ultrasound marker travels through the simulator. In some embodiments, the ultrasound locating system is checked for stray signals from nearby acoustic interferences.

The ultrasound sensor may be used in conjunction with the marker or markers in a variety of embodiments to locate or otherwise characterize an ingested intragastric device. In some embodiments, an off-the-shelf intragastric device, such as a swallowable, inflatable balloon, may be used without modification with any ultrasound markers. With that device, an ultrasound sensor that pulses sound waves and senses their return signal with a microphone may be used outside the body. The device could be swallowed in a deflated state and would then inflate or be inflated once inside the stomach. The ultrasound sensor may be used to locate or otherwise characterize the device by pulsing the device and receiving the return signals, in accordance with the techniques discussed above.

The devices once ingested may be located using the ultrasound intragastric locating system. In some embodiments, the sensor may locate the device by pulsing in various locations and analyzing the return signal. For instance, a return signal corresponding to a body organ without the device may be pre-determined by correlating a return wave signal to a location on the body before the device is swallowed. This could produce an ultrasound map of the organ or body without any device. Then, after swallowing the device, and by running the sensor over the body, if a different signal is returned for a corresponding location in the body, then the location of the device is thus identified. This may be implemented in accordance with the techniques discussed above.

The orientation of the devices once ingested may be ascertained using the ultrasound intragastric locating system. In some embodiments, the sensor may identify the orientation of the intragastric device by pulsing and sensing at various locations of the device and analyzing the return signals. For instance, before ingestion by a patient, the device may be pulsed at various orientations such that a pre-determined database exists of known correlations between return wave signatures and orientation of the device. This may be done for the device in the deflated, inflated, or other states. Then, after ingestion, the device may be pulsed and the return signals compared to the pre-determined database to determine the orientation of the device in accordance with the techniques discussed above.

Further, the various sizes and configurations of the devices once ingested may be characterized using the ultrasound intragastric locating system in accordance with the techniques discussed above. For instance, inflation of a balloon, or the inflation or configuration of multiple balloons, may be characterized and assessed. In some embodiments, the sensor may characterize the device or devices by pulsing and sensing at various locations of the device and analyzing the return signals. For instance, the deflated device would return a different pulsed signature than the inflated device. In such a manner, the device may be characterized as either inflated, deflated, or in some other state. The inflated device could further be characterized before ingestion by a patient such that the return signal signature is pre-determined and serves as a guidepost for assessing the state of the device. In some embodiments, the ultrasound locating system may be used in conjunction with a deflating system to characterize the deflation process.

The timing and other attributes of the various methods of administration can be characterized using the disclosed ultrasound intragastric locating system and techniques. Whether the device is administered using endoscopic techniques or orally, the progress of the device as it makes its way to the stomach can be tracked with the ultrasound locating system. For instance, the effects of swallowing the device with hard gelatin or water or other consumables may be characterized by tracking the location and orientation as it is ingested. In some embodiments, the endoscope employed to deliver the intragastric device incorporates an ultrasound emitting device at a preselected distance from the intragastric device to be deployed. The ultrasound transmittal can enable precise positioning of the intragastric balloon, as well as monitoring of the inflation process by changes in the emitted ultrasound due to proximal inflation of the intragastric device.

In some embodiments, the ultrasound locating system may characterize an intragastric device that has a circular or elliptical cross-section. Two ultrasonic modules placed in the device allow the system to measure the size and composition of the device using time of flight ultrasound technology.

Using the speed of sound, a distance can be computed from the time between transmission and reception. The time between transmission of the ultrasonic pulse and reception of the echo is given by: $t=2d/U$, or $d=Ut/2$, (53) where U is the speed of sound in the medium of interest, and d is the diameter of the device. If transmission occurs in two orthogonal directions, two dimensions of the intragastric device can be determined, and thus the area of the device can be computed. Assuming the device is an ellipse, the equation for the area of an ellipse using the major (a) and minor (b) axes is as follows:

$$A = \pi \cdot a \cdot b = (\pi \cdot U^2 \cdot t_1 \cdot t_2)/16$$

If the interior of an inflated device is clear, a clear echo signal is obtained and the time of flight of the ultrasound pulse is obtained in the clear area to determine device area. To detect the presence of matter, foreign or otherwise, in the device, two methods may be used. First, the orthogonal signal, that is the amplitude of the scattered ultrasonic pulse in the orthogonal direction, is compared with the original pulse echo return. And second, the amount of false return in the original pulse echo may even determine the ratio of solid to liquid matter in the analyzed cross section of the device.

The intragastric device may include two orthogonal ultrasonic transmitter/receiver ("transceiver") modules. One transceiver is an anterior/posterior (a/p) ultrasonic module, and the other transceiver is a lateral ultrasonic module. The device further includes a microprocessor that measures the time of flight from each transceiver module. The microprocessor is capable of distinguishing between device echoes and the empty device interior. The microprocessor is also capable of preparing a signal for transmission. The microprocessor is in electrical communication with a computer. In some embodiments, the computer and the microprocessor are incorporated into the same component. In at least one embodiment, the computer may be a look up table, capable of determining the semi-major axis, the semi-minor axis, and the scatter associated with the device.

The intragastric device may also include a transmitter capable of transmitting the signals from the device to a location outside of the body. The transmitter can include an antenna for transmission, or an antenna in the band (not shown) can be in electrical communication with the transmitter. The device may also include a module either containing a battery or capable of powering the intragastric device electronics inductively. External to the patient may be an antenna for receiving the transmitted signals and a receiver in operative communication with the antenna. A computer may be included that has software capable of decoding and processing the signals transmitted by the transmitter and received by the receiver. The computer software is capable of measuring the time of flight of horizontal and vertical ultrasonic pulses to determine the length and width of the intragastric device, and combining the length and width to find the area. It should be noted that from the scatter of the horizontal into the vertical receiver and the scatter of the vertical into the horizontal receiver, the presence of any material in the device can be determined.

The various ultrasound markers and their acoustic properties may be implemented in the ultrasound intragastric device locating system with ultrasound sensors or detectors. The ultrasound markers comprise any substance, material, or object, to which the ultrasound sensors or detectors are responsive. As mentioned, an ultrasound "marker" as used herein therefore includes the intragastric device itself, such that an off-the-shelf, unmodified intragastric device may already contain materials that are responsive to or otherwise may be used with the ultrasound locating system disclosed herein.

In some embodiments, the marker is a node attached to and/or embedded in and/or otherwise coupled to the intragastric device. Such a node may be, for example, a badge or tag that is responsive to applied ultrasound energy. The node may also emit or transmit an ultrasound signal to communicate its location to microphone sensors. The node may be incorporated with the intragastric device in various arrangements.

EXAMPLES

Ultrasound Location

Figure 2:
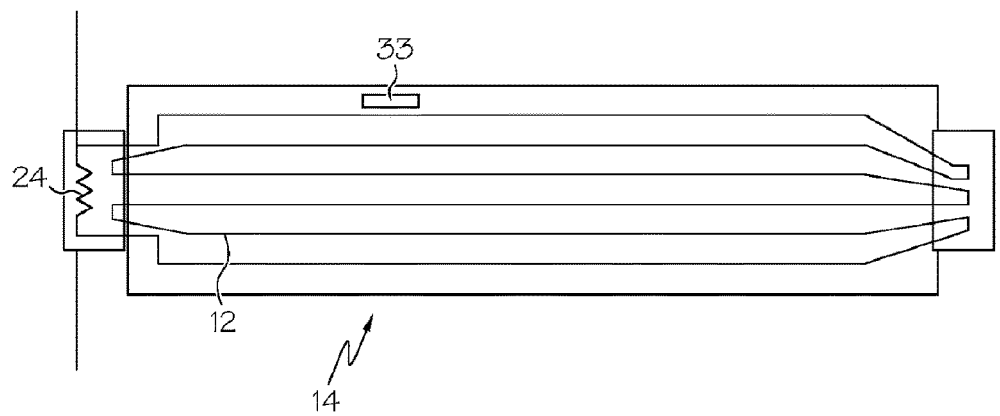
FIG. 2 depicts a system for locating or otherwise characterizing an intragastric device using ultrasound.

Referring now to FIGS. 1 and 2, a system for locating or otherwise characterizing an intragastric device using ultrasound is illustrated in accordance with at least one embodiment of the present invention. The system 10 of FIG. 1 is used for measuring a characteristic of the device, such as size, using an external tuned circuit and a passive coil embedded in or on the device. The system 10 includes a first coiled conductor 12 (or internal coil) positioned within an intragastric device 14 (shown in more detail in FIG. 2). The phrases "internal coil" and "inner coil" are also used herein to denote the first coiled conductor 12. The system further includes a circuit external to the device and patient that includes a tunable frequency generator 16, a spectrum analyzer 18, and a second coiled conductor 20. The phrases "external coil" and "outer coil" are also used herein to denote the second coiled conductor 20. The frequency generator may be a variable frequency oscillator, for example. The phrase "frequency generator" is used to denote any type of electrical or electronic device that produces repetitive electrical or electronic signals. For example, the frequency generator may be an electronic device capable of generating repeating sine waves. The phrase "spectrum analyzer" is used to denote any electrical or electronic device capable of measuring the frequency and amplitude of a signal.

The system further includes appropriate capacitance, inductance, and resistance to allow resonance both when a patient is absent and when the patient is present, as will be described in detail below. For example, the system shown in FIG. 1 includes a variable capacitor 22 that can be tuned to achieve resonance. Rather than providing a variable capacitor, in some embodiments, the capacitor can be of fixed value and a variable inductor can be included.

The system 10 may also include a device 24 for controlling heating within the interior coil 12, shown in FIG. 2. As seen in FIG. 2, the device 24, for example a resistor, is in electrical communication with the internal coil. In some embodiments, two electrical leads attached to the two-terminal resistor can be extended out from the intragastric device, thereby allowing a measurement to be taken. That is, the first terminal of the resistor can be in electrical communication with a first end of a first electrical lead, and the second terminal of the resistor can be in electrical communication with a first end of a second electrical lead. The second ends of the first and second electrical leads can extend outward, external to the intragastric device 14.

Figure 3:
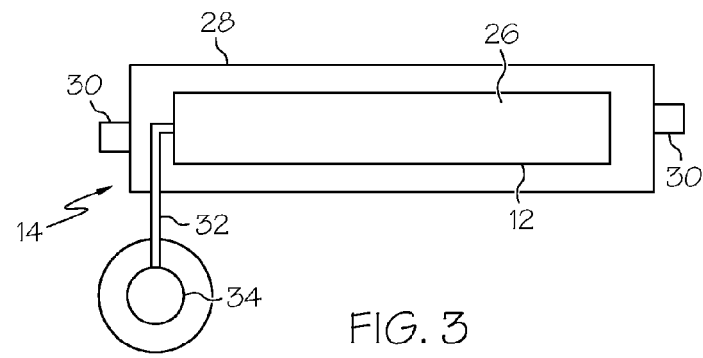
FIG. 3 depicts the intragastric device 14 with internal coil 12, having an inflatable section 26, a solid substrate 28, and placement tabs 30.

In at least one embodiment, the electrical leads are accessible via an access port on the patient's body, as seen in FIG. 3. FIG. 3 depicts the intragastric device 14 with internal coil 12, having an inflatable section 26, a solid substrate 28, and placement tabs 30. As seen, electrical leads 32 extend from the injection port 34 to the internal coil 12 to allow measurement of the current in the coil. In some embodiments, these leads can be conductively connected to the external circuit such that the external circuit includes the intragastric device 14 and its internal coil in the tuned circuit.

It should be noted that in the above-described embodiments, no battery or radiofrequency (RF) module is needed because the current in the intragastric device 14 is a result of induction.

The system may further include a computer 35, depicted in FIG. 1, having software capable of performing calculations based on the current in the first coiled conductor and the resonant frequency in the external circuit in order to determine the size of the intragastric device 14. The derivations, calculations, and theory of operation of the system are presented below.

Figure 4A:
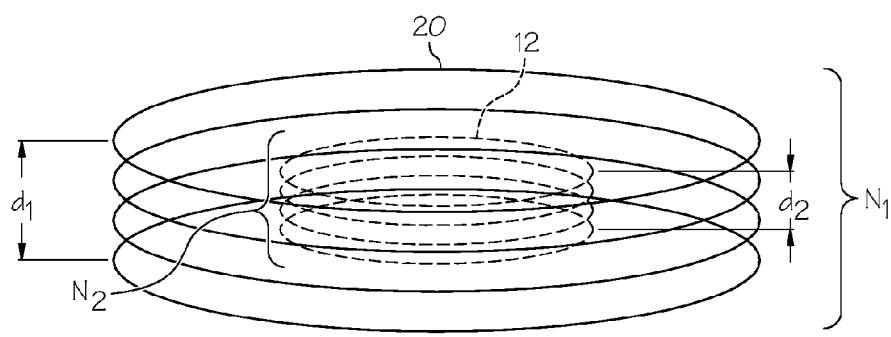
FIG. 4A depicts an intragastric device wherein the inner coil and the outer coil are placed concentrically and coaxially relative one another.

Two embodiments of the present invention utilize induction to calculate the size, orientation or other characteristic of the intragastric device 14. The first embodiment using induction to be considered is when the inner coil and the outer coil are placed concentrically and coaxially relative one another, as shown schematically in FIG. 4A. Such an embodiment occurs when the external coil is placed around the patient's body such that the inner coil in or on the intragastric device 14 is concentric with the external coil. The number of turns N of each solenoid is equal to the number of turns per unit length (n) * the length (d) of the solenoid. So, the number of turns of the outer solenoid in FIG. 4 is given by the equation $N_1 = n_1 * d_1$. It is assumed that the external coil is excited with the following current:

$$I = I_0 \sin \omega t, \tag{1}$$

where $\omega$=the angular frequency of the current source and $I_0$ is the maximum current of the current source. Then, the magnetic field B for a relatively long coil is given by the relation:

$$B = \mu \cdot N_1 I_0 \cdot \sin(\omega \cdot t)/d_1, \tag{2}$$

where $N_1$ is the number of turns in the coil, and $d_1$ is the length of the coil. The magnetic flux from the larger external coil subtended by the intragastric device 14 is:

$$\Phi = A_2 \cdot B = A_2 \cdot \mu \cdot N_1 \cdot I_0 \cdot \sin(\omega \cdot t)/d_1, \tag{3}$$

where $\mu$ is the magnetic susceptibility of the material contained within the area $A_2$ of the inner coil, B is the magnetic field density, and $N_1$ is the number of turns in the coil. The electromotive force (emf) generated by coil 1 in coil 2 is given by the relation:

$$E = -d\Phi/dt = -A_2 \cdot B = A_2 \mu \cdot N_1 \cdot \omega_1 \cdot I_0 \cdot (\cos \omega t)/d_1 \tag{4}$$

The voltage induced in the entire intragastric device 14 is given by the relation:

$$E_T = N_2 \cdot E = -A_2 \cdot \mu \cdot N_1 \cdot N_2 \cdot \omega_1 \cdot I_0 \cdot \cos(\omega \cdot t)/d_1 \tag{5}$$

The self inductance (L) of a coil is defined as:

$$L = N \cdot \Phi / i = N \cdot A \cdot \mu \cdot N / l = N^2 \cdot A \cdot \mu / d_1 \tag{6}$$

The self induced emf in the coil is then $$V = -L dI/dt = -\omega \cdot N^2 \cdot A \cdot \mu \cdot I_0 \cdot \cos(\omega \cdot t)/d_1 \tag{7}$$

The mutual inductance (M) of the two coils is defined as $$M_{21} = N_2 \cdot \Phi_{21} i_1, \tag{8}$$

where the current in coil 1 generates a flux in coil 2.

$$N_2 \cdot \Phi_{21} = N_2 \cdot B_1 \cdot \pi \cdot R_2^2, \tag{9}$$

and also $$N_2 \cdot \Phi_{21} = N_2 \cdot N_1 \cdot \pi \mu_0 \cdot R_2^2 \cdot i_1/2 \cdot R_1, \tag{10}$$

Thus the mutual inductance for the device and the external coil can be given by $$M_{21} = N_2 \cdot N_1 \cdot \pi \cdot \mu_0 \cdot R_{21}^2 / 2 \cdot R_1 \tag{11}$$

It should be noted that although the magnetic field generated by the larger coil is essentially constant through the smaller coil, this is not true of the field induced by the smaller coil in the larger. But the mutual inductance of the larger coil upon the smaller is equal to that of the smaller coil upon the larger.

Continuing with the derivation, the voltage of a circuit is the sum of the voltages resulting from the resistance (VR), capacitance (VC), and inductance (VL) such that $$V = V_R + V_C + V_L, \tag{12}$$

or as a function of time in integro-differential form, $$v(t) = I_1 \cdot R + L_1 \cdot dI_1/dt + 1/C \cdot \int I_1 dt, \tag{13}$$

or expressed completely as a differential equation (14):

$$\frac{1}{L_1} \cdot \frac{dv(t)}{dt} = \frac{d^2 I_1}{dt^2} + \frac{R}{L_1} \cdot \frac{dI_1}{dt} + \frac{1}{L_1 \cdot C} \cdot I_1. \tag{14}$$

If the variable frequency oscillator applies an excitation of $$v(t) = V_0 \sin(\omega t) \tag{15}$$

to the external coil and associated resistor and capacitor, then equation (14) can be written as $$\frac{V_0 \omega}{L_1} \cdot \frac{dv(t)}{dt} = \frac{d^2 I_1}{dt^2} + \left(\frac{1}{\tau_0}\right) \frac{dI_1}{dt} \cdot R + \omega_0^2 \cdot I_1, \tag{16}$$

where $$\tau_0 = \frac{L_1}{R} \tag{17}$$

The tuned (or resonant) circuit including the external loop has a natural frequency given by:

$$\omega_n = \sqrt{1/(L \cdot C)} \tag{18}$$

The quality factor, or Q, of a resonant circuit is given by:

$$Q = \omega_n \cdot L/R = \sqrt{1/(L \cdot C)} \cdot L/R = 1/R \cdot \sqrt{L/C} \tag{19}$$

The bandwidth ($\omega 2 - \omega 1$) of the frequency plot (i.e. the width at half maximum response as measured by the spectrum analyzer) is given by:

$$\omega_2 - \omega_1 = \omega_n / Q = R/L_1 = 1/\tau_0 \tag{20}$$

If the induced emf in the LAGB coil is known, then $$V = N_2 \cdot -A_2 \cdot B = A_2 \cdot \mu \cdot N_1 \cdot I_0 \cdot \omega/d_1 (\cos \omega t) \tag{21}$$

Considering the external tuned circuit without the LAGB included, then:

$$dV/dt = L \cdot d^2 I/dt^2 + R \cdot dI/dt + 1/C \cdot I, \tag{22}$$

which is the general equation for a series RLC circuit. So, $$1/L \cdot dV/dt = d^2 I/dt^2 + (1 \cdot \tau) \cdot dI/dt + \omega_0^2 \cdot I, \tag{23}$$

where $$\tau = L/R, \tag{24}$$

and $$\omega_n = \sqrt{1/(L \cdot C)} \tag{25}$$

The proportional half power frequencies are given by the relationship $$\Delta \omega_0 / \omega_n = \frac{1}{2} Q = 1/\tau \cdot \omega = R/L \cdot \sqrt{1/LC} = R \cdot \sqrt{C/L} \tag{26}$$

Now, an inductive circuit (which is a single conductive loop with no other resistance) is included in the external circuit that includes the intragastric device 14 or marker. If the external coil is circuit 1 and the intragastric device 14 or marker is circuit 2, then:

$$V_1 = L_1 \cdot d^2 I_1/dt^2 + M \cdot d^2 I_2/dt^2 + I_1 \cdot R_1 + 1/C \cdot \int I_1 \cdot dt \tag{27}$$

and because there is applied voltage in the device, and because the resistance is small in the device, $$V_2 = 0 = L_2 \cdot d^2I_2/dt^2 + M \cdot d^2I_1/dt^2 \tag{28}$$

Because we observe only the current parameters in the external coil circuit, the current in the LAGB can be eliminated, leaving:

$$d^2I_2/dt^2 = -M/L_2 \cdot d^2I_1/dt^2, \tag{29}$$

then substituting into equation (27) gives $$V_1 = L_1 \cdot d^2/dt^2 + M \cdot -M/L_2 \cdot d^2I_1/dt^2 + I_1 \cdot R_1 + 1/C \cdot \int I_1 \cdot dt. \tag{30}$$

Taking the derivative of equation (30):

$$\frac{dV}{dt} = \left(\frac{(L_1 \cdot L_2 - M^2)}{L_2}\right) \cdot \frac{d^2I}{dt^2} + R \cdot \frac{dI}{dt} + 1/C \cdot I, \tag{31}$$

which equals $$\frac{L_2}{(L_1 \cdot L_2 - M^2)} \cdot \frac{dV}{dt} = \tag{32}$$

$$\frac{d^2I_1}{dt^2} + \frac{R \cdot L_2}{(L_1 \cdot L_2 - M^2)} \cdot \frac{dI_1}{dt} \cdot \frac{L_2}{C \cdot (L_1 \cdot L_2 - M^2)} \cdot I_1,$$

which equals $$L_2/(L_1 \cdot L_2 - M^2) \cdot dV/dt = d^2I/dt^2 + (1/\tau) \cdot dI/dt + \omega_0^2 \cdot I. \tag{33}$$

The resonance frequency of the external coil changes in the presence of the LAGB, as does the bandwidth of the frequency, as shown below:

$$\omega_0^2 = L_2/C \cdot (L_1 \cdot L_2 - M^2), \tag{34}$$

and where $$\tau = (L_1 \cdot L_2 - M^2)/R \cdot L_2 \tag{35}$$

Comparing the square of resonance frequency of the external coil in isolation and when concentric to the LAGB, the following ratio is obtained:

$$\frac{\omega_{no\_lap\_band}^2}{\omega_{lap\_band}^2} = \frac{\frac{1}{L_1} \cdot C}{\frac{L_2}{C \cdot (L_1 \cdot L_2 - M^2)}} \tag{36}$$

$$= \frac{(L_1 \cdot L_2 - M^2)}{(L_1 \cdot L_2)}$$

$$= 1 - \frac{M^2}{(L_1 \cdot L_2)}$$

where $\omega_{no\_lap\_band}$ is the natural frequency with no lap band or intragastric device 14 coil in the circuit and $\omega_{lap\_band}$ is the natural frequency with the lap band or intragastric device 14 coil in the circuit. Equation (36) assumes that the orientation of the external coil in relation to the LAGB is such that the resonance frequency is less in the presence of the LAGB. The ratio of the bandwidth is given by $$Q = \omega_n \cdot L/R = \sqrt{1(L \cdot C)} \cdot L/R = 1R \cdot \sqrt{L/C} \tag{37}$$

The values of $L_1$, $L_2$, and M depend on the geometry of the coils. As stated above, the first embodiment is directed toward a configuration in which the inner coil and the outer coil are placed concentrically and coaxially, as in FIG. 4A. In such an embodiment, $$M = \pi \mu N_1 N_2 R_2^2 / 2R_1 = \mu N_1 N_2 A_2 / 2R_1, \tag{38}$$

$$L_1 = N_1^2 \cdot A_1 \cdot \mu/d_1, \tag{39}$$

and $$L_2 = N_2^2 \cdot A_2 \cdot \mu/d_2, \tag{40}$$

where $R_1$ and $R_2$ are the radii of the two coils, $d_1$ and $d_2$ are the lengths of the two coils, and $A_1$ and $A_2$ are the respective areas enclosed by the coils.

Based on equations (38)-(40) for M, L1, L2, $$M^2/L_1 L_2 = \pi \cdot \mu^2 \cdot N_1^2 \cdot N_2^2 \cdot A_2^2 \cdot d_1 \cdot d_2 / 4 N_1^2 \cdot N_2^2 \cdot A_1^2 \cdot A_2 \cdot \mu^2 = \pi \cdot A_2 \cdot d_1 \cdot d_2 / 4 \cdot A_1^2 \tag{41}$$

Substituting into equation (36) results in $$\frac{\omega_{no\_lap\_band}^2}{\omega_{lap\_band}^2} = \frac{\frac{1}{L \cdot C}}{\frac{L_2}{C \cdot (L_1 \cdot L_2 - M^2)}} \tag{42}$$

$$= \frac{(L_1 \cdot L_2 - M^2)}{(L_1 \cdot L_2)}$$

$$= 1 - \frac{\pi \cdot A_2 \cdot d_1 \cdot d_2}{4 \cdot A_1^2}$$

Solving for the area A2 of the inner coil results in $$A_2 = \left(1 - \frac{\omega_{no\_lap\_band}^2}{\omega_{lap\_band}^2}\right) \cdot \left(\frac{4 \cdot A_1^2}{\pi \cdot d_1 \cdot d_2}\right) \tag{43}$$

Figure 4B:
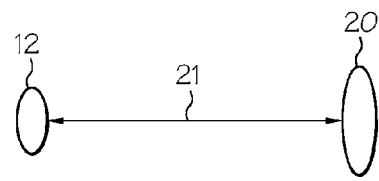
FIG. 4B depicts an intragastric device wherein the inner coil and the outer coil are placed in a coaxial non-concentric arrangement relative to one another.

The second embodiment using induction to be considered is when the inner coil 12 and the outer coil 20 are placed in a coaxial non-concentric arrangement relative to one another, as shown schematically in FIG. 4B. There is an impedance Z, shown at 21, between the coils. Such an embodiment occurs when the external coil is placed underneath or above, rather than around, the patient's body.

As stated earlier, the values of L1, L2, and M depend on the geometry of the coils. With the geometry of the second embodiment, namely of two coaxial non-concentric coils, L1, L2, and M are as follows:

$$M = \mu N_1 N_2 A_1 A_2 / 2\pi (R_1^2 + z^2)^{3/2}, \tag{44}$$

and $$L_1 = N_1^2 \cdot A_1 \cdot \mu/d_1, \tag{45}$$

and $$L_2 N_2^2 \cdot A_2 \cdot \mu/d_2 \tag{46}$$

Based on equations (44)-(46) for M, L1, L2, $$M^2/(L_1 \cdot L_2) = \mu^2 N_1^2 N_2^2 A_1^2 A_2^2 d_1 d_2 / 4_1 \pi^2 (R_1^2 + z^2)^3 N_1^2 N_2^2 A_1 A_2 \mu^2 = A_1 A_2 d_1 d_2 / 4\pi_2 (R_1^2 + z^2)^3 \tag{47}$$

Substituting into equation (36) results in $$\frac{\omega_{no\_lap\_band}^2}{\omega_{lap\_band}^2} = \frac{\frac{1}{L \cdot C}}{\frac{L_2}{C \cdot (L_1 \cdot L_2 - M^2)}} \quad (48)$$

$$= \frac{(L_1 \cdot L_2 - M^2)}{(L_1 \cdot L_2)}$$

$$= 1 - \frac{A_1 A_2 d_1 d_2}{4\pi^2 (R_1^2 + z^2)^3}$$

Solving for the area A2 of the inner coil results in $$A_2 = \left(1 - \frac{\omega_{no\_lap\_band}^2}{\omega_{lap\_band}^2}\right) \cdot \left(\frac{4\pi^2 (R_1^2 + z^2)^3}{A_1 d_1 d_2}\right) \quad (49)$$

The area of the concentric coaxial embodiment of equation (43) and the non-concentric coaxial embodiment of equation (49) can be summarized with the following equation:

$$A_2 = k \cdot \left(1 - \frac{\omega_{no\_lap\_band}^2}{\omega_{lap\_band}^2}\right), \quad (50)$$

where k depends on the geometry of the coils. Thus, the area is proportional to the absolute value of one minus the ratio of the squares of the maximum resonant frequencies, as measured by the spectrum analyzer.

$$\Delta\omega_0/\omega_n = \frac{1}{2}Q = 1/\tau \cdot \omega \quad (51)$$

Thus, the change in resonance frequency peak and the change in bandwidth can both be used to determine the product of the area and the magnetic susceptibility of the intragastric device 14 or marker. In both embodiments of the induction method, the external coil can be adjusted in both height and orientation relative to the device coil to give maximum resonance frequency variation from isolation to insure proper relative position. The use of high magnetic susceptibility fluid in the device or marker ensures that only the device or marker area is measured rather than include the stomach tissue.

As stated earlier, the system may include a computer for calculating the area of the intragastric device 14 or marker. A person of ordinary skill in the art would readily understand how to write software that calculates the area of the inner coil, as presented in equations (43) and (49) above, based on the foregoing.

Figure 5A:
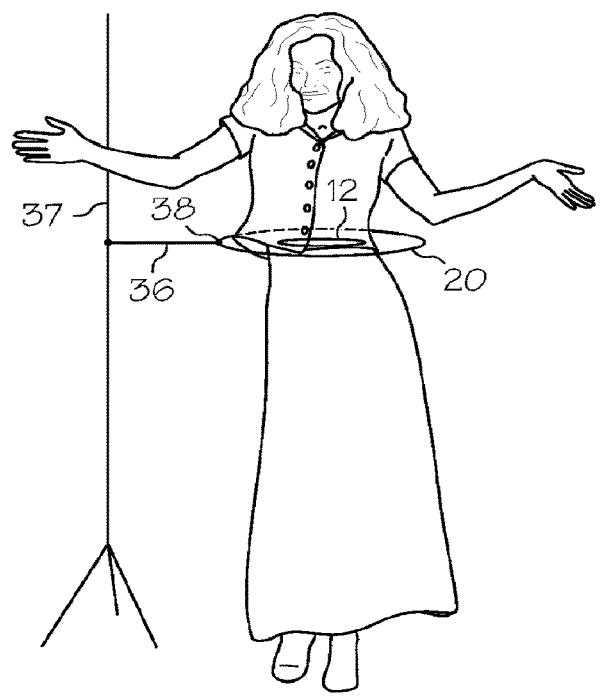
FIG. 5A depicts a coil holder for a concentric, coaxial induction.

In order to adjust the external coil to produce a maximum resonance frequency, some embodiments of the present invention include a coil holder to which the external coil is secured. Referring now to FIG. 5A, one embodiment of a coil holder for a concentric, coaxial induction embodiment is shown. The coil holder is used for orienting the external coil with the internal coil. Because the above calculations are based on the orientation between the two coils, using a coil holder can simplify the setup of the system by making stationary the external coil. As seen in FIG. 5A, the coil holder 36 can simply be an arm moveably engaged to a vertical mount 37. It is important that the coil holder 36 can be raised and lowered vertically. It is also important that the coil holder 36 can be tilted, for example about a point 38 on the coil holder. In this manner, the external coil 20 can be placed concentrically and coaxially about the internal coil 12 within the patient. There are numerous other possible embodiments of the coil holder.

Figure 5B:
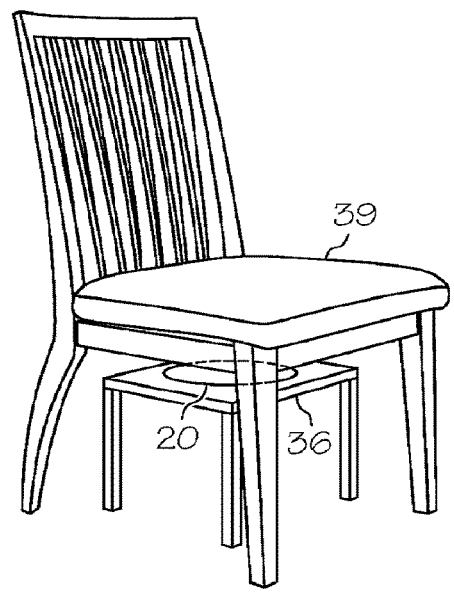
FIG. 5B depicts a coil holder for a non-concentric, coaxial induction.

Referring now to FIG. 5B, another embodiment of a coil holder is shown. Specifically, FIG. 5B depicts a coil holder for a non-concentric, coaxial induction embodiment. As seen in FIG. 5B, the coil holder 36 can simply be a small table-like device placed under the seat of a chair 39. It is important that the coil holder 36 can be tilted, as before, thereby allowing the external coil 20 to be aligned with the internal coil within the patient to align. In such an embodiment, the patient sits down on a chair 39 and the coil holder 36 underneath the chair is oriented until the resonant frequency is achieved. There are numerous other possible embodiments of the coil holder. In some embodiments, the coil may be placed above the patient, rather than underneath (not depicted).

Figure 6:
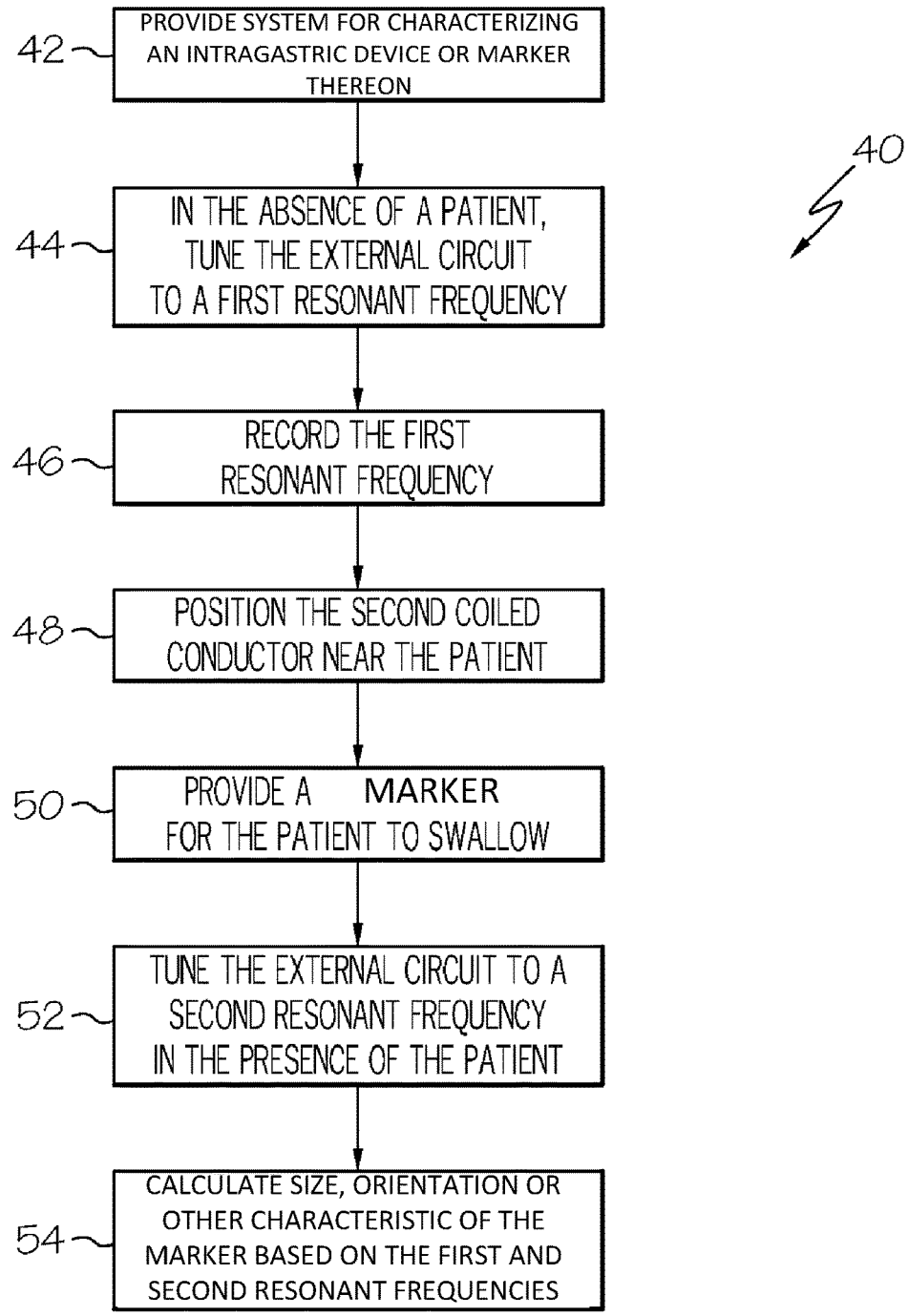
FIG. 6 depicts a flow chart for a method 40 of characterizing an intragastric device or marker thereon.

Referring now to FIG. 6, a method 40 of characterizing an intragastric device or marker thereon is shown, in accordance with at least one embodiment of the present invention. The method 40 includes the step 42 of providing a system for characterizing an intragastric device or marker thereon. Embodiments of such a system are described above. The method further includes the step 44 of tuning the circuit external to the device or marker to a first resonant frequency in the absence of a patient. This allows the practitioner to tune and measure the circuit without the effects of the coil in the marker. The first resonant frequency measured is recorded in step 46 of the method. The method further includes the step 48 of positioning the external coil near the patient. As described above, the external coil can be placed near the patient in two ways: concentrically and coaxially, and non-concentrically and coaxially. The coil is either placed around the patient at the approximate level of the device or marker, or underneath the patient. The method further includes the step 50 of providing a marker for the patient to swallow.

The measured characteristic of the device, such as the area, is based on the spike that occurs in the resonant frequency after the patient has swallowed the marker. The marker can be water with a solution of non-toxic paramagnetic material such as magnetic resonance imaging (MRI) contrast material. In some embodiments, the marker can simply be water. In many cases, the method is sensitive enough to detect the device or marker size or other characteristic without ingesting of the MRI contrast material or with a very dilute concentration. The method further includes the step 52 of tuning the circuit external to the device or marker to a second resonant frequency in the presence of the patient. In some embodiments of the method, the external coil can be moved so as to obtain the greatest change in resonance frequency of the external circuit. For example, the external coil can be moved up and down, side to side, and can be tilted so that it is aligned with the internal coil. Finally, the method includes the step 54 of calculating the size, orientation or other characteristic of the marker or device based on the difference between the first resonant frequency and the second resonant frequency. From the change of resonance frequency of the external tuned circuit, the area of the device or marker is calculated, knowing the magnetic susceptibility of the MRI contrast material.

Referring now to FIGS. 7-10, a setup and method of equipment verification using a gastric magnetic susceptibility phantom. FIG. 7A depicts a top view of the basic setup of the phantom for equipment verification. The setup 60 includes a peristaltic pump 62 with longitudinal axis 63

(shown in FIG. 7B), with a lumen 64, tissue 66, and three test laparoscopically adjustable gastric markers 68, such as gastric bands. It should be noted that more markers 68 could be used, depending on the accuracy desired.

Figure 7A:
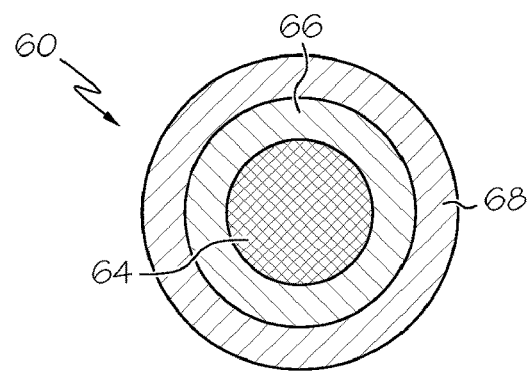
FIG. 7A depicts a gastric magnetic susceptibility phantom for equipment verification.
Figure 7B:
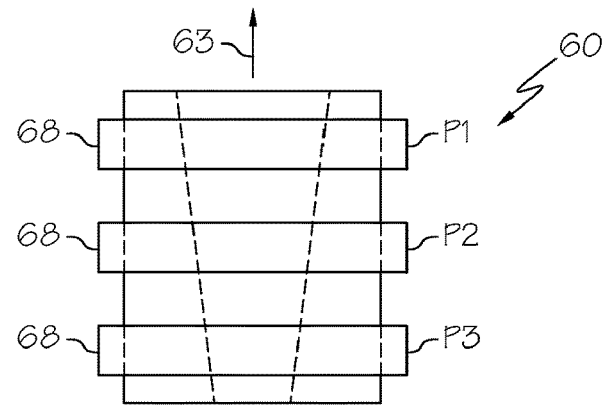
FIG. 7B depicts a view along the longitudinal axis of the phantom of FIG. 7A.

The peristaltic pump is filled with a magnetic contrast material and the pump is set to a speed consistent with the speed of human swallowing. As shown in FIG. 7B, a side view of the embodiment shown in FIG. 7A, the test laparoscopically adjustable gastric markers are positioned about the pump 60 at three positions, P1, P2, and P3. The first, second, and third markers are offset from one another along the longitudinal axis 63 of the pump.

Figure 8:
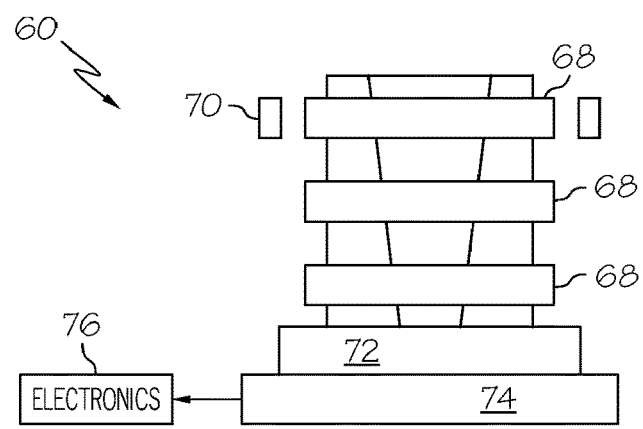
FIG. 8 shows an adjustable outer coil 70 moved such that it is positioned about the markers 68.

Referring now to FIG. 8, the adjustable outer coil 70 is moved such that it is positioned about the markers 68. The resonance frequency of each of the markers 68 positioned about the pump is measured. The resonance frequencies are measured while the magnetic material passes through the phantom into the receptor 72 and back through the pump again. The values of the resonance frequencies are detected by the pickup coil 74 and transmitted to external electronics 76 for further calculations. The maximum deviation of the resonance frequency is determined from a spectrum analyzer.

Figure 9:
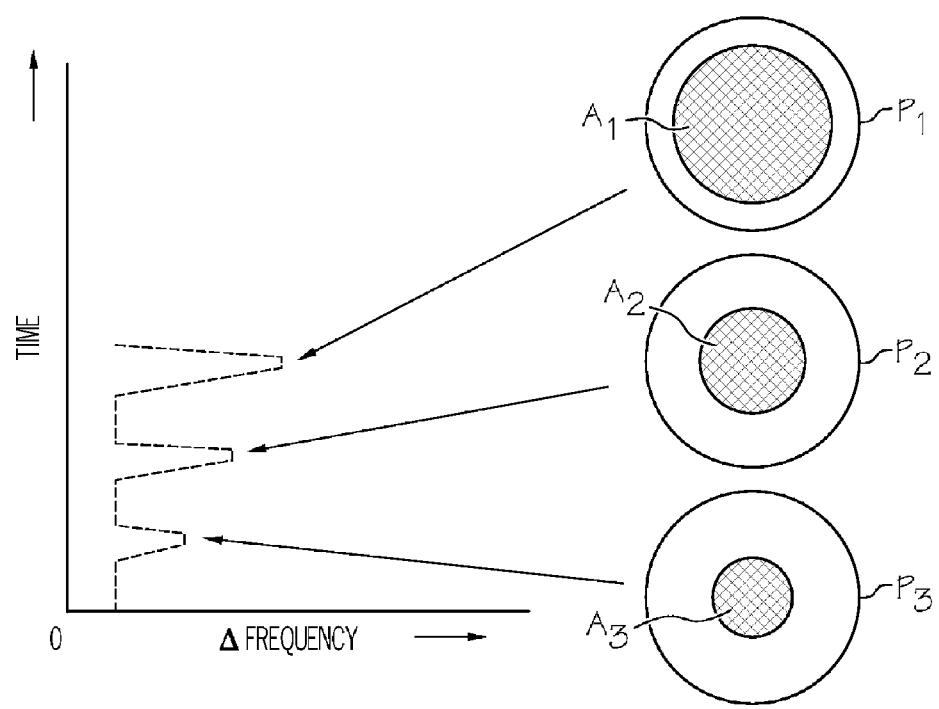
FIG. 9 depicts a change in frequency graphically correlated to geometric characteristics.

The above technique does not give an image of the intragastric device or surrounding anatomy inside the body. However, the data collected can be displayed graphically, as shown in FIG. 9. As seen in FIG. 9, the change in frequency can be graphically correlated to geometric characteristics, such as areas A1, A2, and A3 of the markers placed at positions P1, P2, and P3, respectively. As such, a practitioner can be assured that the external coil is working properly by comparing known good values of the A1, A2, and A3 versus the values that were measured during the verification procedure.

It should be noted that the external frequency generating apparatus described earlier can be modified to scan across the gastric lumen using appropriate radiofrequency excitation, thereby mimicking a rudimentary flow sensing magnetic resonance imaging apparatus. Such an apparatus would provide an image, using appropriate frequency domain software.

Figure 10:
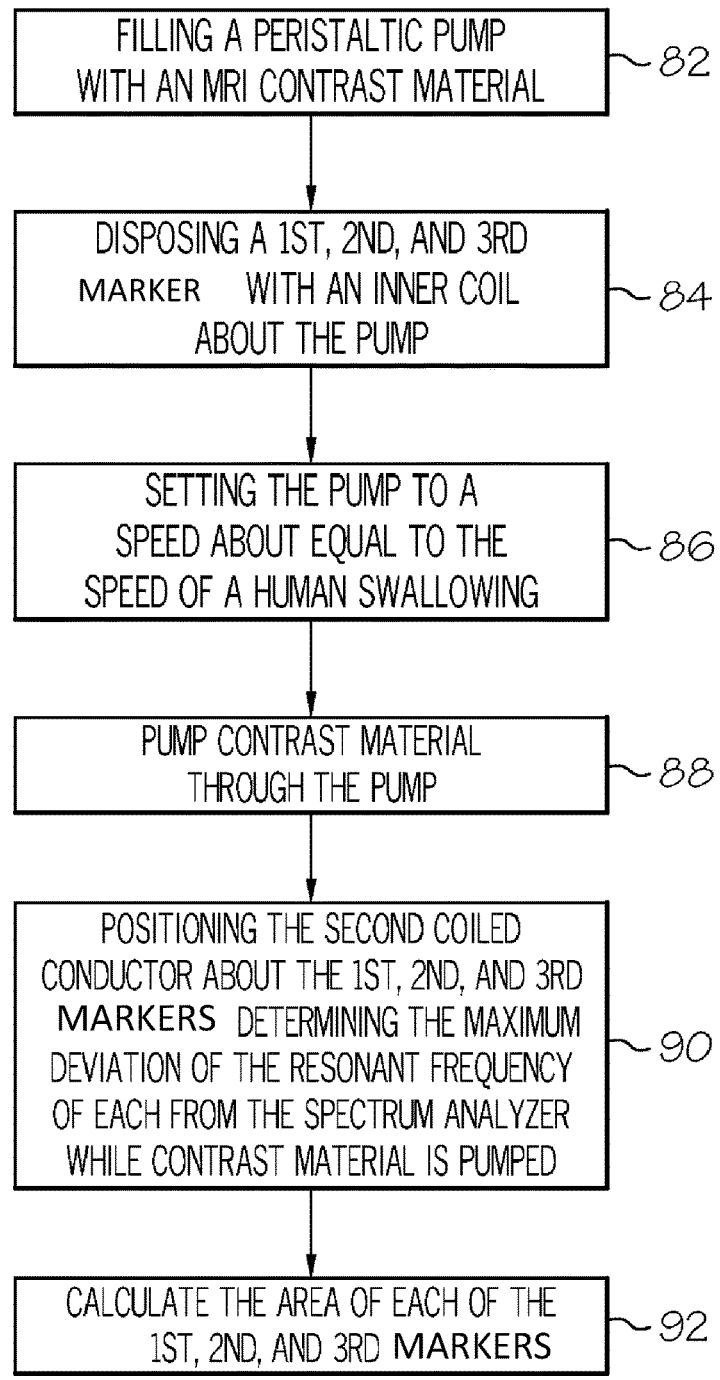
FIG. 10 depicts flowchart for a method of determining the size of a gastric lumen using a gastric magnetic susceptibility phantom.

The method of determining the size of a gastric lumen using a gastric magnetic susceptibility phantom is shown in FIG. 10. The method 80 includes the step 82 of filling a peristaltic pump with water or a water solution containing a magnetic resonance imaging contrast material. The method further includes the step 84 of disposing a first, second, and third marker or device, as described earlier with an internal coil, about the peristaltic pump. The first, second, and third markers are offset from one another along the longitudinal axis of the pump. The method further includes the step 86 of setting the pump to a speed approximately equal to the speed of human swallowing. The method further includes the step 88 of pumping the contrast material through the pump. The method further includes the step 90 of positioning the external coil 70 of FIG. 8 about the first, second, and third markers in turn and determining the maximum deviation of the resonant frequency of the each of the first, second, and third markers from the spectrum analyzer while contrast material is pumped through the pump. The method further includes the step 92 of calculating the area of each of the first, second, and third markers based on their resonant frequencies.

It should be noted that the steps in the method described in FIG. 10 need not be performed in the order shown, and as such, the method should not be limited to a particular order. Rather, a person of ordinary skill in the art will recognize that the method will perform equally well if, for example, the pump is set to a certain speed prior to filling it with the water solution.

Figure 11:
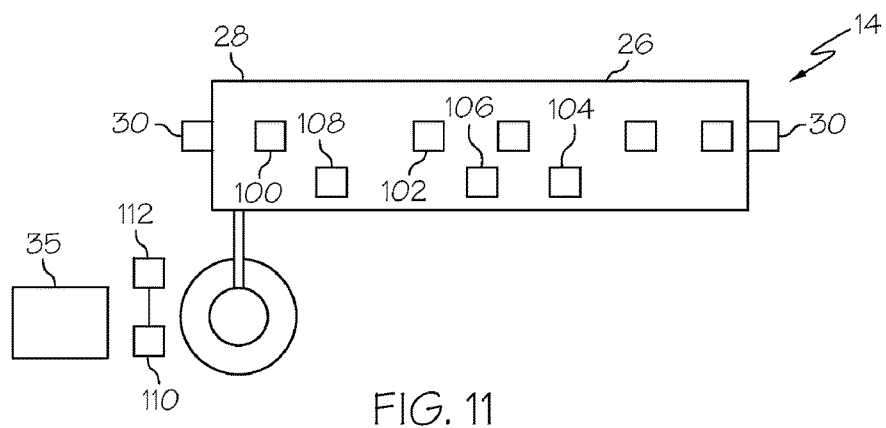
FIG. 11 depicts a system for characterizing an intragastric device, such as measuring the size of the device.

Referring now to FIGS. 11-14, a system for characterizing an intragastric device, such as measuring the size of the device, is illustrated in accordance with at least one embodiment of the present invention. FIG. 11 is similar to FIG. 3. However, instead of an internal coil, the embodiment depicted in FIG. 11 has two ultrasonic modules placed in the device that allow the system to measure the size and composition of the marker and/or device using time of flight ultrasound technology.

The time between transmission of the ultrasonic pulse and reception of the echo is given by:

$$t = 2 \cdot d / U, \tag{52}$$

Or $$d = U \cdot t / 2, \tag{53}$$

where U is the speed of sound in the medium, typically water, and d is the diameter of the device or marker of interest.

If the speed of sound is known, a dimension can be computed from the time between transmission and reception. If transmission occurs in two orthogonal directions, two dimensions of the marker can be determined, and thus the area of the marker can be computed. Assuming the lumen is an ellipse, the equation for the area of an ellipse using the major (a) and minor (b) axes is as follows:

$$A = \pi \cdot a \cdot b = (\pi \cdot U^2 \cdot t_1 \cdot t_2)/16 \tag{54}$$

The marker may be differentiated from the gastric tissue by instructing the patient to drink water, thus flushing the gastric area. If the marker is clear, a clear echo signal is obtained and the time of flight of the ultrasound pulse is obtained in the clear area to determine marker area.

To detect the presence of persistent solid mater, two methods are used. First, the orthogonal signal, that is the amplitude of the scattered ultrasonic pulse in the orthogonal direction, is compared with the original pulse echo return. And second, the amount of false return in the original pulse echo may even determine the ratio of solid to liquid matter in the cross section of the area encompassed by the marker.

Referring now to FIG. 11, the intragastric device 14 includes two orthogonal ultrasonic transmitter/receiver ("transceiver) modules 100, 102. Transceiver 100 is an anterior/posterior (a/p) ultrasonic module, and transceiver 102 is a lateral ultrasonic module.

The device 14 further includes a microprocessor 104 that measures the time of flight from each transceiver module. The microprocessor is capable of distinguishing between tissue echoes and an empty marker. The microprocessor is also capable of preparing a signal for transmission. The microprocessor is in electrical communication with a computer 105. In some embodiments, the computer and the microprocessor are incorporated into the same component. In at least one embodiment, the computer may be a look up table, capable of determining the semi-major axis, the semi-minor axis, and the scatter associated with the lumen.

The intragastric device 14 also includes a transmitter 106 capable of transmitting the signals from the marker to a location outside of the body. The transmitter 106 can include an antenna for transmission, or an antenna in the band (not shown) can be in electrical communication with the transmitter. The device 14 also includes a module 108 either containing a battery or capable of powering the laparoscopically adjustable gastric band electronics inductively.

External to the patient is an antenna 110 for receiving the transmitted signals and a receiver 112 in operative communication with the antenna. As before, a computer 35 may be included that has software capable of decoding and processing the signals transmitted by the transmitter 106 and received by the receiver 1 12. The computer software is capable of measuring the time of flight of horizontal and vertical ultrasonic pulses to determine the length and width of the device 14 and/or marker, and combining the length and width to find the area. It should be noted that from the scatter of the horizontal into the vertical receiver and the scatter of the vertical into the horizontal receiver, the material in the area of interest can be determined.

Figure 12:
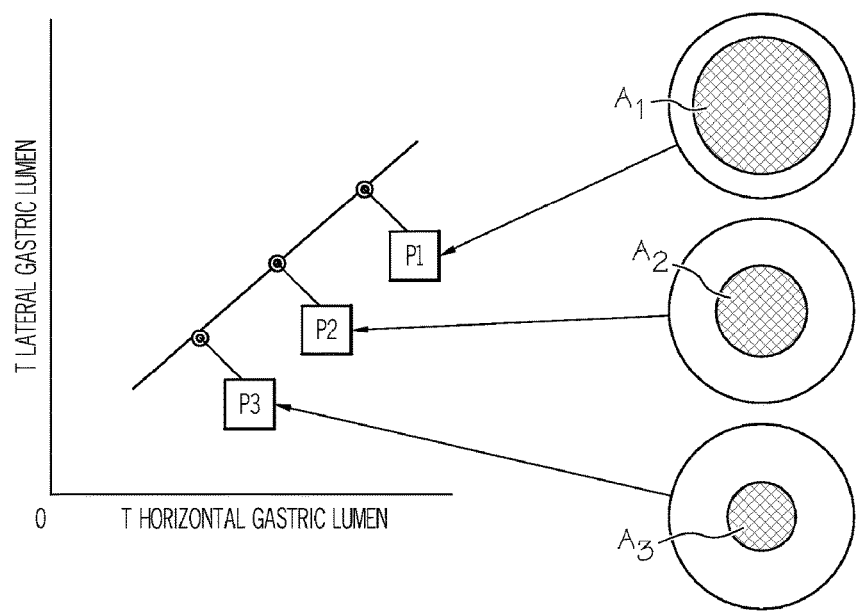
FIG. 12 depicts the lateral and horizontal times of flight graphically correlated to areas of the marker or device.

The ultrasonic system can be calibrated in a manner similar to that described above with regards to FIGS. 7 and 8. The above technique does not give an image of the device 14 or marker or internal anatomy. However, the data collected can be displayed in a graphical manner, as shown in FIG. 12. As seen in FIG. 12, the lateral and horizontal times of flight can be graphically correlated to the areas A1, A2, and A3 of the marker or device 14 placed at positions P1, P2, and P3, respectively.

In some embodiments, the device 14 or marker has an inner side and an outer side where the inner side is closer to the gastric lumen than the outer side, and the two ultrasonic modules are positioned on the outer side of the device, as in FIG. 11.

Figure 13:
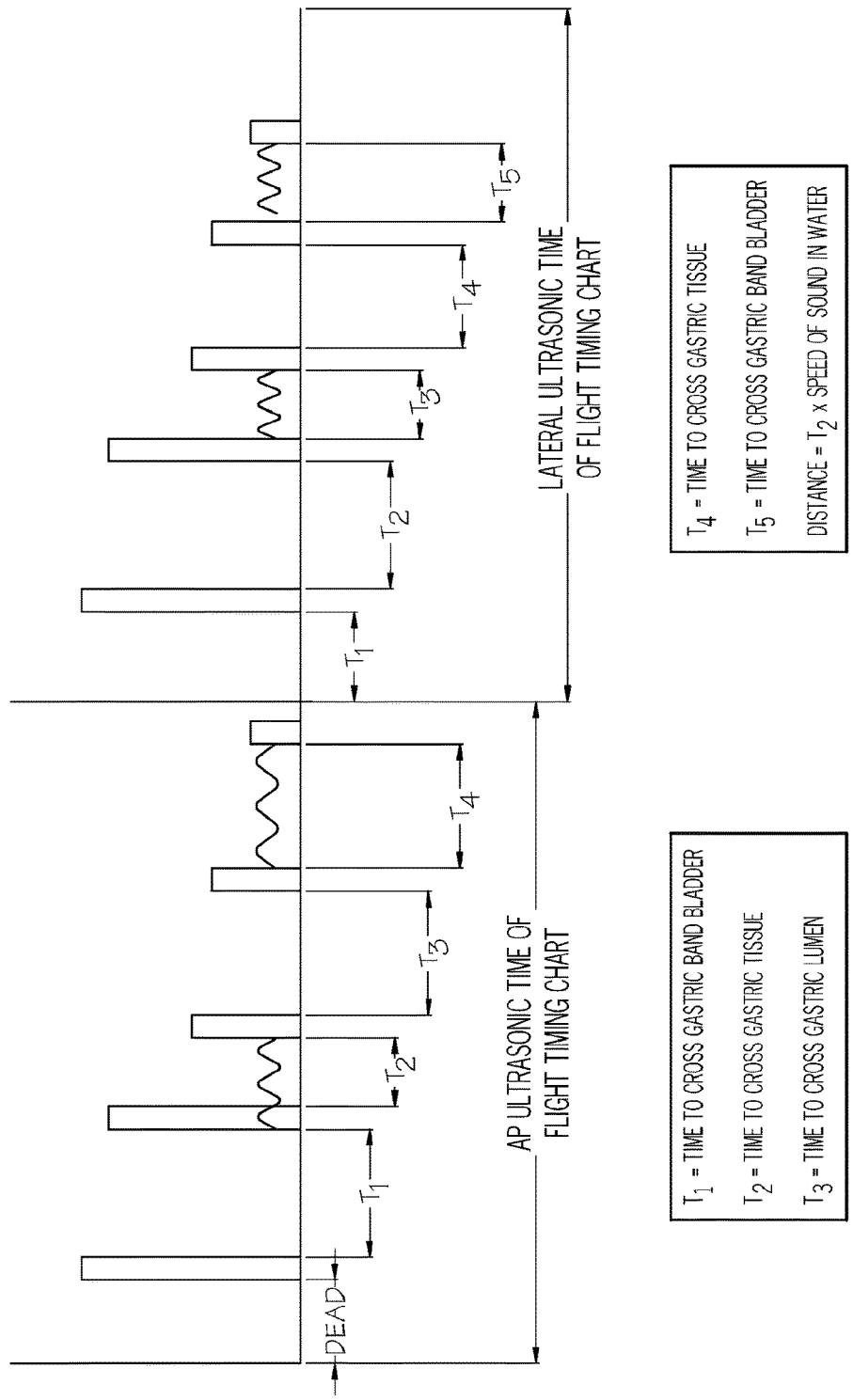
FIG. 13 depicts a pulse timing diagram depicting the time of flight using ultrasonic modules.

FIG. 13 depicts a pulse timing diagram depicting the time of flight using ultrasonic modules. Here, it is assumed that the device 14 or marker is a gastric band about a lumen. As seen in FIG. 13, the time of flight can be determined based on the time to cross the gastric band bladder, the time to cross the gastric tissue, and the time to cross the gastric lumen.

Figure 14:
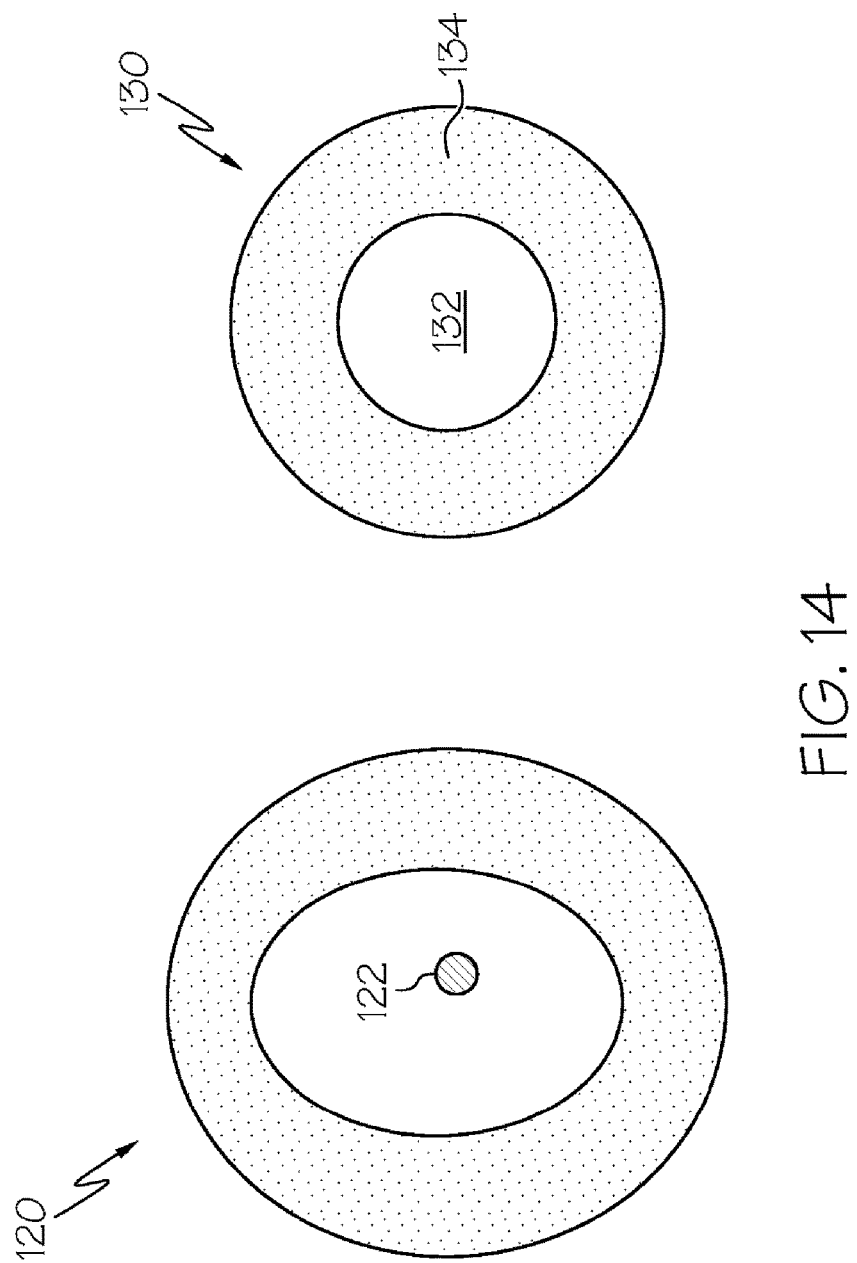
FIG. 14 is a graphically representation of the data collected for both the ultrasonic embodiment 120 and the induction embodiment 130.

FIG. 14 is a graphically representation of the data collected for both the ultrasonic embodiment 120 and the induction embodiment 130. The ultrasonic embodiment 120 is able to detect any solid mass 122 within the lumen. In the induction embodiment 130, the area 132 from the induction embodiment is depicted as well as the area 134 from the adjustable gastric band tab circumference minus the area from the induction area.

In some embodiments the ultrasound marker is a liquid, solid, or combination thereof. The various materials may be contained in a sac in or on the intragastric device. The properties of the liquid may be tuned such that the acoustic signature is easily identified.

The above techniques may be used with an ultrasound marker and applied to the volume-occupying subcomponent when the volume-occupying subcomponent is in a creased or folded state such that when the volume-occupying subcomponent is in its deflated state the marker has a characteristic ultrasound visualization or signature, and when the volume-occupying subcomponent is inflated the marker has another characteristic ultrasound visualization or signature. Alternatively, the ultrasound marker may be applied or incorporated into the volume-occupying subcomponent so as to facilitate identification and location of the various subcomponents of the device, such as a valve, head, or weight. The ultrasound marker may be printed or painted onto a surface of the volume-occupying subcomponent or between layers of the material forming the volume-occupying subcomponent. Alternatively, an acoustically-responsive coating may be used as an ultrasound marker to assist with identifying and/or locating the volume-occupying subcomponent. Alternatively, the ultrasound marker may be applied to an elastomeric sleeve that covers all or part of the volume-occupying subcomponent.

In another embodiment, the volume-occupying subcomponent incorporates a subcomponent that changes mechanically upon inflation of the volume-occupying subcomponent, which mechanical change can be determined using the ultrasound visualization equipment. For example, a mechanical portion of the volume-occupying subcomponent containing an ultrasound visualization marker may elongate upon an increase in pressure in the volume-occupying subcomponent.

Alternatively, a ultrasound marker may be formed using a mesh, for example a metallic mesh, located between layers of the material from which the volume-occupying subcomponent is constructed. The pattern or patterns formed by the imbedded ultrasound marker will appear when the volume-occupying subcomponent is in an inflated, deployed state.

In some embodiments, an ultrasound sensor comprises a non-contact sensor. An ultrasonic level or sensor or sensing system requires no contact with the target. In the medical industries this is an advantage over inline sensors that may contaminate or otherwise interfere with the marker or item of interest. In some embodiments, the sensor is a microphone.

In some embodiments, a pulsed wave system is used. The principle behind a pulsed-ultrasonic technology is that the transmit signal consists of short bursts of ultrasonic energy. After each burst, the sensor electronics looks for a return signal within a small window of time corresponding to the time it takes for the energy to pass through the medium of interest. Only a signal received during this window will qualify for additional signal processing. In some embodiments a continuous wave system is used. In the pulsed, continuous, or other wave systems, the sensor may be a microphone that receives the return wave signal.

In some embodiments, a marker may transmit ultrasound signals. For instance, Ultrasound Identification (USID) may be used to automatically track and identify the location of intragastric devices in real time using simple, inexpensive nodes (badges/tags) attached to or embedded in the ultrasound devices, which then transmit an ultrasound signal to communicate their location to ultrasound sensors, such as microphones.

A computing system may be implemented in the ultrasound locating system. The computing system comprises hardware and software that receives data from the ultrasound sensor and calculates information related to the location, orientation, and/or state of an intragastric device according to certain algorithms. In some embodiments, the hardware may comprise a central processing unit, memory, an analog to digital converter, analog circuitry, a display. In some embodiments, the software proceeds through a number of steps including calibration, initialization, prediction, estimation, measuring magnetic sensor data, calculating various desired outputs including location, orientation, size, configuration, etc. in accordance with the techniques discussed herein.

The processor's output relating to the location, orientation and/or state of an intragastric device may be communicated to a user in a number of manners. In some embodiments, the output is shown visually on a display.

In some embodiments, the processor's output related to an intragastric device's location, orientation, and/or state is audibly communicated to a user through a speaker.

In some embodiments, the processor's output related to an intragastric device's location, orientation, and/or state is communicated to a user through a combination of methods. For instance, the system may employ a visual graphical display with audible alerts sent through speakers.

In some embodiments, the ultrasound locating system is calibrated before use. The ultrasound marker and the sensor are positioned in pre-planned locations and orientations to verify the output signal is within an expected range. In some embodiments, the ultrasound locating systems are calibrated or otherwise verified using a human patient simulator, or dummy, to test the ultrasound locating system as a ultrasound marker travels through the simulator. In some embodiments, the ultrasound locating system is checked for stray signals from nearby acoustic interferences.

The ultrasound sensor may be used in conjunction with the marker or markers in a variety of embodiments to locate or otherwise characterize an ingested intragastric device. In some embodiments, an off-the-shelf intragastric device, such as a swallowable, inflatable balloon, may be used without modification with any ultrasound markers. With that device, an ultrasound sensor that pulses sound waves and senses their return signal with a microphone may be used outside the body. The device could be swallowed in a deflated state and would then inflate once inside the stomach. The ultrasound sensor may be used to locate or otherwise characterize the device by pulsing the device and receiving the return signals, in accordance with the techniques discussed above.

The devices once ingested may be located using the ultrasound intragastric locating system. In some embodiments, the sensor may locate the device by pulsing in various locations and analyzing the return signal. For instance, a return signal corresponding to a body organ without the device may be pre-determined by correlating a return wave signal to a location on the body before the device is swallowed. This could produce an ultrasound map of the organ or body without any device. Then, after swallowing the device, and by running the sensor over the body, if a different signal is returned for a corresponding location in the body, then the location of the device is thus identified. This may be implemented in accordance with the techniques discussed above.

The orientation of the devices once ingested may be ascertained using the ultrasound intragastric locating system. In some embodiments, the sensor may identify the orientation of the intragastric device by pulsing and sensing at various locations of the device and analyzing the return signals. For instance, before ingestion by a patient, the device may be pulsed at various orientations such that a pre-determined database exists of known correlations between return wave signatures and orientation of the device. This may be done for the device in the deflated, inflated, or other states. Then, after ingestion, the device may be pulsed and the return signals compared to the pre-determined database to determine the orientation of the device in accordance with the techniques discussed above.

Further, the various sizes and configurations of the devices once ingested may be characterized using the ultrasound intragastric locating system in accordance with the techniques discussed above. For instance, inflation of a balloon, or the inflation or configuration of multiple balloons, may be characterized and assessed. In some embodiments, the sensor may characterize the device or devices by pulsing and sensing at various locations of the device and analyzing the return signals. For instance, the deflated device would return a different pulsed signature than the inflated device. In such a manner, the device may be characterized as either inflated, deflated, or in some other state. The inflated device could further be characterized before ingestion by a patient such that the return signal signature is pre-determined and serves as a guidepost for assessing the state of the device. In some embodiments, the ultrasound locating system may be used in conjunction with a deflating system to characterize the deflation process.

The timing and other attributes of the various methods of administration can be characterized using the disclosed ultrasound intragastric locating system and techniques. Whether the device is administered using endoscopic techniques or orally, the progress of the device as it makes its way to the stomach can be tracked with the ultrasound locating system. For instance, the effects of swallowing the device with hard gelatin or water or other consumables may be characterized by tracking the location and orientation as it is ingested.

In some embodiments, the ultrasound locating system may characterize an intragastric device that has a circular or elliptical cross-section. Two ultrasonic modules placed in the device allow the system to measure the size and composition of the device using time of flight ultrasound technology.

Using the speed of sound, a distance can be computed from the time between transmission and reception. The time between transmission of the ultrasonic pulse and reception of the echo is given by: $t=2d/U$, or $d=Ut/2$, (53) where U is the speed of sound in the medium of interest, and d is the diameter of the device. If transmission occurs in two orthogonal directions, two dimensions of the intragastric device can be determined, and thus the area of the device can be computed. Assuming the device is an ellipse, the equation for the area of an ellipse using the major (a) and minor (b) axes is as follows:

$$A=\pi \cdot a \cdot b=(\pi \cdot U^2 \cdot t_1 \cdot t_2)/16$$

If the interior of an inflated device is clear, a clear echo signal is obtained and the time of flight of the ultrasound pulse is obtained in the clear area to determine device area. To detect the presence of matter, foreign or otherwise, in the device, two methods may be used. First, the orthogonal signal, that is the amplitude of the scattered ultrasonic pulse in the orthogonal direction, is compared with the original pulse echo return. And second, the amount of false return in the original pulse echo may even determine the ratio of solid to liquid matter in the analyzed cross section of the device.

The intragastric device may include two orthogonal ultrasonic transmitter/receiver ("transceiver") modules. One transceiver is an anterior/posterior (a/p) ultrasonic module, and the other transceiver is a lateral ultrasonic module. The device further includes a microprocessor that measures the time of flight from each transceiver module. The microprocessor is capable of distinguishing between device echoes and the empty device interior. The microprocessor is also capable of preparing a signal for transmission. The microprocessor is in electrical communication with a computer. In some embodiments, the computer and the microprocessor are incorporated into the same component. In at least one embodiment, the computer may be a look up table, capable of determining the semi-major axis, the semi-minor axis, and the scatter associated with the device.

The intragastric device may also include a transmitter capable of transmitting the signals from the device to a location outside of the body. The transmitter can include an antenna for transmission, or an antenna in the band (not shown) can be in electrical communication with the transmitter. The device may also include a module either containing a battery or capable of powering the intragastric device electronics inductively. External to the patient may be an antenna for receiving the transmitted signals and a receiver in operative communication with the antenna. A computer may be included that has software capable of decoding and processing the signals transmitted by the transmitter and received by the receiver. The computer software is capable of measuring the time of flight of horizontal and vertical ultrasonic pulses to determine the length and width of the intragastric device, and combining the length and width to find the area. It should be noted that from the scatter of the horizontal into the vertical receiver and the scatter of the vertical into the horizontal receiver, the presence of any material in the device can be determined.

In some embodiments, the ultrasonic system can be calibrated. The data collected can be displayed in a graphical manner with the lateral and horizontal times of flight graphically correlated to various areas of the intragastric devices.

In some embodiments, the intragastric device has an inner side and an outer side where the inner side being closer to the intragastric device interior than the outer side, the two ultrasonic modules being positioned on the outer side of the intragastric device. The time of flight can be determined based on the time to cross the intragastric device.

EXAMPLES

Film Permeability

A variety of different composite films were tested for permeability of gases as measured by $CO_2$ diffusion at 37° C. As shown in the data of Table 3, the permeability of varying composite wall constructions were evaluated and determined by their resistance to $CO_2$ diffusion rates, where the smaller the permeability test result, the higher barrier to gas diffusion the film provides. As noted, the permeability of the film and degree of barrier the film provides to gas diffusion was derived using $CO_2$ at 37° C., one of the most permeable gasses. This can be used as a surrogate to other gas diffusion rates where generally $CO_2$ is 3 to 5 times faster in diffusion across a membrane than oxygen, and nitrogen is 0.2 to 0.4 times faster than the oxygen transmission rate when these are evaluated at 25° C. As Table 3 indicates, permeability of the film is also affected by orientation of the film (which layer is exposed to the $CO_2$ gas first), and Relative Humidity. The walls were tested under conditions of low relative humidity (0%, representative of conditions inside the balloon upon fill) and high relative humidity (100%, representative of in vivo conditions). In certain embodiments, a composite wall having a permeability of <10 cc/m²/day is generally preferred; however, depending upon the desired effect of inflation and re-inflation by in vivo gasses such as $CO_2$, a higher permeability of >10 cc/m²/day in in vivo conditions can be desirable. For example, each of the films in the table can be suitable for use in various selected embodiments, such that the resulting balloon wall has a permeability to $CO_2$ of even greater than >10 cc/m²/day, e.g., >50 cc/m²/day, >100 cc/m²/day, >200 cc/m²/day, >300 cc/m²/day, >400 cc/m²/day, >500 cc/m²/day, >750 cc/m²/day, >1000 cc/m²/day, >1500 cc/m²/day, >2000 cc/m²/day, >2500 cc/m²/day, >3000 cc/m²/day, >3500 cc/m²/day, or even >4000 cc/m²/day. In selected embodiments, it is generally preferred to have a permeability of from about 1, 2, 3, 4, 5, 6, 7, 8, 9, or 10 cc/m²/day to about 15, 20, 25, 30, 35, 40, 45, 50, 60, 70, 80, 90, 100, 110, 120, 130, 140 or 150 cc/m²/day.

TABLE 3

| Film | Film Thickness (in) | Innermost Layer ($CO_2$ Exposed Layer) | RH % | Permeability Test Results (cc/m2/day) (1 ATM/37° C.) |
|---|---|---|---|---|
| PE/EVOH/PE | 0.002 ± 0.001 | PE | 0 | 10.8 |
| 70% Nylon 6,66, 30% MXD6/EVOH/PVDC/70% Nylon 6,66, 30% MXD6/LLDPE + LDPE | 0.003 | Nylon 6,66 | 0 | 2.4 |
| 70% Nylon 6,66, 30% MXD6/EVOH/PVDC/70% Nylon 6,66, 30% MXD6/LLDPE + LDPE | 0.003 | Nylon 6,66 | 95 ± 5 | 51.0 |
| 70% Nylon 6,66, 30% MXD6/EVOH/PVDC/70% Nylon 6,66, 30% MXD6/LLDPE + LDPE | 0.003 | LDPE | 95 ± 5 | 3.3 |
| 70% Nylon 6,66, 30% MXD6/PVDC/70% Nylon 6,66, 30% MXD6/LLDPE + LDPE | 0.002 | LDPE | 0 | 43.0 |
| 70% Nylon 6,66, 30% MXD6/PVDC/70% Nylon 6,66, 30% MXD6/LLDPE + LDPE | 0.003 | LDPE | 0 | 50.0 |
| 70% Nylon 6,66, 30% MXD6/PVDC/70% Nylon 6,66, 30% MXD6/LLDPE + LDPE | 0.002 | LDPE | 95 ± 5 | 41.0 |
| 70% Nylon 6,66, 30% MXD6/PVDC/70% Nylon 6,66, 30% MXD6/LLDPE + LDPE | 0.003 | LDPE | 95 ± 5 | 49.0 |
| Bi-axially Oriented PP/EVOH/PE | 0.00125 | LDPE | 0 | 15.4 |
| Bi-axially Oriented PP/EVOH/PE | 0.00175 | PE | 0 | 8.2 |
| Bi-axially Oriented PP/EVOH/PE | 0.00125 | PE | 95 ± 5 | 282.6 |
| Bi-axially Oriented PP/EVOH/PE | 0.00125 | PE | 95 ± 5 | 1088.0 |
| Bi-axially Oriented PP/EVOH/PE | 0.00175 | PE | 95 ± 5 | 235.4 |
| Cast PP | 0.002 ± 0.001 | NA | 0 | 772.0 |
| Cast PP/PE/EVOH/PE | 0.0025 | PE | 0 | 7.2 |
| Cast PP/PE/EVOH/PE | 0.0025 | PE | 0 | 10.1 |
| Cast PP/PE/EVOH/PE | 0.0025 | PE | 95 ± 5 | 169.3 |
| Cast PP/PE/EVOH/PE | 0.0025 | PE | 95 ± 5 | 18.5 |
| Coextruded PE/EVOH/PE | 0.00125 | PE | 0 | 8.1 |
| Coextruded PE/EVOH/PE | 0.0015 | PE | 0 | 4.9 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| Coextruded PET/SiOx/PE | 0.002 ± 0.001 | PE | 0 | 12.4 |
| CoExtrude-LLDPE/HDPE/EVOH/HDPE | 0.0025 | HDPE | 0 | 1.7 |
| HDPE/HDPE/PVdC/EVOH/HDPE/LLDPE + LDPE | 0.003 | HDPE | 0 | 5.0 |
| HDPE/HDPE/PVdC/EVOH/HDPE/LLDPE + LDPE | 0.003 | HDPE | 95 ± 5 | 6.8 |
| HDPE/HDPE/PVdC/EVOH/HDPE/LLDPE + LDPE | 0.003 | LDPE | 0 | 4.4 |
| HDPE/HDPE/PVdC/EVOH/HDPE/LLDPE + LDPE | 0.003 | LDPE | 95 ± 5 | 52.0 |
| HDPE/HDPE/PVdC/HDPE/HDPE/LLDPE + LDPE | 0.003 | LDPE | 0 | 74.0 |
| HDPE/HDPE/PVdC/HDPE/HDPE/LLDPE + LDPE | 0.003 | LDPE | 0 | 47.0 |
| HDPE/HDPE/PVdC/HDPE/HDPE/LLDPE + LDPE | 0.003 | LDPE | 95 ± 5 | 68.0 |
| HDPE/HDPE/PVdC/HDPE/HDPE/LLDPE + LDPE | 0.003 | LDPE | 95 ± 5 | 44.0 |
| Kurarister ™ C, 3 mil | 0.003 | UNK | 0 | 3.2 |
| Nylon12/PvDC/Nylon12/LLDPE + LDPE | 0.003 | LLDPE + LDPE | 0 | 52.0 |
| Nylon12/PvDC/Nylon12/LLDPE + LDPE | 0.003 | LLDPE + LDPE | 95 ± 5 | 56.0 |
| MPI Supernyl LLDPE 40 μm | 0.0022 | LLDPE | 0 | 3.3 |
| MPI Supernyl LLDPE 40 μm | 0.0022 | LLDPE | 95 ± 5 | 5.8 |
| MPI Supernyl LLDPE 50 μm | 0.0026 | LLDPE | 0 | 4.2 |
| MPI Supernyl LLDPE 50 μm | 0.0026 | LLDPE | 95 ± 5 | 7.5 |
| Nylon12/PvDC/Nylon12/LLDPE + LDPE | 0.003 | LLDPE + LDPE | 0 | 59.3 |
| Nylon12/PVDC/Nylon12/LLDPE + LDPE | 0.003 | LLDPE + LDPE | 95 ± 5 | 29.5 |
| Nylon12/PVDC/Nylon12/LLDPE + LDPE - Thermoformed | 0.003 | LLDPE + LDPE | 0 | 73.2 |
| Nylon12/PVDC/Nylon12/LLDPE + LDPE | 0.0024 | LLDPE + LDPE | 0 | 77.0 |
| Nylon12/PVDC/Nylon12/LLDPE + LDPE | 0.0024 | LLDPE + LDPE | 95 ± 5 | 68.0 |
| Nylon12/PVdC/Nylon12/LDPE-Cast | 0.003 | LDPE | 0 | 58.0 |
| Nylon12/Nylon Tie/EVA/PVdC/Adhesive/Nylon12/Nylon Tie/LDPE-Cast | 0.003 | LDPE | 95 ± 5 | 54.0 |
| Nylon12/PVdC/Nylon12/LDPE | 0.0035 | LDPE | 0 | 14.9 |
| Nylon12/PVdC/Nylon12/LDPE | 0.004 | LDPE | 0 | 34.0 |
| Nylon12/PVdC/Nylon12/LDPE | 0.0035 | LDPE | 95 ± 5 | 24.9 |
| Nylon12/PVdC/Nylon12/LDPE | 0.0035 | LDPE | 95 ± 5 | 41.3 |
| Nylon12/PVdC/Nylon12/LDPE | 0.004 | LDPE | 95 ± 5 | 31.7 |
| Nylon 6,66/PVDC/Nylon6,66/LLDPE + LDPE | 0.0024 | LDPE | 0 | 54.0 |
| Nylon 6,66/PVDC/Nylon6,66/LLDPE + LDPE | 0.0024 | LDPE | 95 ± 5 | 56.0 |
| Nylon 6,66/EVOH/PVDC/Nylon 6,66/LDPE | 0.0032 | LDPE | 0 | 5.5 |
| Nylon 6,66/EVOH/PVDC/Nylon 6,66/LDPE | 0.0032 | LDPE | 95 ± 5 | 6.4 |
| Nylon 6,66/EVOH/PVDC/Nylon 6,66/LDPE | 0.0032 | Nylon 6,66 | 95 ± 5 | 49.9 |
| Nylon 6,66/PVDC/Nylon6,66/LLDPE + LDPE | 0.0027 | LDPE | 0 | 57.0 |
| Nylon 6,66/PVDC/Nylon6,66/LLDPE + LDPE | 0.003 | LDPE | 0 | 41.0 |
| Nylon 6,66/PVDC/Nylon6,66/LLDPE + LDPE | 0.0027 | LDPE | 95 ± 5 | 55.0 |
| Nylon 6,66/PVDC/Nylon6,66/LLDPE + LDPE | 0.003 | LDPE | 95 ± 5 | 46.0 |
| Multi-layer Nylon 12/LLDPE + LDPE | 0.0035 | LDPE | 0 | 3203.5 |
| Multi-layer Nylon 12/LLDPE + LDPE | 0.004 | LDPE | 0 | 2725.5 |
| Multi-layer Nylon 12/LLDPE + LDPE | 0.0045 | LDPE | 0 | 2553.6 |
| Multi-layer Nylon 12/LLDPE + LDPE | 0.0035 | LDPE | 95 ± 5 | 2539.3 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| Multi-layer Nylon 12/LLDPE + LDPE | 0.004 | LDPE | 95 ± 5 | 2527.8 |
| Multi-layer Nylon 12/LLDPE + LDPE + Parylene | 0.0045 | LDPE | 0 | 1522.6 |
| Multi-layer Nylon 12/LLDPE + LDPE + Parylene | 0.0045 | LDPE | 95 ± 5 | 1275.5 |
| NYLON-SIOX/HDPE/LLDPE | 0.003 | LLDPE | 95 ± 5 | 83.0 |
| NYLON-SIOX/HDPE/LLDPE | 0.003 | LLDPE | 0 | 70.0 |
| Nylon-SIOX/LLDPE | 0.0015 | LLDPE | 0 | 134.0 |
| Nylon-SIOX/LLDPE | 0.0015 | LLDPE | 95 ± 5 | 82.0 |
| OPP Co-extrude with mPE/EVOH/mPE | 0.002 | mPE | 0 | 5.9 |
| OPP Laminated to mPE/EVOH/mPE | 0.0025 | mPE | 0 | 4.7 |
| OPP Laminated to mPE/EVOH/mPE | 0.003 | mPE | 0 | 3.4 |
| OPP Laminated to mPE/EVOH/mPE | 0.0025 | mPE | 95 ± 5 | 294.3 |
| OPP SIOX/LLDPE | 0.002 | LLDPE | 0 | 540.5 |
| OPP SIOX/LLDPE | 0.002 | LLDPE | 0 | 1081.0 |
| OPP SIOX/LLDPE | 0.002 | LLDPE | 95 ± 5 | 565.0 |
| OPP SIOX/LLDPE | 0.002 | LLDPE | 95 ± 5 | 594.5 |
| OPP/mPE/EVOH/mPE | 0.0021 | mPE | 0 | 5.0 |
| OPP/mPE/EVOH/mPE | 0.0021 | mPE | 95 ± 5 | 437.1 |
| OPP/PE/EVOH/PE | 0.0025 | OPP | 0 | 8.5 |
| OPP/PE/EVOH/PE | 0.0025 | OPP | 95 ± 5 | 11.6 |
| OPP/PE/EVOH/PE | 0.00175 | PE | 0 | 8.1 |
| OPP/PE/EVOH/PE | 0.0025 | PE | 0 | 8.9 |
| OPP/PE/EVOH/PE | 0.0025 | PE | 0 | 18.6 |
| OPP/PE/EVOH/PE | 0.0025 | PE | 95 ± 5 | 259.0 |
| OPP/PE/EVOH/PE | 0.0025 | PE | 95 ± 5 | 556.1 |
| OPP/PVDC/mPE | 0.0017 | mPE | 0 | 74.2 |
| OPP/PVDC/mPE | 0.0017 | mPE | 95 ± 5 | 84.6 |
| OPP-SIOX/LLDPE | 0.002 ± 0.001 | LLDPE | 95 ± 5 | 1159.7 |
| Oriented PA | 0.002 ± 0.001 | NA | 0 | 750.9 |
| Oriented PP | 0.002 ± 0.001 | NA | 0 | 726.0 |
| PA/EVOH/PA/LLDPE | 0.0022 | LLDPE | 0 | 5.0 |
| PA/EVOH/PA/LLDPE | 0.0022 | LLDPE | 0 | 3.1 |
| PA/EVOH/PA/LLDPE | 0.0022 | LLDPE | 95 ± 5 | 10.8 |
| PE/EVOH/PE | 0.002 ± 0.001 | PE | 0 | 9.2 |
| PET | 0.001 | PE | 0 | 524.7 |
| SiOx-PET/EVOH/PE | 0.002 | PE | 0 | 1.4 |
| SiOx-PET/MPE/EVOH/mPE | 0.0016 | mPE | 0 | 1.0 |
| Si-Ox-PET/PE/EVOH/PE | 0.00125 | PE | 0 | 1.7 |
| Si-Ox-PET/PE/EVOH/PE | 0.0015 | PE | 0 | 1.6 |
| Si-Ox-PET/PE/EVOH/PE | 0.0015 | PE | 0 | 5.4 |
| Si-Ox-PET/PE/EVOH/PE | 0.002 | PE | 0 | 1.5 |
| Si-Ox-PET/PE/EVOH/PE | 0.002 | PE | 0 | 1.8 |
| Si-Ox-PET/PE/EVOH/PE | 0.002 | PE | 95 ± 5 | 22.6 |

Animal Studies

Two different composite walls were tested: a material (Nylon12/PvDC/Nylon 12/LLDPE+LDPE) with high barrier material characteristics and a material with low barrier characteristics (multi-layer Nylon12/LLDPE+LDPE). A series of experiments were performed using a mixture of 75% $N_2$ and 25% $CO_2$ as the balloon initial fill. As shown in the data of Table 4, each of the balloons maintained pressure over the duration tested, but gained substantially in volume. Considering the composite walls studied are not a metal canister (volume and pressure change due to material stretch) there was a significant change in the number of overall gas molecules inside the balloon from the initial gas fill. Since the internal balloon environment started with $CO_2$ and nitrogen, most likely additional $CO_2$ entered due to the environment the balloon was subjected to ($N_2$ and $CO_2$ headspace) but also most likely other gases available in the air as well as water vapor also diffused within the balloon wall.

TABLE 4

| Pig # | Balloon #, Wall Composition | Starting implant pressure (PSI) | Estd. Volume at implant | Explant Volume (cc) | Explant Pressure (PSI) | % $CO_2$ in balloon (meas. w/ $CO_2$ meter) | Measured % $CO_2$ in stomach gas (%) | Final Vol. | % gas gain (calc.) |
|---|---|---|---|---|---|---|---|---|---|
| 1 | 1, Barrier Material (Nylon/Saran) | 1.0 | 277 | 360 | 1.1 | 22% | 10% | 385 | 23.5 |
| 1 | 2, Barrier Material (Nylon/Saran) | 1.09 | 282 | 340 | 0.7 | 19.63% | 10% | 358 | 15 |

TABLE 4-continued

| Pig # | Balloon #, Wall Composition | Starting implant pressure (PSI) | Estd. Volume at implant | Explant Volume (cc) | Explant Pressure (PSI) | % $CO_2$ in balloon (meas. w/ $CO_2$ meter) | Measured % $CO_2$ in stomach gas (%) | Final Vol. | % gas gain (calc.) |
|---|---|---|---|---|---|---|---|---|---|
| 2 | 3, Non-Barrier Material (Nylon) | 1.15 | 283 | 330 | 1.2 | 26.57% | 8% | 320 | 14.5 |
| 2 | 4, Non-Barrier Material (Nylon) | 1.07 | 281 | 323 | 0.96 | 31% | 8% | 316 | 12.4 |

Volume gains were higher for the barrier material composite walls than for the non-barrier walls. An analysis of gas in the balloons after explants (Tables 5a and 5b) showed gains in oxygen, hydrogen, and argon in addition to the nitrogen and carbon dioxide that was already present in the balloon at initial inflation. The balloons, both with a good barrier composite wall (table 5a) and a poor barrier composite wall (table 5b) both gained in overall volume while maintaining pressure after 30 days in vivo. Explant results of the balloon with a composite wall containing a good barrier material (#2, table 5a) showed a slightly higher increase in carbon dioxide than the wall without a barrier material (#3, table 5b). It is unlikely that nitrogen diffused in or out of the balloon due to its inertness as well as the external gastric environment most likely matched the internal concentration of nitrogen such that there was no (or an insignificant) diffusion gradient for the nitrogen gas.

TABLE 5a

| Gas | % v/v, by MS | Detection Limit |
|---|---|---|
| Nitrogen | 64.04 | 0.01 |
| Oxygen | 7.63 | 0.01 |
| Argon | 0.60 | 0.01 |
| Carbon Dioxide | 19.63 | 0.01 |
| Hydrogen | 8.10 | 0.01 |
| Helium | not detected | 0.01 |
| Methane | not detected | 0.01 |

TABLE 5b

| Gas | % v/v, by MS | Detection Limit |
|---|---|---|
| Nitrogen | 62.33 | 0.01 |
| Oxygen | 9.27 | 0.01 |
| Argon | 0.7 | 0.01 |
| Carbon Dioxide | 26.57 | 0.01 |
| Hydrogen | 1.13 | 0.01 |
| Helium | not detected | 0.01 |
| Methane | not detected | 0.01 |

The data show that when it is desirable to minimize volume gain over the useful life of the device, a non-barrier composite wall material may be more desirable than a barrier wall. This observation is contrary to conventional wisdom that seeks to maintain the initial fill of gas in the balloon by maximizing barrier properties of the intragastric balloon wall.

Simulated Gastric Environment

Balloons constructed with non-barrier film composite walls were tested (multi-layer Nylon 12/LLDPE+LDPE) in a simulated gastric environment (tank containing a 1.2 pH HCl solution with NaCl and pepsin at 40° C. with a variable $N_2/CO_2$ headspace; samples were taken at peak $CO_2$ at 50% and trough $CO_2$ at 0% in the tank). The balloons were initially filled with either pure $N_2$ or a mixture of $N_2$ (75%) and $CO_2$ (25%), and pressure, volume, and gas gain were monitored over time. The balloon filled with pure nitrogen exhibited significantly higher gain of $CO_2$ when compared to the balloon filled with the $N_2/CO_2$ mixture. When a volume gain (as manifested in a gain of $CO_2$ gas) is desired, pure nitrogen as the initial fill gas in connection with a non-barrier film is desirable. Data for the experiments is provided in Table 6.

TABLE 6

| Expt. # | Material OGB # | Sample # | Balloon Internal Gas N2 or N2/CO2 | Pressure (Day 0) T = 0 (psi) | Volume (Day 0) T = 0 (cc) | Volume (Day 1) End of Cycle T = 1 (cc) | Volume (Day 2) 50% $CO_2$ T = 2 (cc) | Pressure (Day 2) 50% $CO_2$ T = 2 (psi) |
|---|---|---|---|---|---|---|---|---|
| 1 | Non-Barrier Film | 1 | N2 | 1.12 | 304 | 312 | 314 | 1.84 |
|   |   | 3 |   | 1.12 | 300 | 310 | 313 | 1.81 |
|   |   | 4 |   | 1.09 | 294 | 309 | 311 | 1.79 |
|   |   | 5 |   | 1.10 | 300 | 312 | 314 | 1.82 |
|   |   | 6 |   | 1.10 | 309 | 317 | 320 | 1.68 |
|   |   | avg. |   | 1.11 | 301 | 312 | 314 | 1.79 |
| 2 |   | 1B | N2/CO2 (75%/25%) | 1.10 | 318 | 328 | 326 | 1.15 |
|   |   | 2B |   | 1.00 | 295 | 301 | 299 | 1.04 |
|   |   | 4B |   | 1.10 | 292 | 300 | 295 | 1.18 |
|   |   | 5B |   | 1.08 | 294 | 306 | 303 | 1.22 |
|   |   | 6B |   | 1.07 | 293 | 300 | 293 | 1.18 |

TABLE 6-continued

| | | | avg. | 1.07 | 298 | 307 | 303 | 1.15 |

| Expt. # | Material OGB # | Sample # | Balloon Internal Gas N2 or N2/CO2 | % Gas Gain T = 2 (Day 2) 9:00 AM (%) | 50% CO$_2$ T = 5 (Day 5) 9:00 am (cc) | 0% CO$_2$ T = 5 (Day 5) 7:00 PM End of Cycle (cc) | 0% CO$_2$ T = 5 (Day 5) 7:00 PM (psi) | % Gas Gain T = 5 (Day 5) 7:00 PM (%) |
|---|---|---|---|---|---|---|---|---|
| 1 | Non-Barrier Film | 1 | N2 | 7.4% | 323 | 319 | 2.50 | 12.3% |
| | | 3 | | 8.2% | 319 | 314 | 2.53 | 12.3% |
| | | 4 | | 9.5% | 321 | 313 | 2.56 | 14.1% |
| | | 5 | | 8.6% | 324 | 318 | 2.70 | 14.3% |
| | | 6 | | 6.9% | 329 | 328 | 2.58 | 13.9% |
| | | avg. | | 8.1% | 323 | 318 | 2.57 | 13.4% |
| 2 | | 1B | N2/CO2 (75%/25%) | 2.1% | 329 | 324 | 1.37 | 2.6% |
| | | 2B | | 1.2% | 302 | 297 | 1.28 | 1.8% |
| | | 4B | | 1.1% | 299 | 293 | 1.25 | 1.0% |
| | | 5B | | 2.9% | 305 | 302 | 1.16 | 2.4% |
| | | 6B | | 0.5% | 298 | 295 | 1.26 | 1.4% |
| | | avg. | | 1.6% | 307 | 302 | 1.26 | 1.8% |

| Expt. # | Material | Sample # | Balloon Internal Gas | 50% CO$_2$ T = 6 (Day 6) 8:00 AM (cc) | 50% CO$_2$ T = 6 (Day 6) 8:00 AM (psi) | % Gas Gain* T = 6 (Day 6) 8:00 AM End of Cycle (%) | 0% CO$_2$ T = 6 (Day 6) 7:00 PM (cc) | 0% CO$_2$ T = 6 (Day 6) 7:00 PM (psi) |
|---|---|---|---|---|---|---|---|---|
| 1 | Non-Barrier Film | 1 | N$_2$ | 323 | 3.03 | 16.0% | balloon cut during test | |
| | | 3 | | 320 | 3.01 | 16.3% | 318 | 2.84 |
| | | 4 | | 322 | 3.04 | 18.7% | 321 | 2.87 |
| | | 5 | | 322 | 3.19 | 17.7% | 322 | 2.98 |
| | | 6 | | 330 | 3.12 | 17.0% | 329 | 2.89 |
| | | avg. | | 323 | 3.08 | 17.1% | 323 | 2.90 |
| 2 | | 1B | N$_2$/CO$_2$ (75%/25%) | 329 | 1.82 | 5.7% | 329 | 1.48 |
| | | 2B | | 300 | 1.61 | 4.0% | 301 | 1.38 |
| | | 4B | | 299 | 1.64 | 4.2% | 298 | 1.46 |
| | | 5B | | 304 | 1.55 | 4.6% | 306 | 1.33 |
| | | 6B | | 299 | 1.62 | 4.0% | 298 | 1.41 |
| | | avg. | | 306 | 1.65 | 4.5% | 306 | 1.41 |

| Expt. # | Material | Sample # | Balloon Internal Gas | % Gas Gain T = 6 (Day 6) 7:00 PM (%) | 50% CO$_2$ T = 7 (Day 7) 8:00 AM (cc) | 50% CO$_2$ T = 7 (Day 7) 8:00 AM End of Cycle (psi) | % Gas Gain* T = 7 (Day 7) 8:00 AM (%) | 0% CO$_2$ T = 7 (Day 7) 7:00 PM (cc) |
|---|---|---|---|---|---|---|---|---|
| 1 | Non-Barrier Film | 1 | N$_2$ | balloon cut during test | | | | |
| | | 3 | | 14.9% | 322 | 3.02 | 16.8% | 319 |
| | | 4 | | 17.7% | 322 | 3.05 | 18.7% | 320 |
| | | 5 | | 16.7% | 325 | 3.15 | 18.3% | 323 |
| | | 6 | | 15.6% | 331 | 3.08 | 17.0% | 329 |
| | | avg. | | 16.2% | 325 | 3.08 | 17.7% | 323 |
| 2 | | 1B | N$_2$/CO$_2$ (75%/25%) | 4.2% | 327 | 1.63 | 4.4% | 326 |
| | | 2B | | 3.2% | 300 | 1.57 | 3.8% | 299 |
| | | 4B | | 3.1% | 299 | 1.61 | 4.0% | 296 |
| | | 5B | | 4.1% | 303 | 1.45 | 3.9% | 303 |

TABLE 6-continued

| | | | | | | | |
|---|---|---|---|---|---|---|---|
| | | 6B | | 2.8% | 300 | 1.60 | 4.1% | 297 |
| | | avg. | | 3.5% | 306 | 1.57 | 4.1% | 304 |

| Expt. # | Material | Sample # | Balloon Internal Gas | Pressure (Day 7) 7:00 PM T = 7 | $CO_2$ % (Day 7) 7:00 PM T = 7 (%) | Volume (Day 8) 8:00 AM End of Cycle T = 8 (cc) | Pressure (Day 8) 8:00 AM 50% $CO_2$ T = 8 (psi) | $CO_2$ % (Day 8) 8:00 AM % Gas Gain T = 8 (%) |
|---|---|---|---|---|---|---|---|---|
| 1 | Non-Barrier Film | 1 | $N_2$ | balloon cut during test | | | | |
| | | 3 | | 2.90 | 15.5% | 322 | 3.01 | 16.8% |
| | | 4 | | 2.92 | 17.7% | 323 | 2.99 | 18.8% |
| | | 5 | | 2.91 | 16.7% | 325 | 3.07 | 17.9% |
| | | 6 | | 2.88 | 15.6% | 332 | 3.03 | 17.1% |
| | | avg. | | 2.90 | 16.3% | 326 | 3.03 | 17.6% |
| 2 | | 1B | $N_2/CO_2$ | 1.42 | 3.3% | 329 | 1.43 | 4.0% |
| | | 2B | (75%/25%) | 1.37 | 2.7% | 301 | 1.42 | 3.4% |
| | | 4B | | 1.37 | 2.3% | 299 | 1.29 | 2.6% |
| | | 5B | | 1.23 | 2.9% | 306 | 1.32 | 4.0% |
| | | 6B | | 1.42 | 2.6% | 299 | 1.43 | 3.1% |
| | | avg. | | 1.36 | 2.8% | 307 | 1.38 | 3.4% |

| Expt. # | Material | Sample # | Balloon Internal Gas | Volume (Day 8) 7:00 PM 0% $CO_2$ T = 8 (cc) | Pressure (Day 8) 7:00 PM 0% $CO_2$ T = 8 (psi) | $CO_2$ % (Day 8) 7:00 PM % Gas Gain T = 8 (%) | Volume (Day 9) 8:00 AM End of Cycle 50% $CO_2$ T = 9 (cc) | Pressure (Day 9) 8:00 AM 50% $CO_2$ T = 9 (psi) |
|---|---|---|---|---|---|---|---|---|
| 1 | Non-Barrier Film | 1 | $N_2$ | balloon cut during test | | | | |
| | | 3 | | 318 | 2.88 | 15.1% | 323 | 2.96 |
| | | 4 | | 322 | 2.87 | 17.9% | 323 | 3.00 |
| | | 5 | | 325 | 2.96 | 17.4% | 323 | 3.01 |
| | | 6 | | 330 | 2.88 | 15.8% | 332 | 2.91 |
| | | avg. | | 324 | 2.90 | 16.6% | 325 | 2.97 |
| 2 | | 1B | $N_2/CO_2$ | 325 | 1.30 | 2.5% | 327 | 1.28 |
| | | 2B | (75%/25%) | 314 | 1.28 | 5.8% | 301 | 1.35 |
| | | 4B | | 300 | 1.32 | 3.0% | 298 | 1.45 |
| | | 5B | | 304 | 1.23 | 3.2% | 307 | 1.35 |
| | | 6B | | 299 | 1.34 | 2.7% | 299 | 1.39 |
| | | avg. | | 308 | 1.29 | 3.4% | 306 | 1.36 |

| Expt. # | Material | Sample # | Balloon Internal Gas | $CO_2$ % (Day 9) 8:00 AM T = 9 (%) | Volume (Day 12) 8:00 AM T = 8 (cc) | Pressure (Day 12) 8:00 AM End of Cycle T = 8 (psi) | $CO_2$ % (Day 12) 8:00 AM % Gas Gain* T = 8 (%) | Volume (Day 13) 8:00 AM 50% CO2 T = 9 (cc) |
|---|---|---|---|---|---|---|---|---|
| 1 | Non-Barrier Film | 1 | $N_2$ | balloon cut during test | | | | |
| | | 3 | | 16.8% | 323 | 3.00 | 17.0% | 325 |
| | | 4 | | 18.8% | 322 | 3.25 | 19.7% | 326 |
| | | 5 | | 17.1% | 325 | 3.27 | 18.8% | 327 |
| | | 6 | | 16.5% | 330 | 3.25 | 17.6% | 333 |
| | | avg. | | 17.3% | 325 | 3.19 | 18.3% | 328 |
| 2 | | 1B | $N_2/CO_2$ | 2.9% | 326 | 1.62 | 4.2% | 330 |
| | | 2B | (75%/25%) | 3.1% | 302 | 1.62 | 4.5% | 304 |
| | | 4B | | 3.1% | 298 | 1.42 | 3.0% | 300 |
| | | 5B | | 4.4% | 305 | 1.66 | 5.3% | 309 |

TABLE 6-continued

| | | | | | | |
|---|---|---|---|---|---|---|
| | 6B | | 3.0% | 298 | 1.58 | 3.6% | 298 |
| | avg. | | 3.3% | 306 | 1.58 | 4.1% | 308 |

| Expt. # | Material | Sample # | Balloon Internal Gas | Pressure (Day 13) 8:00 AM 50% CO2 T = 9 (psi) | CO$_2$ % (Day 13) 8:00 AM % Gas Gain* T = 9 (%) | Volume (Day 14) 8:00 AM End of Cycle 50% CO2 T = 10 (cc) | Pressure (Day 14) 8:00 AM 50% CO2 T = 10 (psi) | CO$_2$ % (Day 14) 8:00 AM % Gas Gain* T = 10 (%) |
|---|---|---|---|---|---|---|---|---|
| 1 | Non-Barrier Film | 1 | N$_2$ | | | | | |
| | | 3 | | 3.37 | 19.2% | 323 | 3.25 | 18.1% |
| | | 4 | | 3.36 | 21.2% | 327 | 3.21 | 20.7% |
| | | 5 | | 3.38 | 19.8% | 326 | 3.36 | 19.5% |
| | | 6 | | 3.30 | 18.5% | 334 | 3.30 | 18.8% |
| | | avg. | | 3.35 | 19.7% | 328 | 3.28 | 19.3% |
| 2 | | 1B | N$_2$/CO$_2$ (75%/25%) | 1.68 | 5.3% | 329 | 1.68 | 5.1% |
| | | 2B | | 1.69 | 5.3% | 302 | 1.48 | 3.9% |
| | | 4B | | 1.56 | 4.1% | 299 | 1.43 | 3.3% |
| | | 5B | | 1.69 | 6.3% | 307 | 1.57 | 5.3% |
| | | 6B | | 1.70 | 4.1% | 300 | 1.66 | 4.4% |
| | | avg. | | 1.66 | 5.0% | 307 | 1.56 | 4.4% |

Balloons constructed with various composite walls, a barrier material Nylon12/PvDC/Nylon12/LLDPE+LDPE) and a non-barrier material (multi-layer Nylon12/LLDPE+LDPE) were tested in a simulated gastric environment (tank containing a 1.2 pH HCl solution with NaCl and pepsin at 40° C. with a variable N$_2$/CO$_2$ headspace (75%/25% to 100%/0%)). The balloons were initially filled with a mixture of N$_2$ (75%) and CO$_2$ (25%). Pressure for the balloons fabricated from CO$_2$ barrier materials maintained pressure and volume over the time period tested, whereas the balloons fabricated from CO$_2$ non-barrier materials exhibited substantial pressure gain over the same time period, with a smaller volume gain. Results are presented in Table 7

TABLE 7

| Exp. | Material | Sample | Balloon Internal Gas | Volume (Day 0) (cc) | Pressure (Day 0) (psi) | Volume (Day 1) (cc) | Pressure (Day 1) (psi) |
|---|---|---|---|---|---|---|---|
| 1 | Barrier | 1 | N$_2$/CO$_2$ (75%/25%) | | | 280 | 1.05 |
| | | 2 | | | | 279 | 1.03 |
| | | avg. | | | | 280 | 1.04 |
| 2 | Barrier | 1 | N$_2$/CO$_2$ (75%/25%) | | | 279 | 1.06 |
| | | 2 | | | | 278 | 1.07 |
| | | avg. | | | | 279 | 1.07 |
| 3 | Barrier | 1 | N$_2$/CO$_2$ (75%/25%) | | | 280 | 1.05 |
| | | 2 | | | | 278 | 1.02 |
| | | avg. | | | | 279 | 1.04 |
| 4 | Barrier | 1 | N$_2$/CO$_2$ (75%/25%) | 296 | 1.14 | | |
| | | 2 | | 295 | 1.05 | | |
| | | avg. | | 296 | 1.10 | | |
| 5 | Non-Barrier | 1 | N$_2$/CO$_2$ (75%/25%) | 304 | 1.12 | | |
| | | 2 | | 292 | 1.11 | | |
| | | avg. | | 298 | 1.12 | | |
| 6 | Non-Barrier | 1 | N$_2$/CO$_2$ (75%/25%) | 298 | 1.15 | | |
| | | 2 | | 294 | 1.14 | | |
| | | avg. | | 296 | 1.15 | | |
| 7 | Non-Barrier | 1 | N$_2$/CO$_2$ (75%/25%) | 297 | 1.14 | | |
| | | 2 | | 302 | 1.15 | | |
| | | avg. | | 300 | 1.15 | | |
| 8 | Barrier | 1 | N$_2$/CO$_2$ (75%/25%) | 298 | 1.11 | | |
| | | 2 | | 302 | 1.12 | | |
| | | avg. | | 300 | 1.12 | | |
| 9 | Barrier | 1 | N$_2$/CO$_2$ (75%/25%) | 294 | 1.18 | | |
| | | 2 | | 291 | 1.13 | | |
| | | avg. | | 293 | 1.16 | | |

| Exp. | Material | Sample | Balloon Internal Gas | Volume (Day 2) (cc) | Pressure (Day 2) (psi) | Volume (Day 3) (cc) | Pressure (Day 3) (psi) |
|---|---|---|---|---|---|---|---|
| 1 | Barrier | 1 | N$_2$/CO$_2$ (75%/25%) | | | 286 | 1.05 |
| | | 2 | | | | 284 | 1.01 |
| | | avg. | | | | 285 | 1.03 |

TABLE 7-continued

| Exp. | Material | Sample | Balloon Internal Gas | Volume (cc) | Pressure (psi) |
|---|---|---|---|---|---|
| 2 | Barrier | 1 | $N_2/CO_2$ | 283 | 0.97 |
|   |   | 2 | (75%/25%) | 282 | 1.04 |
|   |   | avg. |   | 283 | 1.01 |
| 3 | Barrier | 1 | $N_2/CO_2$ | 287 | 1.05 |
|   |   | 2 | (75%/25%) | 280 | 0.97 |
|   |   | avg. |   | 284 | 1.01 |
| 4 | Barrier | 1 | $N_2/CO_2$ | 303 | 1.28 |
|   |   | 2 | (75%/25%) | 303 | 1.18 |
|   |   | avg. |   | 303 | 1.23 |
| 5 | Non-Barrier | 1 | $N_2/CO_2$ | 313 | 2.26 |
|   |   | 2 | (75%/25%) | 312 | 2.37 |
|   |   | avg. |   | 313 | 2.32 |
| 6 | Non-Barrier | 1 | $N_2/CO_2$ | 308 | 2.34 |
|   |   | 2 | (75%/25%) | 301 | 2.15 |
|   |   | avg. |   | 305 | 2.25 |
| 7 | Non-Barrier | 1 | $N_2/CO_2$ | 307 | 2.17 |
|   |   | 2 | (75%/25%) | 312 | 2.22 |
|   |   | avg. |   | 310 | 2.20 |
| 8 | Barrier | 1 | $N_2/CO_2$ | 303 | 1.28 |
|   |   | 2 | (75%/25%) | 303 | 1.28 |
|   |   | avg. |   | 303 | 1.28 |
| 9 | Barrier | 1 | $N_2/CO_2$ | 301 | 1.24 |
|   |   | 2 | (75%/25%) | 298 | 1.24 |
|   |   | avg. |   | 300 | 1.24 |

| Exp. | Material | Sample | Balloon Internal Gas | Volume (Day 4) (cc) | Pressure (Day 4) (psi) | Volume (Day 5) (cc) | Pressure (Day 5) (psi) |
|---|---|---|---|---|---|---|---|
| 1 | Barrier | 1 | $N_2/CO_2$ | 289 | 1.08 | 292 | 1.07 |
|   |   | 2 | (75%/25%) | 287 | 1.03 | 292 | 1.04 |
|   |   | avg. |   | 288 | 1.06 | 292 | 1.06 |
| 2 | Barrier | 1 | $N_2/CO_2$ | 284 | 1.14 | 287 | 1.01 |
|   |   | 2 | (75%/25%) | 286 | 1.13 | 287 | 1.02 |
|   |   | avg. |   | 285 | 1.14 | 287 | 1.02 |
| 3 | Barrier | 1 | $N_2/CO_2$ | 285 | 1.09 | 287 | 1.05 |
|   |   | 2 | (75%/25%) | 285 | 1.05 | 286 | 1.00 |
|   |   | avg. |   | 285 | 1.07 | 287 | 1.03 |
| 4 | Barrier | 1 | $N_2/CO_2$ | 308 | 1.35 | 309 | 1.36 |
|   |   | 2 | (75%/25%) | 306 | 1.39 | 306 | 1.29 |
|   |   | avg. |   | 307 | 1.37 | 308 | 1.33 |
| 5 | Non-Barrier | 1 | $N_2/CO_2$ | 320 | 2.44 | 322 | 2.51 |
|   |   | 2 | (75%/25%) | 315 | 2.59 | 315 | 2.58 |
|   |   | avg. |   | 318 | 2.52 | 319 | 2.55 |
| 6 | Non-Barrier | 1 | $N_2/CO_2$ | 311 | 2.48 | 312 | 2.59 |
|   |   | 2 | (75%/25%) | 306 | 2.39 | 308 | 2.51 |
|   |   | avg. |   | 309 | 2.44 | 310 | 2.55 |
| 7 | Non-Barrier | 1 | $N_2/CO_2$ | 310 | 2.43 | 308 | 2.45 |
|   |   | 2 | (75%/25%) | 315 | 2.43 | 316 | 2.54 |
|   |   | avg. |   | 313 | 2.43 | 312 | 2.50 |
| 8 | Barrier | 1 | $N_2/CO_2$ | 305 | 1.39 | 305 | 1.36 |
|   |   | 2 | (75%/25%) | 303 | 1.34 | 306 | 1.31 |
|   |   | avg. |   | 304 | 1.37 | 306 | 1.34 |
| 9 | Barrier | 1 | $N_2/CO_2$ | 303 | 1.30 | 304 | 1.29 |
|   |   | 2 | (75%/25%) | 298 | 1.35 | 299 | 1.33 |
|   |   | avg. |   | 301 | 1.33 | 302 | 1.31 |

Balloons constructed with composite walls with high $CO_2$ barrier properties (Experiments 1, 2, and 3) (Nylon12/PvDC/Nylon 12/LLDPE+LDPE) and walls having a higher permeability to $CO_2$ (Experiments 4, 5, and 6) consisting of multi-layer Nylon12/LLDPE+LDPE were exposed to a stimulated gastric environment. The simulated gastric environment comprised a tank containing a 1.2 pH HCl solution with NaCl and pepsin at 40° C. The headspace in the tank was cycled from a gas mixture comprising 75% $N_2$/25% $CO_2$ headspace to one comprising 100% $N_2$/0% $CO_2$. The balloons were initially filled with various mixtures of $N_2$ and $CO_2$, and volume was monitored. Data regarding volume changes are provided in Table 8. The balloons constructed using walls having a higher permeability to $CO_2$ gained substantially in volume compared to those with high $CO_2$ barrier properties. For the balloons constructed using walls having a higher permeability to $CO_2$, those with higher ratios of $N_2$ to $CO_2$ as initial fill gas gained less volume than those with lower ratios of $N_2$ to $CO_2$. The data demonstrate that permeation of $CO_2$ into balloons fabricated with walls having a higher permeability to $CO_2$ occurs quickly in the gastric environment, and that this process can be employed to assist with inflation in the early stages of implant.

TABLE 8

| Experiment | Material | Sample | Balloon Internal Gas | Volume (Day 1) 5:00 PM (cc) | Pressure (Day 1) 5:00 PM (psi) | Volume (Day 2) 8:00 AM (cc) | Pressure (Day 2) 8:00 AM (psi) |
|---|---|---|---|---|---|---|---|
| 1 | Barrier | 1 | N2/CO2 | 298 | 1.07 | 301 | 1.08 |
|  |  | 2 | (92%/8%) | 293 | 1.02 | 293 | 1.06 |
|  |  | 3 |  | 285 | 1.00 | 287 | 1.05 |
|  |  | avg. |  | 296 | 1.05 | 297 | 1.07 |
| 2 | Barrier | 1 | N2/CO2 | 286 | 1.09 | 287 | 1.09 |
|  |  | 2 | (90%/10%) | 291 | 1.09 | 294 | 1.14 |
|  |  | 3 |  | 293 | 1.08 | 298 | 1.13 |
|  |  | avg. |  | 290 | 1.09 | 304 | 1.20 |
| 3 | Barrier | 1 | N2/CO2 | 290 | 1.10 | 295 | 1.15 |
|  |  | 2 | (85%/15%) | 290 | 1.02 | 290 | 1.03 |
|  |  | 3 |  | 299 | 1.16 | 304 | 1.20 |
|  |  | avg. |  | 293 | 1.09 | 293 | 1.09 |
| 4 | Non-Barrier | 1 | N2/CO2 | 290 | 1.04 | 298 | 1.54 |
|  |  | 2 | (92%/8%) | 292 | 1.07 | 300 | 1.60 |
|  |  | 3 |  | 291 | 1.09 | 301 | 1.68 |
|  |  | avg. |  | 291 | 1.07 | 299 | 1.57 |
| 5 | Non-Barrier | 1 | N2/CO2 | 283 | 1.07 | 293 | 1.64 |
|  |  | 2 | (90%/10%) | 287 | 1.05 | 295 | 1.60 |
|  |  | 3 |  | 290 | 1.00 | 300 | 1.48 |
|  |  | avg. |  | 287 | 1.04 | 294 | 1.62 |
| 6 | Non-Barrier | 1 | N2/CO2 | 287 | 1.06 | 297 | 1.76 |
|  |  | 2 | (85%/15%) | 298 | 1.07 | 307 | 1.66 |
|  |  | 3 |  | 290 | 1.13 | 304 | 1.78 |
|  |  | avg. |  | 292 | 1.09 | 302 | 1.71 |

| Experiment | Material | Sample | Balloon Internal Gas | Volume (Day 2) 8:30 PM (cc) | Pressure (Day 2) 8:30 PM (psi) | Volume (Day 3) 8 AM (cc) | Pressure (Day 3) 8 AM (psi) |
|---|---|---|---|---|---|---|---|
| 1 | Barrier | 1 | N2/CO2 | 301 | 1.11 | 301 | 1.13 |
|  |  | 2 | (92%/8%) | 295 | 1.06 | 302 | 1.10 |
|  |  | 3 |  | 284 | 1.03 | 289 | 1.07 |
|  |  | avg. |  | 298 | 1.09 | 302 | 1.12 |
| 2 | Barrier | 1 | N2/CO2 | 287 | 1.13 | 287 | 1.12 |
|  |  | 2 | (90%/10%) | 294 | 1.13 | 296 | 1.17 |
|  |  | 3 |  | 297 | 1.15 | 300 | 1.19 |
|  |  | avg. |  | 293 | 1.14 | 294 | 1.16 |
| 3 | Barrier | 1 | N2/CO2 | 294 | 1.17 | 297 | 1.21 |
|  |  | 2 | (85%/15%) | 290 | 1.08 | 294 | 1.10 |
|  |  | 3 |  | 302 | 1.27 | 308 | 1.27 |
|  |  | avg. |  | 295 | 1.17 | 300 | 1.19 |

TABLE 8-continued

| | | | | | | | | |
|---|---|---|---|---|---|---|---|---|
| 4 | Non-Barrier | 1 | N2/CO2 (92%/8%) | 296 | 1.48 | 297 | 1.72 |
| | | 2 | | 298 | 1.55 | 302 | 1.81 |
| | | 3 | | 296 | 1.65 | 301 | 1.80 |
| | | avg. | | 297 | 1.56 | 300 | 1.78 |
| 5 | Non-Barrier | 1 | N2/CO2 (90%/10%) | 291 | 1.56 | 294 | 1.80 |
| | | 2 | | 295 | 1.50 | 295 | 1.67 |
| | | 3 | | 298 | 1.44 | 301 | 1.65 |
| | | avg. | | 293 | 1.53 | 297 | 1.71 |
| 6 | Non-Barrier | 1 | N2/CO2 | 295 | 1.76 | 300 | 1.99 |

Human Gastric Environment

Balloons constructed with non-barrier film composite walls were tested in vivo in 10 patients in a clinical study for 30 days. The balloon wall comprised multi-layer Nylon 12/LLDPE+LDPE. One balloon per patient was administered. Balloons were filled with a mixed gas to approximately 245 cc with an average starting balloon pressure of 1.01 psi above atmosphere. The initial fill gas was 95% Nitrogen and 5% $CO_2$. At the end of 30 days, balloons remained full and firm, although ending pressure and volumes could not be discerned visually/endoscopically. Of the 10 balloons retrieved, 10 balloons had internal gas samples obtained, and 8 provided meaningful data. Table 9 provides the data retrieved from the balloons. The end gas samples are reflective of the gastric environment and are averaged as follows: 82.4% $N_2$, 10.6% $O_2$, 5.9% $CO_2$, and 0.84% Ar. Thus, the internal balloon environment reflects that of the average gastric environment gas concentrations. Data for the experiments is provided in Table 9.

TABLE 9

| Patient # | Starting Balloon Gas Concentration | | Ending Balloon Gas Concentration (% v/v, by MS) | | | |
|---|---|---|---|---|---|---|
| Patient # | [N2] | [CO2] | [N2] | [O2] | [CO2] | [Ar] |
| 1 | 95.00 | 5.00 | 81.19 | 10.20 | 7.60 | 0.86 |
| 2 | 95.00 | 5.00 | 81.24 | 12.90 | 4.85 | 0.86 |
| 3 | 95.00 | 5.00 | 82.41 | 10.80 | 5.65 | 0.85 |
| 4 | 95.00 | 5.00 | 82.07 | 11.20 | 5.70 | 0.82 |
| 5 | 95.00 | 5.00 | 82.87 | 10.05 | 6.00 | 0.82 |
| 6 | 95.00 | 5.00 | 82.54 | 11.50 | 4.80 | 0.88 |
| 7 | 95.00 | 5.00 | Erroneous Sample | | | |
| 8 | 95.00 | 5.00 | 81.76 | 10.20 | 7.00 | 0.82 |
| 9 | 95.00 | 5.00 | Erroneous Sample | | | |
| 10 | 95.00 | 5.00 | 84.95 | 8.20 | 5.80 | 0.81 |
| Avg. | | | 82.38 | 10.63 | 5.93 | 0.84 |
| Std Dev | | | 1.20 | 1.36 | 0.97 | 0.03 |
| Max | | | 84.95 | 12.90 | 7.60 | 0.88 |
| Min | | | 81.19 | 8.20 | 4.80 | 0.81 |

In certain embodiments wherein it is desirable to maintain the starting pressure and volume of the device, this can be accomplished by matching the internal balloon environment at implant (i.e., the fill gases) closely to the gastric environment. In such embodiments, the balloon can be inflated with an initial gas fill gas comprising approximately 80-85% nitrogen, 8-12% oxygen, and 4-8% carbon dioxide. The concentration of argon and other in vivo gases can be considered inconsequential to the total volume/pressure, and may be omitted for convenience or included as desirable. To encourage inflation of the balloon in vivo, the starting concentrations of oxygen and/or carbon dioxide can be reduced.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An intragastric balloon configured to have a useful life in an in vivo gastric environment of at least 30 days, comprising:
    a component configured for detection by an ultrasonic detector;
    a polymeric wall configured to have, under conditions of an in vivo gastric environment, a permeability to $CO_2$ of more than 10 cc/m$^2$/day, such that a rate and an amount of diffusion of $CO_2$ from the in vivo gastric environment into a lumen of the intragastric balloon through the polymeric wall is controlled, at least in part, by a concentration of $CO_2$ and a concentration of a gas selected from the group consisting of $N_2$, $SF_6$, $C_2F_6$, $C_3F_8$, $C_4F_{10}$, $C_4F_8$, $C_3F_6$, $CF_4$, $CClF_2$-$CF_3$, and mixtures thereof in an initial fill gas, wherein the concentration of $CO_2$ in the initial fill gas is characteristic of gastric $pCO_2$; and
    a valve system configured for introducing the initial fill gas into the lumen of the intragastric balloon in the in vivo gastric environment;
    wherein the component configured for detection by an ultrasonic detector comprises a first coiled conductor coupled with the intragastric balloon and a second coiled conductor separate from the intragastric balloon, and wherein the ultrasonic detector comprises a spectrum analyzer configured to measure resonant frequencies associated with the intragastric balloon.

2. The intragastric balloon of claim 1, wherein the polymeric wall is configured to have, under conditions of an in vivo gastric environment, a permeability to $CO_2$ of more than 50 cc/m$^2$/day.

3. A method for positioning an intragastric balloon, comprising:
    introducing into a patient, via swallowing, an intragastric balloon comprising an ultrasonic component configured for detection by an ultrasonic detector, and a polymeric wall, wherein the intragastric balloon is in a compacted, solid form;
    confirming, by sensing resonant frequencies associated with the intragastric balloon in a compacted, solid form, a location of the intragastric balloon, wherein the location is the patient's stomach; thereafter
    introducing an initial fill gas into a lumen of the intragastric balloon, wherein the initial fill gas comprises a gas selected from the group consisting of $N_2$, $SF_6$, $C_2F_6$, $C_3F_8$, $C_4F_{10}$, $C_4F_8$, $C_3F_6$, $CF_4$, $CClF_2\text{-}CF_3$, and mixtures thereof; and exposing the intragastric balloon to the in vivo intragastric environment for a useful life of at least 30 days, wherein the intragastric balloon maintains a volume of 75% to 125% of its original nominal volume over the useful life;

after the exposing the intragastric balloon to the in vivo intragastric environment, deflating the intragastric balloon, wherein the deflating comprises bursting the intragastric balloon by administration of an ultrasonic or acoustic pulse.

4. The method of claim 3, further comprising, after introducing the initial fill gas, confirming, by sensing resonant frequencies associated with the intragastric balloon in inflated form, complete inflation of the intragastric balloon.

5. The method of claim 3, further comprising, during the exposing the intragastric balloon to the in vivo intragastric environment, a degree of inflation of the intragastric balloon.

6. The method of claim 3, wherein the initial fill gas further comprises $CO_2$.

7. The method of claim 3,
wherein the ultrasonic component comprises a first coiled conductor coupled with the intragastric balloon and a second coiled conductor separate from the intragastric balloon, and wherein the ultrasonic detector comprises a spectrum analyzer configured to measure resonant frequencies associated with the intragastric balloon.

8. The method of claim 7, wherein the polymeric wall is configured to have, under conditions of an in vivo gastric environment, a permeability to $CO_2$ of more than 10 $cc/m^2$/day.

9. The method of claim 7, wherein the polymeric wall is configured to have, under conditions of an in vivo gastric environment, a permeability to $CO_2$ of more than 10 $cc/m^2$/day, such that a rate and an amount of diffusion of $CO_2$ from the in vivo gastric environment into a lumen of the intragastric balloon through the polymeric wall is controlled, at least in part, by a concentration of an inert gas and a concentration of $CO_2$ in an initial fill gas, wherein the concentration of $CO_2$ in the initial fill gas is characteristic of gastric $pCO_2$.

10. The method of claim 7, wherein the polymeric wall is configured to have, under conditions of an in vivo gastric environment, a permeability to $CO_2$ of more than 50 $cc/m^2$/day.

* * * * *

UNITED STATES PATENT AND TRADEMARK OFFICE
CERTIFICATE OF CORRECTION

PATENT NO. : 9,895,248 B2
APPLICATION NO. : 14/877846
DATED : February 20, 2018
INVENTOR(S) : Mark C. Brister It is certified that error appears in the above-identified patent and that said Letters Patent is hereby corrected as shown below:

In Column 1 at Line 14 (approx.), Change "Oct. 9, 2015." to --Oct. 9, 2014.--.

In Column 8 at Line 59, Change "radioopacity" to --radiopacity--.

In Column 9 at Line 30, Change "occupyable" to --occupiable--.

In Column 9 at Line 45, Change "is are" to --is--.

In Column 13 at Line 23, Change "occupyable" to --occupiable--.

In Column 13 at Line 24, Change "occupyable" to --occupiable--.

In Column 13 at Line 26, Change "occupyable" to --occupiable--.

In Column 20 at Line 22, After "150%" insert --.--.

In Column 30 at Line 45, Change "(6additional" to --(6 additional--.

In Column 33 at Line 31 (approx.), Change "mm/mg-24" to --mm/m2-24--.

In Column 33 at Line 32, Change "cc-mm/mg-24" to --cc-mm/m2-24--.

In Column 33 at Line 35, Change "5000 l/s;" to --5000 1/s;--.

In Column 33 at Line 36, Change "5000 l/s;" to --5000 1/s;--.

In Column 34 at Line 7, Change "tanks" to --tanks.--.

In Column 34 at Line 34, Change "cc-mm/mg-24" to --cc-mm/m$^2$-24--.

Signed and Sealed this
Twenty-second Day of May, 2018

Andrei Iancu
*Director of the United States Patent and Trademark Office*

CERTIFICATE OF CORRECTION (continued)

In Column 34 at Line 35, Change "cc-mm/mg-24" to --cc-mm/m2-24--.

In Column 37 at Line 10, Change "kind" to --kind.--.

In Column 37 at Line 56, Change "cc-mm/mg-24" to --cc-mm/m$^2$-24--.

In Column 40 at Line 60, Change "machining" to --machining.--.

In Column 45 at Line 17, Change "that that" to --that--.

In Column 48 at Line 57, Change "Biaxally" to --Biaxially--.

In Column 53 at Line 61, Change "C$_4$F$_8$, C$_4$F$_8$," to --C$_4$F$_8$,--.

In Column 60 at Line 26, After "embodiments" insert --.--.

In Column 69 at Line 14, Change "I=I$_0$ sin ωt," to --I=I$_0$ sinωt,--.

In Column 69 at Line 34, Change "E=–dΦ/dt=–A$_2$·B=A$_2$μ·N$_1$·ω$_1$·I$_0$·(cos ωt)/d$_1$" to --E=–dΦ/dt=–A$_2$·B=A$_2$μ·N$_1$·ω$_1$·I$_0$·(cosωt)/d$_1$--.

In Column 69 at Line 42 (approx.), Change "L=N·Φ/i=N·A·μ·N/l=N$^2$·A·μ/d$_1$" to --L=N·Φ/i=N·A·μ·N/1=N$^2$·A·μ/d$_1$--.

In Column 69 at Line 56 (approx.), Change "N$_2$·Φ$_{21}$=N$_2$·N$_1$·πμ$_0$·R$_2^2$·$_{i1}$/2·R$_1$," to --N$_2$·Φ$_{21}$=N$_2$·N$_1$·π·μ$_0$·R$_2^2$·$_{i1}$/2·R$_1$,--.

In Column 70 at Line 49 (approx.), Change "1/L·dV/dt=d$^2$I/dt$^2$+(1·τ)·dI/dt+ω$_0^2$·I," to --1/L·dV/dt=d$^2$I/dt$^2$+(1/τ)·dI/dt+ω$_0^2$·I,--.

In Column 71 at Line 12, Change "V$_1$=L$_1$·d$^2$/dt$^2$+M·–M/L$_2$·d$^2$I$_1$/dt$^2$+I$_1$·R$_1$+1/C·∫I$_1$·dt." to --V$_1$=L$_1$·d$^2$I$_1$/dt$^2$+M·–M/L$_2$·d$^2$I$_1$/d$^2$+I$_1$·R$_1$+1/C·∫I$_1$·dt.--.

In Column 71 at Line 65, Change "$Q=\omega_n \cdot L/R = \sqrt{1(L \cdot C)} \cdot L/R = 1R \sqrt{L/C}$" to --$Q=\omega_n \cdot L/R = \sqrt{1/(L \cdot C)} \cdot L/R = 1/R \sqrt{L/C}$--.

In Column 72 at Line 8 (approx.), Change "L$_1$=N$_1^{2 \cdot A}{}_1$·μ/d$_1$," to --$L_1 = N_1^2 \cdot A_1 \cdot \mu / d_1$,--.

In Column 72 at Line 20, Change "4$N_1^2 \cdot N_2^2 \cdot A_1^2 \cdot A_2 \cdot \mu^2$" to --4·$N_1^2 \cdot N_2^2 \cdot A_1^2 \cdot A_2 \cdot \mu^2$--.

In Column 72 at Line 63, Change "$L_2 N_2^2 \cdot A_2 \cdot \mu / d_2$" to --$L_2 = N_2^2 \cdot A_2 \cdot \mu / d_2$--.

In Column 72 at Line 67, Change "$A_1 A_2 d_1 d_2 / 4\pi_2 (R_1^2 + z^2)^3$" to --$A_1 A_2 d_1 d_2 / 4\pi^2 (R_1^2 + z^2)^3$--.

In Column 76 at Line 19, Change "Or" to --or--.

CERTIFICATE OF CORRECTION (continued)
U.S. Pat. No. 9,895,248 B2

In Column 94 at Line 31, After "Table 7" insert --.--.

In Column 102 at Line 37, In Claim 1, change "CC1F$_2$-CF$_3$," to --CClF$_2$-CF$_3$,--.

In Column 103 at Line 2, In Claim 3, change "CC1F$_2$-CF$_3$," to --CClF$_2$-CF$_3$,--.